US011919972B2

(12) United States Patent
Eliasen

(10) Patent No.: US 11,919,972 B2
(45) Date of Patent: Mar. 5, 2024

(54) PEPTIDE LIBRARIES WITH NON-CANONICAL AMINO ACIDS

(71) Applicant: REGENERON PHARMACEUTICALS, INC., Tarrytown, NY (US)

(72) Inventor: Anders Eliasen, Culver City, CA (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 0 days.

(21) Appl. No.: 16/673,657

(22) Filed: Nov. 4, 2019

(65) Prior Publication Data

US 2020/0140487 A1 May 7, 2020

Related U.S. Application Data

(60) Provisional application No. 62/755,403, filed on Nov. 2, 2018.

(51) Int. Cl.
| | |
|---|---|
| *C07K 7/06* | (2006.01) |
| *A61K 49/00* | (2006.01) |
| *A61K 49/14* | (2006.01) |
| *A61K 51/08* | (2006.01) |
| *C12N 15/10* | (2006.01) |
| *G01N 33/68* | (2006.01) |

(52) U.S. Cl.
CPC ............ *C07K 7/06* (2013.01); *A61K 49/0002* (2013.01); *A61K 49/14* (2013.01); *A61K 51/08* (2013.01); *C12N 15/1072* (2013.01); *G01N 33/68* (2013.01)

(58) Field of Classification Search
CPC ...... A61K 51/00; A61K 51/08; A61K 51/088; A61K 49/00; A61K 49/0002; A61K 49/14; A61K 49/085; C07K 7/06; C07K 7/56; C12N 15/1072; G01N 33/68; G01N 33/53; C40B 40/10
USPC .... 424/1.11, 1.65, 1.69, 9.1, 9.2, 1.81, 1.85, 424/1.89; 514/1, 1.1, 21.91, 21.9, 21.8, 514/21.6, 21.7, 21.5, 21.4; 530/300
See application file for complete search history.

(56) References Cited

U.S. PATENT DOCUMENTS

| | | | |
|---|---|---|---|
| 4,899,755 | A | 2/1990 | Lauffer |
| 5,474,756 | A | 12/1995 | Tweedle |
| 5,846,519 | A | 12/1998 | Tweedle |
| 6,143,274 | A | 11/2000 | Tweedle |
| 10,017,540 | B2 | 7/2018 | Henning |
| 10,597,425 | B2 | 3/2020 | Pfeilsticker |
| 10,913,774 | B2 | 2/2021 | Henning |
| 11,414,460 | B2 | 8/2022 | Heath |
| 2006/0008848 | A1 | 1/2006 | Verdine |
| 2010/0009896 | A1 | 1/2010 | Agnew |
| 2015/0078999 | A1* | 3/2015 | Heath ............ C07K 5/08 424/1.69 |
| 2016/0264627 | A1 | 9/2016 | Henning |
| 2017/0319722 | A1 | 11/2017 | Agnew |
| 2018/0319844 | A1 | 11/2018 | Henning |
| 2021/0032293 | A1 | 2/2021 | Heath |

FOREIGN PATENT DOCUMENTS

| | | |
|---|---|---|
| CN | 110251695 | 9/2019 |
| EP | 3689892 | 8/2020 |
| WO | 1986/006605 | 11/1986 |
| WO | 1986006605 | 11/1986 |
| WO | 1991/003200 | 3/1991 |
| WO | 1991003200 | 3/1991 |

(Continued)

OTHER PUBLICATIONS

Agnew, et al., "Iterative In Situ Click Chemistry Creates Antibody□like Protein□Capture Agents", Angew. Chemie Int. Ed., 48(27):4944-4948 (2009).
Alexander, et al., "Intracranial black□blood MR angiography with hi gh□resolution 3D fast spin echo", Magn. Reson. Med., 40: 298-310 (1998).
Altschul, et al., "Gapped BLAST and PSI-BLAST: a new generation of protein database search programs", Nucleic Acids Res. 25:3389-402 (1997).
Araghi, et al., "Rapid Optimization of Mcl-1 inhibitors using Stapled Peptide Libraries Including Non-Natural Side Chains", ACS Chem. Biol., 11(5):1238-1244 (2016).

(Continued)

*Primary Examiner* — D. L. Jones
(74) *Attorney, Agent, or Firm* — PABST PATENT GROUP LLP

(57) ABSTRACT

Disclosed are peptides having non-canonical amino acids. These peptides are useful, for example, as protein binding agents. Libraries of such peptides can be used, for example to screen and select protein binding agents. The broader chemical space of the disclosed peptides can provide peptide with different, improved, more specific, and/or pharmaceutically compatible peptides and protein binding agents. In some forms, the peptides can have the following structure (I):

(I)

$$R-\underset{H}{N}-\underset{\underset{O}{\parallel}}{\overset{R^1}{C}}\underset{y^1(M)\diagdown_{SEQ}\diagup^{(M)}_{y^2}}{\overset{L^2}{\diagdown}}\overset{G}{\diagup}L^1$$

including stereoisomers, pharmaceutically acceptable salts and prodrugs thereof, wherein R, $R^1$, $L^1$, $L^2$, G, M, $Y^1$ $Y^2$ and SEQ are as defined herein. Methods associated with preparation and use of such peptides, as well as pharmaceutical compositions comprising such peptides, are also disclosed.

28 Claims, 1 Drawing Sheet

Specification includes a Sequence Listing.

(56) References Cited

FOREIGN PATENT DOCUMENTS

| WO | 1995/028179 | 10/1995 |
|---|---|---|
| WO | 1995028179 | 10/1995 |
| WO | 1995028967 | 11/1995 |
| WO | 1996/023526 | 8/1996 |
| WO | 1996023526 | 8/1996 |
| WO | 1997/036619 | 10/1997 |
| WO | 1997036619 | 10/1997 |
| WO | 1998/018496 | 5/1998 |
| WO | 1998/018497 | 5/1998 |
| WO | 1998018496 | 5/1998 |
| WO | 1998018497 | 5/1998 |
| WO | 1998/046612 | 10/1998 |
| WO | 1998046612 | 10/1998 |
| WO | 1999/017809 | 4/1999 |
| WO | 1999017809 | 4/1999 |
| WO | 1995/028967 | 11/2005 |
| WO | 2009/155420 | 12/2009 |
| WO | 2009155420 | 12/2009 |
| WO | 2012021874 | 2/2012 |
| WO | 2012/106671 | 8/2012 |
| WO | 2012106671 | 8/2012 |
| WO | 2013/009869 | 1/2013 |
| WO | 2013009869 | 1/2013 |
| WO | 2013/033561 | 3/2013 |
| WO | 2013033561 | 3/2013 |
| WO | 2014/074907 | 5/2014 |
| WO | 2014074907 | 5/2014 |
| WO | 2014/205317 | 12/2014 |
| WO | 2014205317 | 12/2014 |
| WO | 2015160770 | 10/2015 |
| WO | 2017/176769 | 10/2017 |
| WO | 2017176769 | 10/2017 |
| WO | 2020097531 | 5/2020 |

OTHER PUBLICATIONS

Cistrone, et al. "Click-Based Libraries of SFTI-1 Peptides: New Methods Using Reversed-Phase Silica", ACS Comb. Sci., 18(3):139-143 (2016).
Claverie, et al., "Information enhancement methods for large scale sequence analysis", Claverie Comput. Chem. 17:191-201 (1993).
Das, et al., "A General Synthetic Approach for Designing Epitope Targeted Macrocyclic Peptide Ligands", Angew. Chemie Int. Ed., 54 (45), 13219-13224 (2015).
Edelman, et al., "Extracranial carotid arteries: evaluation with 'black blood' MR angiography", Radiology, 177: 45-50 (1990).
Farrow, et al., "Epitope-Targeting of Tertiary Protein Structure Enables Target-Guided Synthesis of a Potent in Cell Inhibitor of Botulinum Neurotoxin", Angew. Chemie Int. Ed., 54 (24), 7114-7119 (2015).
Goodrich, et al., "A Quantitative Study of ramped Radio Frequency, Magnetization Transfer, and Slab Thickness in Three-Dimensional Time-of-Flight Magnetic Resonance Angiogrpahy in a Patient Population", Invest. Radia, 31: 323-32 (1996).
Iegre, et al., "Two-Component Stapling of Biological Active and Conformationally Constrained Peptides: Past, present, and Future", Adv. Therap., 1:1800052 (2018).
Lam, et al., "A new type of synthetic peptide library for identifying ligand-binding activity", Nature 354:83 (1991).
Manetsch, et al., "In Situ Click Chemistry: Enzyme Inhibitors Made to Their Own Specifications", J. Am. Chem. Soc. 126(40):12809-12818 (2004).
Mocharla, et al., "In Situ Click Chemistry: Enzyme Generated Inhibitors of Carbonic Anhydrase II", Angew. Chem. Int. Ed. Engl. 44:116 (2004).
Murray, et al., "The consequences of translational and rotational entropy lost by small molecules on binding to proteins", J. Comput. Aided. Mol. Des. 16:741 (2002).
Myers, et al., "Optimal alignments in linear space", Computer Applic. Biol. Sci. 4(1):11-17 (1988).
Shuker, et al., "Discovering High-Affinity Ligands for Proteins: SAR by NMR", Science, 274:1531 (1996).
Wells, "Site-directed ligand discovery", Proc. Natl. Acad. Sci. USA 97:9367 (2000).
Whiting, et al., "Inhibitors of HIV□1 Protease by Using In Situ Click Chemistry", Angew. Chem. Int. Ed. Engl. 45:1435 (2006).
Wooton, et al., "Statistics of Local Complexity in Amino Acid Sequences and Sequence Databases", Comput. Chem. 17(2):149-63 (1993).
International Search Report for corresponding PCT application PCT/US2019/059690 dated Feb. 21, 2020.
Claverie, "Information enhancement methods for large scaled sequence analysis", *Comput. Chem.*, 17:191-201 (1993).
Goodrich, et al., "A quantitative study of ramped radio frequency, magnetization transfer, and slab thickness in three-dimensional time-of-flight magnetic resonance angiography in a patient population", *Invest. Radia.*, 31: 323-32 (1996).
Lam, et al., "A new type of synthetic peptide library for identifying ligand-binding activity", *Nature*, 354:82-84 (1991).
Mocharla, et al., "In Situ Click Chemistry: Enzyme-Generated Inhibitors of Carbonic Anhydrase II", *Angew. Chem. Int. Ed. Engl.*, 44(1):116-120 (2004).
Murray, et al., "The consequences of translational and rotational entropy lost by small molecules on binding to proteins", *J. Comput. Aided. Mol. Des.*, 16:741-753 (2002).
Shuker, et al., Discovering High-Affinity Ligands for Proteins: SAR by NMR *Science*, 274(5292):1531-1534 (1996).
Wells, et al. "Site-directed ligand discovery", *PNAS*, 97:9367-9372 (2000).
Agnew, et al., "Protein-Catalyzed Capture Agents", Chemical Reviews, 119(17):9950-9970 (2019).
Bendre, et al., "Evaluation of Met-Val-Lys as a Renal Brush Border Enzyme-Cleavable Linker to Reduce Kidney Uptake of 68Ga-Labeled DOTA-Conjugated Peptides and Peptidomimetics", MOLECULES, 25(3854):1-21 (2020).
Bioatla, "Antibody Structure". www.bioatla.com, obtained Oct. 7, 2022.
Brown, et al., "Stapled Peptides with Improved Potency and Specificity That Activate p53", ACS Chemical Biology, 8(3):506-512 (2013).
Cantel, et al., "Synthesis and Conformational Analysis of a Cyclic Peptide Obtained via i to i +4 Intramolecular Side-Chain to side-Chain Azide-Alkyne 1,3-Dipolar Cycloaddition", The Journal of Organic Chemistry, 73(15):5663-5674 (2008).
Cochrane, et al., "Investigation of the ring-closing metathesis of peptides in water", Organic & Biomolecular Chemistry, 11(4):630 (2013).
Empting, et al., "Triazole Bridge: Disulfide-Bond Replacement by ruthenium-Catalyzed Formation of 1,5-Disubstituted 1,2,3-Triazoles", Angewandte Chemie International Edition, 50(22):5207-5211 (2011).
Isaad, et al., "Side Chain-To-Side Chain Cyclization by Click Reaction", Journal of Peptide Science, 15:451-454 (2009).
Joo, et al., "Cyclic Peptides as Therapeutic Agents and Biochemical Tools", Biomol. ther., 20(1):19-26 (2012).
Liu, et al., "Design and radio-synthesis of somatostatin receptors targeted 68Ga-DOTA-Benereotide for non-invasive PET imaging", J. Radioanal Nucl Chem, 307:1069-1075 (2015).
Malm, et al., "Engineering of a bispecific affibody molecule towards HER2 and HER3 by addition of an albumin-binding domain allows for affinity purification and in vivo half-life extension", Biotechnol. J., 9(9):1215-1222 (2014).
Nayak, et al. "86Y based PET radiopharmaceuticals: radiochemistry and biological applications", Med Chem., 7(5): 380-388 (2011).
Niida, et al., "Investigation of the structural requirements of K-Ras(G12D) selective inhibitory peptide KRpep-2d using alanine scans and cysteine bridging", Bioorganic & Medicinal Chemistry Letters, 27(12):2757-2761 (2017).
Oh, et al., "Amphilic Bicyclic Peptides as cellular Delivery Agents", ChemMedChem, 9(11):2449-2453 (2014).
Punna, et al., "Head-to-tail peptide cyclodimerization by copper-catalyzed azide-alkyne cycloaddition", Angewandte Chemie International Edition, 44(15):2215-2220 (2005).

(56) References Cited

OTHER PUBLICATIONS

Sakamoto, et al., "Generation of KS-58 as the first K-Ras (G12D)—inhibitory peptide presenting anti-cancer activity in vivo", Scientific Reports, 10(21671), 16 pages (2020).

Scrima, et al., "Cu I-Catalyzed Azide Alkyne Intramolecular i-to-(i+4) ide-Chain-to-Side-Chain Cyclization Promotes the Formation of Helix-Like Secondary Structures", European Journal of Organic Chemistry, 2010(3):446-457 (2010).

Suzuki, et al., "Preferential Cleavage of a Tripeptide Linkage by Enzymes on Renal Brush Border Membrane To Reduce Renal Radioactivity Levels of Radiolabeled Antibody Fragments", Journal of Medicinal Chemistry., 61(12):5257-5268 (2018).

Tal-Gan, et al., "Backbone Cyclic Peptide Inhibitors of Protein Kinase B (PKB/Akt)", journal of Medicinal Chemistry, American Chemical Society, 54(14):5154-5164 (2011).

Uehara, et al. "A Gallium-67/68-Labeled Antibody Fragment for Immuno-SPECT/PET Shows Low Renal Radioactivity Without Loss of Tumor Uptake", Clinical Cancer Research, 2018, 3309-3316 (Year: 2018).

Wu, et al., "Inhibition of Ras-effector interactions by cyclic peptidest", MedChemComm, 4(2):378-382 (2012).

Zealand Pharma ('What are Peptides?', https://www.zealandpharma.com/what-are-peptides which was accessed on Jan. 29, 2021) (Year: 2021).

Zhang, et al., "GTP-State-Selective Cyclic Peptide Ligands of K_Ras(G12D)Block Its Interaction with Raf", ACS Central Science, 6(10):1753-1761 (2020).

* cited by examiner

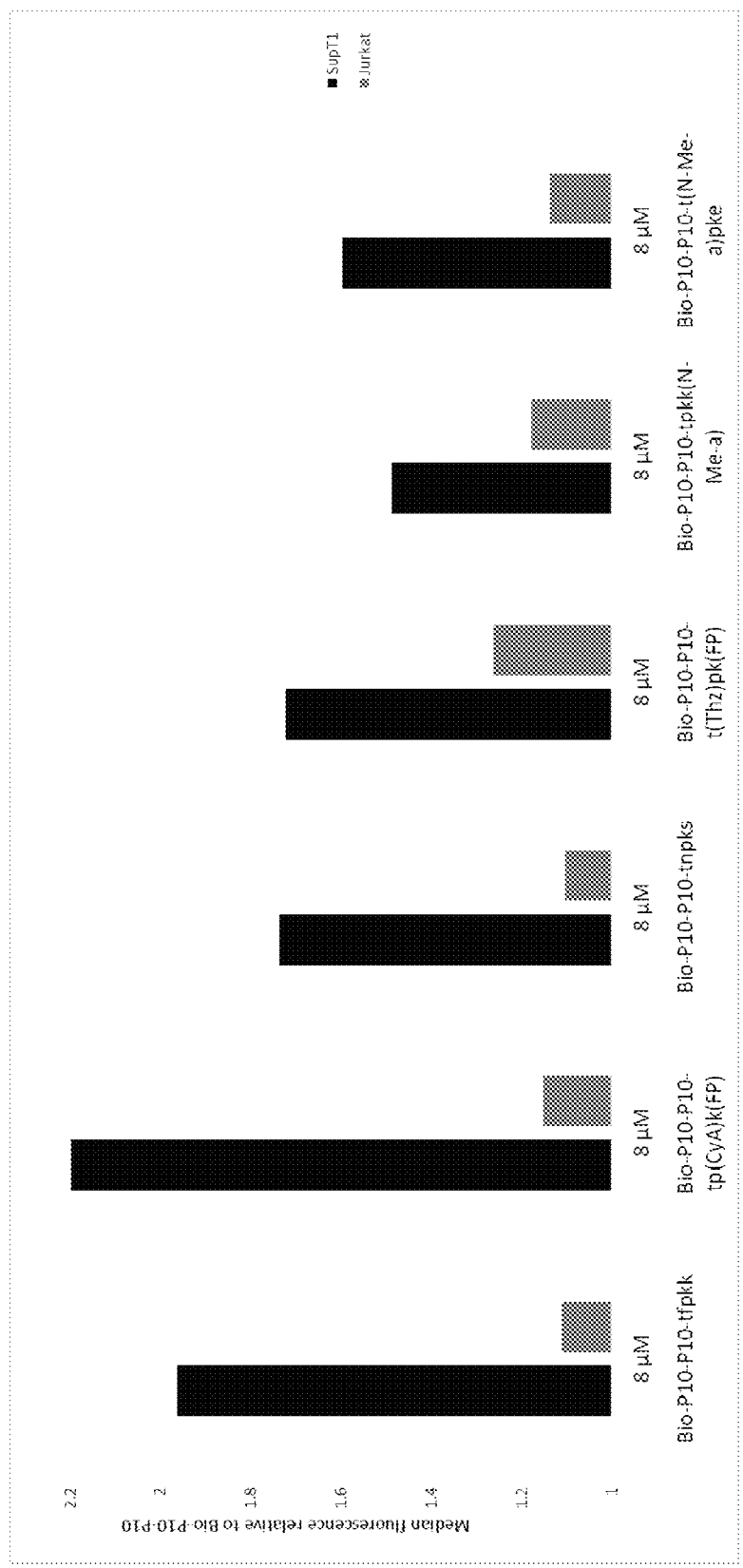

PEPTIDE LIBRARIES WITH NON-CANONICAL AMINO ACIDS

CROSS-REFERENCE TO RELATED APPLICATIONS

This application claims benefit of U.S. Provisional Application No. 62/755,403, filed Nov. 2, 2018. Application No. 62/755,403, filed Nov. 2, 2018, is hereby incorporated herein by reference in its entirety.

FIELD OF THE INVENTION

The disclosed invention is generally in the field of peptide libraries and specifically in the area of peptide libraries for design and selection of protein binding agents.

BACKGROUND OF THE INVENTION

Detection of disease at the earliest stages requires multiplex measurements of key protein biomarkers in biological samples. The availability of high-affinity, highly selective compositions that recognize biomarkers from complex biological mixtures is a critical component for accurate detection of proteins that may indicate disease or changes in health. Peptide affinity agents have been suggested for use as agents for in vitro and/or in vivo detection of disease causing proteins.

Peptide affinity agents that bind to various targets (e.g. proteins) may be identified by screening large peptide libraries, and then using various techniques to identify which peptide library elements exhibit the desired interaction with the target. Those peptide libraries may be biologically synthesized (e.g. bacterial or viral phage display), or they may be chemically synthesized (e.g. one-bead-one-compound (OBOC) libraries). For chemically synthesized libraries, a candidate peptide binder is often first identified using a chemical label. For example, if a protein binds to a particular peptide sequence on a particular bead, then labeling that protein with a fluorescent molecule, or using a similarly labeled antibody to detect the bead-bound protein, can be used to identify the bead that contains the peptide of interest.

Regardless of their preparation method, the sequence of the peptide of interest must then be determined. Typical methods for determining that sequence include mass spectrometric sequencing, or Edman degradation. Thus, peptide libraries for identification of protein affinity agents are preferably readily sequenceable by common techniques.

The scope of amino acids, and thus of the physical and chemical space of the peptides, has generally been limited to the natural amino acids. A broader or different scope of physical and chemical properties of peptides could provide additional or better protein targeting peptides.

Accordingly, there is a need for improved protein targeting peptides. In particular, there is a need for peptides having a broader or different scope of physical and chemical properties. The present invention fulfills this need and provides further related advantages.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

BRIEF SUMMARY OF THE INVENTION

Disclosed are peptides and libraries of peptides comprising amino acids selected from a set of amino acids that includes both canonical and non-canonical amino acids. In some forms, the amino acid set can include two or more amino acids from each of the categories (a) hydrophobic side chain—aliphatic, (b) hydrophobic side chain—aromatic, (c) polar side chain—neutral, (d) polar side chain—charged, and (e) conformational perturbation.

In some forms, the amino acid set can include two or more amino acids from each of the categories (a) hydrophobic side chain—aliphatic, (b) hydrophobic side chain—aromatic, (c) polar side chain—neutral, and (d) polar side chain—charged, and can include one or more amino acids from the conformational perturbation category.

In some forms, the amino acid set can comprise 10, 11, 12, 13, 14, 15, 16, 17, 18, 19, 20, 21, 22, 23, 24, 25, or 26 different amino acids. In some forms, the amino acid set can consist of 10, 11, 12, 13, 14, 15, 16, 17, 18, 19, 20, 21, 22, 23, 24, 25, or 26 different amino acids.

In some forms, the amino acid set can comprise 1, 2, 3, 4, 5, 6, 7, 8, 9, 10, 11, 12, 13, 14, 15, 16, 17, 18, 19, 20, 21, 22, 23, 24, 25, or 26 different non-canonical amino acids.

In some forms, the amino acid set can comprise 1, 2, 3, 4, 5, 6, 7, 8, 9, 10, 11, 12, 13, 14, 15, 16, 17, 18, 19, or 20 different canonical amino acids.

In some forms, the amino acid set can comprise any combination of canonical amino acids and non-canonical amino acids, wherein at least 1, 2, 3, 4, 5, 6, 7, 8, 9, 10, 11, 12, 13, 14, 15, 16, 17, 18, 19, or 20 of the amino acids in the amino acid set is a non-canonical amino acid and at least 1, 2, 3, 4, 5, 6, 7, 8, 9, 10, 11, 12, 13, 14, 15, 16, 17, 18, 19, or 20 of the amino acids in the amino acid set is a canonical amino acid, and wherein the set of amino acids totals 10, 11, 12, 13, 14, 15, 16, 17, 18, 19, 20, 21, 22, 23, 24, 25, or 26 different amino acids.

In some forms, the amino acid set can consist of any combination of canonical amino acids and non-canonical amino acids, wherein at least 1, 2, 3, 4, 5, 6, 7, 8, 9, 10, 11, 12, 13, 14, 15, 16, 17, 18, 19, or 20 of the amino acids in the amino acid set is a non-canonical amino acid and at least 1, 2, 3, 4, 5, 6, 7, 8, 9, 10, 11, 12, 13, 14, 15, 16, 17, 18, 19, or 20 of the amino acids in the amino acid set is a canonical amino acid, and wherein the set of amino acids totals 10, 11, 12, 13, 14, 15, 16, 17, 18, 19, 20, 21, 22, 23, 24, 25, or 26 different amino acids.

Preferably, the disclosed peptides are cyclic peptides having activity as protein affinity agents, including stereoisomers, pharmaceutically acceptable salts and prodrugs thereof, and methods for identification and use of the same. Advantageously, embodiments of the cyclic peptides described herein can be prepared from natural and/or non-natural amino acids (i.e., canonical and/or non-canonical amino acids) using common solid-state peptide synthesis techniques and can be readily sequenced. In various embodiments, the cyclic peptides comprise a variable region (VR) and constant region (CR). The variable region generally comprises a peptide sequence which varies among peptides in a library, thus providing a means for identifying a sequence having affinity for a desired target, such as a protein epitope. The constant region, in various embodiments, comprises functionality to aid in the screening process, such as: chemical groups that aid in sequencing, chemical groups that provide handles for various assays, chemical groups that are important for closing the peptide into a cycle (e.g., triazole, carbon-carbon double bonds), chemical groups that provide additional biochemical or chemical properties (stability, cell wall penetration, etc.) reporter groups (e.g., bimolecular labels such as biotin) and/or other useful chemical moieties. In certain embodiments, the CR comprises an exocyclic amine group which provides a means for sequencing the peptides via standard Edman degradation.

In some forms, the peptide is a cyclic peptide having the following structure (I):

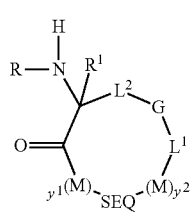

(I)

or a salt, tautomer, prodrug or stereoisomer thereof, wherein R, $R^1$, $L^1$, $L^2$, G, M, $Y^1$ $Y^2$ and SEQ are as defined herein. In particular, disclosed are such peptides having one or more non-canonical amino acids in SEQ. Compositions comprising the cyclic peptide structure (I) and libraries comprising a plurality of the cyclic peptides are also provided in other embodiments.

In another embodiment, a method for identifying a target binding agent compound is also provided, the method comprising:
  A) providing a first peptide library comprising a plurality of first peptide library members, the first peptide library members optionally comprising an alkyne, azide or reporter moiety or combinations thereof;
  B) contacting the first peptide library with a target or a truncated analogue thereof, the target or truncated analogue thereof comprising a first binding site and optionally an alkyne, azide or reporter moiety or combinations thereof;
  C) identifying a first peptide library member with affinity for the first binding site and optionally modifying the first peptide library member to include an alkyne or azide moiety;
and optionally:
  D) providing a second peptide library comprising a plurality of second peptide library members, the second peptide library members comprising an azide or alkyne or both;
  E) contacting the second peptide library with a composition comprising the target or truncated analogue thereof and the first peptide library member of step C;
  F) forming a triazole-linked conjugate between the first peptide library member of step C and a second peptide library member, the second peptide library member having affinity for a second binding site on the target or truncated analogue thereof,
  wherein the first peptide library, the second peptide library, or both, comprise cyclic peptides comprising:

i. a sequence region comprising amino and carboxy termini and a variable peptide sequence of two to twenty amino acids selected from natural and non-natural amino acids; and
  ii. a linker region comprising a α-amino carbonyl, α-amido carbonyl, a methionine amino acid, or combinations thereof, and optionally comprising an alkyne, an azide, a linkage to a solid support or a linkage to a reporter moiety or a combination thereof, the linker region covalently linking the amino and carboxy termini of the sequence region.

A preferred set of amino acids from which the amino acids of SEQ can be selected (Set 1) contains Cyclopropyl Alanine (CyA) and Gly (hydrophobic side chain—aliphatic); 4-Fluorophenyl Alanine (FP), Methyl Tryptophan (MT), 2-Methoxy Pyridylalanine (MeOPyr), and 4-Phenyl Phenylalanine (PhF) (hydrophobic side chain—aromatic); Asn, Ser, Thr (polar side chain—neutral); His, Lys, Arg, Glu (polar side chain—charged); and β-Phenylalanine (BPhA), N-Methyl d-alanine (N-Me-a), and Pro (conformational perturbation).

Another preferred set of amino acids from which the amino acids of SEQ can be selected (Set 2) contains Cyclopropyl Alanine (CyA) and Gly (hydrophobic side chain—aliphatic); 4-Fluorophenyl Alanine (FP), Methyl Tryptophan (MT), Thiazolyl Alanine (Thz), 4-Phenyl Phenylalanine (PhF), and Phe (hydrophobic side chain—aromatic); Asn, Ser, Thr (polar side chain—neutral); His, Lys, Arg, Glu (polar side chain—charged); and N-Methyl d-alanine (N-Me-a), and Pro (conformational perturbation).

Another preferred set of amino acids from which the amino acids of SEQ can be selected (Set 3) contains Cyclopropyl Alanine (CyA) and Gly (hydrophobic side chain—aliphatic); 4-Fluorophenyl Alanine (FP), Methyl Tryptophan (MT), 2-Methoxy Pyridylalanine (MeOPyr), Thiazolyl Alanine (Thz), 4-Phenyl Phenylalanine (PhF), and Phe (hydrophobic side chain—aromatic); Asn, Ser, Thr (polar side chain—neutral); His, Lys, Arg, Glu (polar side chain—charged); and β-Phenylalanine (BPhA), N-Methyl d-alanine (N-Me-a), and Pro (conformational perturbation).

In some forms, SEQ can comprise t(Thz)pk(FP), t(PhF)Gk(FP), t(Thz)hkn (SEQ ID NO:2), t(Thz)(FP)kG, tG(PhF)k(N-Me-a), t(CyA)(PhF)kh, t(CyA)(FP)kn, t(N-Me-a)(N-Me-a)kn, t(N-Me-a)pke (SEQ ID NO:3), tphkn (SEQ ID NO:4), t(CyA)rks (SEQ ID NO:5), tpkk(N-Me-a) (SEQ ID NO:6), t(CyA)ek(N-Me-a), t(CyA)ekh (SEQ ID NO:7), t(CyA)tk(CyA), tesk(CyA) (SEQ ID NO:8), tetk(N-Me-a) (SEQ ID NO:9), tenk(FP) (SEQ ID NO:10), tekkp (SEQ ID NO:11), tskk(N-Me-a) (SEQ ID NO:12), ttrk (SEQ ID NO:13), tnkk(CyA) (SEQ ID NO:14), ts(Thz)k(CyA), tk(FP)kk (SEQ ID NO:15), trrk(CyA) (SEQ ID NO:16), trrks (SEQ ID NO:17), tkrkr (SEQ ID NO:18), trkkh (SEQ ID NO:19), trnkr (SEQ ID NO:20), ttkkr (SEQ ID NO:21), tshkr (SEQ ID NO:22), t(Thz)rkk (SEQ ID NO:23), tr(Thz)kr (SEQ ID NO:24), tr(FP)kr (SEQ ID NO:25), tk(FP)kr (SEQ ID NO:26), trGkr (SEQ ID NO:27), tG(CyA)kr (SEQ ID NO:28), tp(CyA)k(FP), te(MT)kp (SEQ ID NO:29), tnpks (SEQ ID NO:31), tp(CyA)k(FP), t(CyA/e/Thz)(k/FP)k(N-Me-a/n/FP), or trrkr (SEQ ID NO:30).

In various other embodiments, uses of the cyclic peptides and methods employing the same are provided.

Also disclosed are improved methods for analyzing and assessing epitopes as potential targets for ligands and protein targeting agents.

Additional advantages of the disclosed method and compositions will be set forth in part in the description which follows, and in part will be understood from the description, or can be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWING

FIG. 1 is a graph binding of some example peptides to CD8+ cells (SuppT1 cells) and CD8− cells (Jurkat cells).

DETAILED DESCRIPTION OF THE INVENTION

The disclosed method and compositions can be understood more readily by reference to the following detailed description of particular embodiments and the Example included therein and to the Figures and their previous and following description.

Incorporating non-canonical (unnatural) amino acids can greatly increase the chemical diversity of one bead one compound libraries. Preferred non-canonical amino acids have unique properties that differ substantially from the canonical 20 amino acids. These new amino acids incorporate (but are not limited to) heterocycles, halogen-substituted arenes, carbocycles, beta amino acids, and N-methylation. Several of these structures are considered "privileged scaffolds" of medicinal chemistry, moieties that often appear in bioactive compounds. The substitution also decreases the intrinsic metabolic liabilities of several natural amino acids. The inclusion of beta amino acids increases the flexibility of the macrocycle, and incorporation of N-Methylated amino acids increases the propensity of the amine bond to adopt a cis-geometry.

The standard 16 amino acid set (i.e., using canonical amino acids) contains Ala, Gly, Leu, and Val (hydrophobic side chain—aliphatic); Phe, Tyr, and Trp (hydrophobic side chain—aromatic); Asn, Ser, and Thr (polar side chain—neutral); His, Lys, Arg, and Glu (polar side chain—charged); and Pro (conformational perturbation). The canonical amino acids left out of this set are Ile, Gln, Cys, and Met.

Hydrophobic Side Chain - Aliphatic

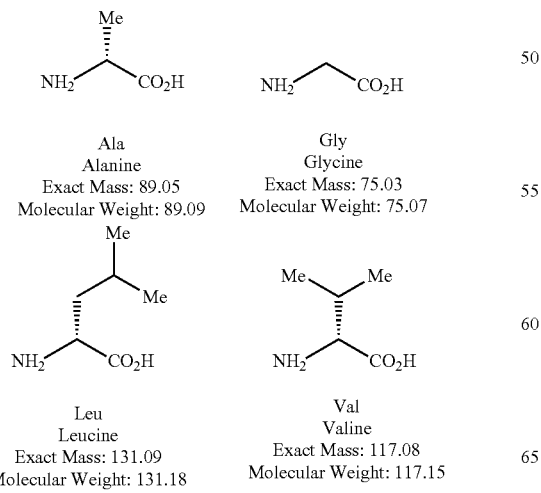

Ala
Alanine
Exact Mass: 89.05
Molecular Weight: 89.09

Gly
Glycine
Exact Mass: 75.03
Molecular Weight: 75.07

Leu
Leucine
Exact Mass: 131.09
Molecular Weight: 131.18

Val
Valine
Exact Mass: 117.08
Molecular Weight: 117.15

-continued

Hydrophobic Side Chain - Aromatic

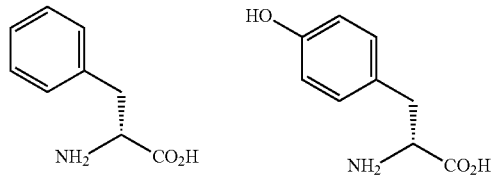

Phe
Phenyl alanine
Exact Mass: 165.08
Molecular Weight: 165.19

Tyr
Tyrosine
Exact Mass: 181.07
Molecular Weight: 181.19

Trp
Tryptophan
Exact Mass: 204.09
Molecular Weight: 204.23

Polar Side Chain - Neutral

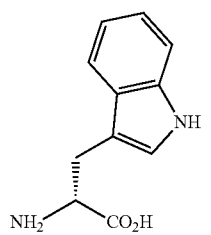

Asn
Asparagine
Exact Mass: 132.05
Molecular Weight: 132.12

Ser
Serine
Exact Mass: 105.04
Molecular Weight: 105.09

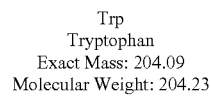

Thr
Threonine
Exact Mass: 119.06
Molecular Weight: 119.12

Polar Side Chain - Charged

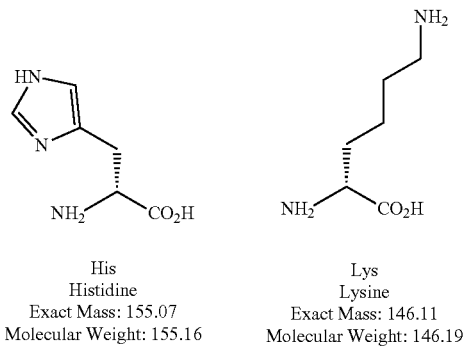

His
Histidine
Exact Mass: 155.07
Molecular Weight: 155.16

Lys
Lysine
Exact Mass: 146.11
Molecular Weight: 146.19

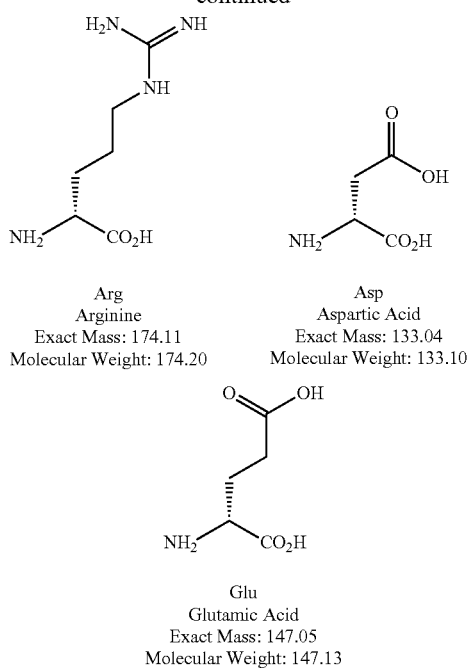

Arg
Arginine
Exact Mass: 174.11
Molecular Weight: 174.20

Asp
Aspartic Acid
Exact Mass: 133.04
Molecular Weight: 133.10

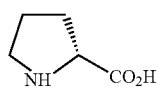

Glu
Glutamic Acid
Exact Mass: 147.05
Molecular Weight: 147.13

Conformational Perturbation

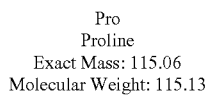

Pro
Proline
Exact Mass: 115.06
Molecular Weight: 115.13

One preferred non-canonical 16 amino acid set (i.e., including non-canonical amino acids) (Set 1) contains Cyclopropyl Alanine (CyA) and Gly (hydrophobic side chain—aliphatic); 4-Fluorophenyl Alanine (FP), Methyl Tryptophan (MT), 2-Methoxy Pyridylalanine (MeOPyr), and 4-Phenyl Phenylalanine (PhF) (hydrophobic side chain—aromatic); Asn, Ser, Thr (polar side chain—neutral); His, Lys, Arg, Glu (polar side chain—charged); and 0-Phenylalanine (BPhA), N-Methyl d-alanine (N-Me-a), and Pro (conformational perturbation). The canonical amino acids left out of this set are Ala, Ile, Leu, Val, Phe, Tyr, Trp, Asp, Gln, Cys, and Met.

Hydrophobic Side Chain - Aliphatic

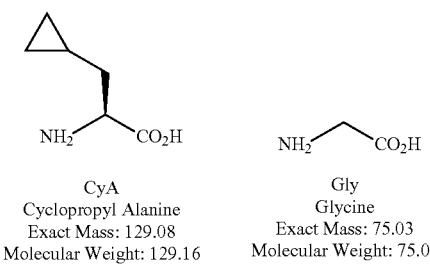

CyA
Cyclopropyl Alanine
Exact Mass: 129.08
Molecular Weight: 129.16

Gly
Glycine
Exact Mass: 75.03
Molecular Weight: 75.07

Hydrophobic Side Chain - Aromatic

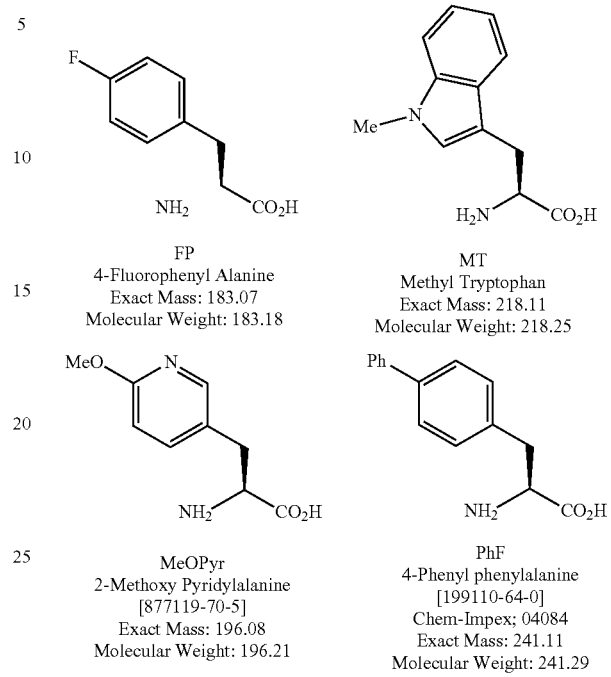

FP
4-Fluorophenyl Alanine
Exact Mass: 183.07
Molecular Weight: 183.18

MT
Methyl Tryptophan
Exact Mass: 218.11
Molecular Weight: 218.25

MeOPyr
2-Methoxy Pyridylalanine
[877119-70-5]
Exact Mass: 196.08
Molecular Weight: 196.21

PhF
4-Phenyl phenylalanine
[199110-64-0]
Chem-Impex; 04084
Exact Mass: 241.11
Molecular Weight: 241.29

Polar Side Chain - Neutral

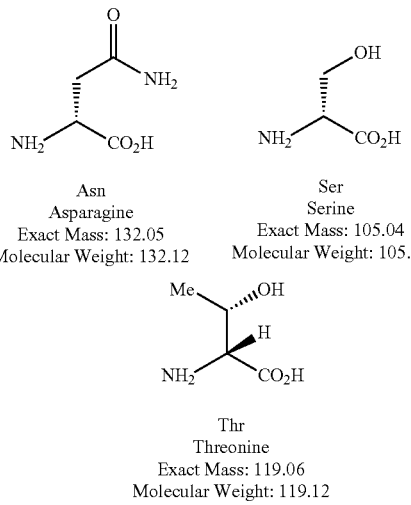

Asn
Asparagine
Exact Mass: 132.05
Molecular Weight: 132.12

Ser
Serine
Exact Mass: 105.04
Molecular Weight: 105.09

Thr
Threonine
Exact Mass: 119.06
Molecular Weight: 119.12

Polar Side Chain - Charged

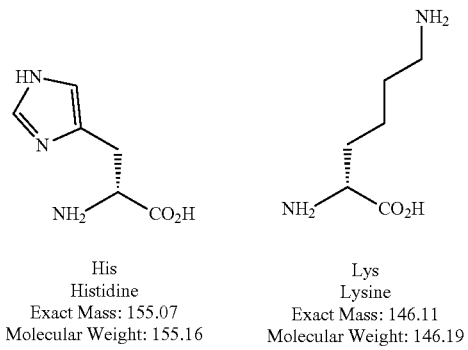

His
Histidine
Exact Mass: 155.07
Molecular Weight: 155.16

Lys
Lysine
Exact Mass: 146.11
Molecular Weight: 146.19

-continued

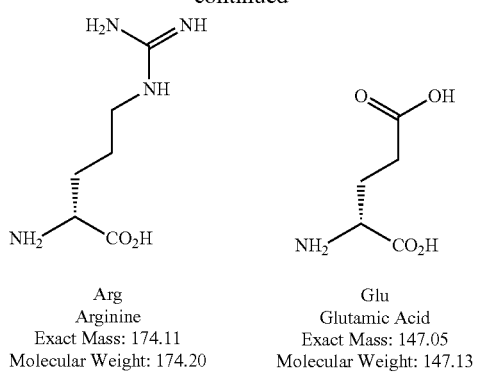

Arg
Arginine
Exact Mass: 174.11
Molecular Weight: 174.20

Glu
Glutamic Acid
Exact Mass: 147.05
Molecular Weight: 147.13

Conformational Perturbation

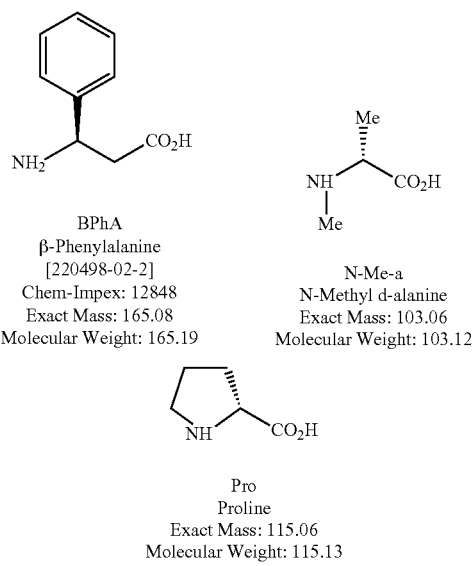

BPhA
β-Phenylalanine
[220498-02-2]
Chem-Impex: 12848
Exact Mass: 165.08
Molecular Weight: 165.19

N-Me-a
N-Methyl d-alanine
Exact Mass: 103.06
Molecular Weight: 103.12

Pro
Proline
Exact Mass: 115.06
Molecular Weight: 115.13

Another preferred non-canonical 16 amino acid set (i.e., including non-canonical amino acids) (Set 2) contains Cyclopropyl Alanine (CyA) and Gly (hydrophobic side chain—aliphatic); 4-Fluorophenyl Alanine (FP), Methyl Tryptophan (MT), Thiazolyl Alanine (Thz), 4-Phenyl Phenylalanine (PhF), and Phe (hydrophobic side chain—aromatic); Asn, Ser, Thr (polar side chain—neutral); His, Lys, Arg, Glu (polar side chain—charged); and N-Methyl d-alanine (N-Me-a), and Pro (conformational perturbation). The canonical amino acids left out of this set are Ala, Ile, Leu, Val, Tyr, Trp, Asp, Gln, Cys, and Met.

Hydrophobic Side Chain - Aliphatic

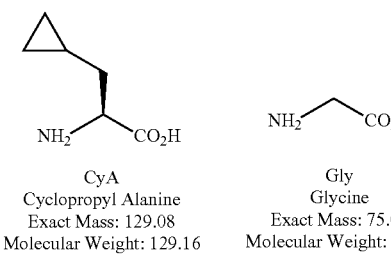

CyA
Cyclopropyl Alanine
Exact Mass: 129.08
Molecular Weight: 129.16

Gly
Glycine
Exact Mass: 75.03
Molecular Weight: 75.07

-continued

Hydrophobic Side Chain - Aromatic

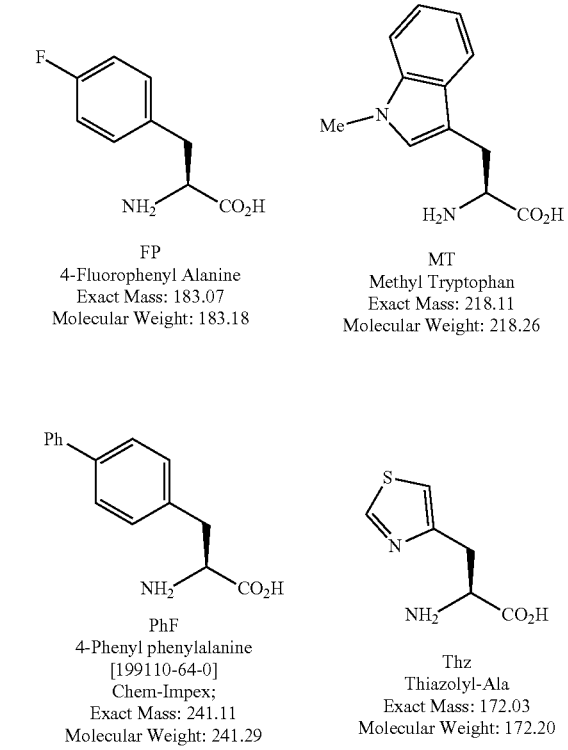

FP
4-Fluorophenyl Alanine
Exact Mass: 183.07
Molecular Weight: 183.18

MT
Methyl Tryptophan
Exact Mass: 218.11
Molecular Weight: 218.26

PhF
4-Phenyl phenylalanine
[199110-64-0]
Chem-Impex;
Exact Mass: 241.11
Molecular Weight: 241.29

Thz
Thiazolyl-Ala
Exact Mass: 172.03
Molecular Weight: 172.20

Phe
Phenyl alanine
Exact Mass: 165.08
Molecular Weight: 165.19

Polar Side Chain - Neutral

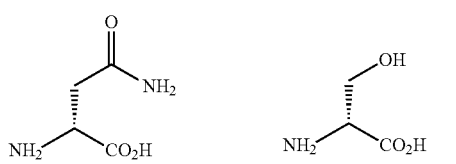

Asn
Asparagine
Exact Mass: 132.05
Molecular Weight: 132.12

Ser
Serine
Exact Mass: 105.04
Molecular Weight: 105.09

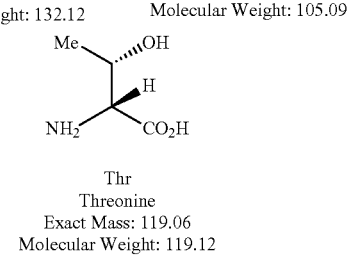

Thr
Threonine
Exact Mass: 119.06
Molecular Weight: 119.12

-continued
Polar Side Chain - Charged

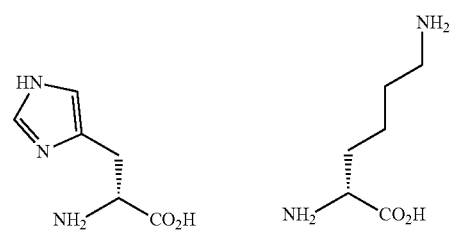

His
Histidine
Exact Mass: 155.07
Molecular Weight: 155.16

Lys
Lysine
Exact Mass: 146.11
Molecular Weight: 146.19

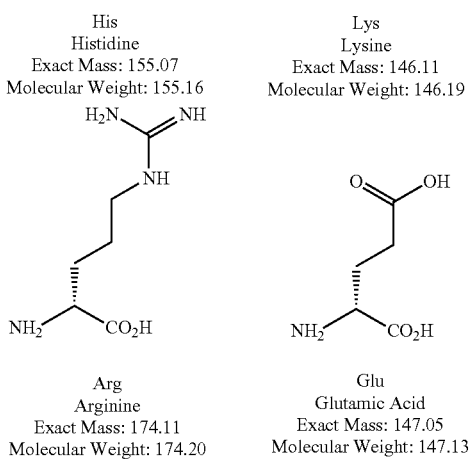

Arg
Arginine
Exact Mass: 174.11
Molecular Weight: 174.20

Glu
Glutamic Acid
Exact Mass: 147.05
Molecular Weight: 147.13

Conformational Perturbation

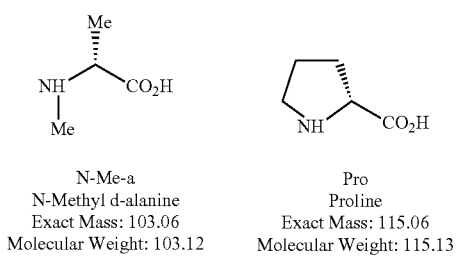

N-Me-a
N-Methyl d-alanine
Exact Mass: 103.06
Molecular Weight: 103.12

Pro
Proline
Exact Mass: 115.06
Molecular Weight: 115.13

Another preferred set of amino acids from which the amino acids of SEQ can be selected (Set 3) contains Cyclopropyl Alanine (CyA) and Gly (hydrophobic side chain—aliphatic); 4-Fluorophenyl Alanine (FP), Methyl Tryptophan (MT), 2-Methoxy Pyridylalanine (MeOPyr), Thiazolyl Alanine (Thz), 4-Phenyl Phenylalanine (PhF), and Phe (hydrophobic side chain—aromatic); Asn, Ser, Thr (polar side chain—neutral); His, Lys, Arg, Glu (polar side chain—charged); and β-Phenylalanine (BPhA), N-Methyl d-alanine (N-Me-a), and Pro (conformational perturbation)—the structures of which can be seen above.

In general, non-canonical amino acids that can be included in the disclosed amino acid sets can be selected from any one or combinations of Cyclopropyl Alanine (CyA), Methyl Leucine (MeL), Methyl Valine (MeV), Allylglycine, Methyl Tryptophan (MT), Thiazolyl Alanine (Thz), 2-Naphthyl Alanine (Nap), O-Methyl Tyrosine (OMY), 4-Fluorophenyl Alanine (FP), 4-Cyano Phenylalanine (CN—F), 4-Phenyl Phenylalanine (PhF), 4-Bromo Phenylalanine (Br—F), 4-Pyridyl Alanine (PyrA), 4-Methyl Phenylalanine (Me-F), O-Phenyl Tyrosine (OPhY), β-Phenylalanine (BPhA), Dimethyl Lysine (DMK), 2-Methoxy Pyridylalanine (MeOPyr), Piperazinecarboxylic acid, N-Methyl d-valine (N-Me-v), N-Methyl d-alanine (N-Me-a), Aminocyclobutyl carboxylic acid (ACBC), Aminocyclohexyl carboxylic (ACHC), α-Methyl Alanine (AMA), Morpholinecarboxylic acid, Tetrazoyl Alanine (Ttz), β-Alanine (BAla), and Azetidine carboxylic acid.

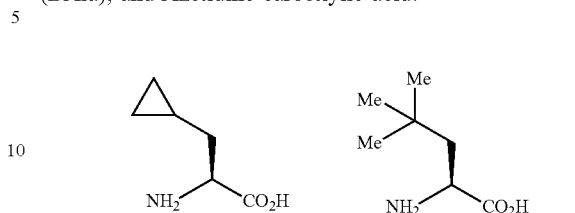

CyA
Cyclopropyl Alanine
Exact Mass: 129.08
Molecular Weight: 129.16

MeL
Methyl Leucine
Exact Mass: 145.11
Molecular Weight: 145.20

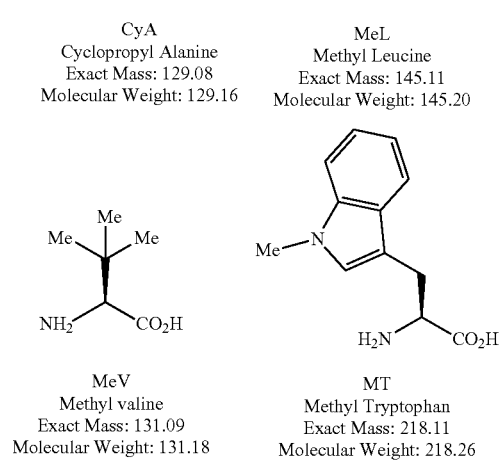

MeV
Methyl valine
Exact Mass: 131.09
Molecular Weight: 131.18

MT
Methyl Tryptophan
Exact Mass: 218.11
Molecular Weight: 218.26

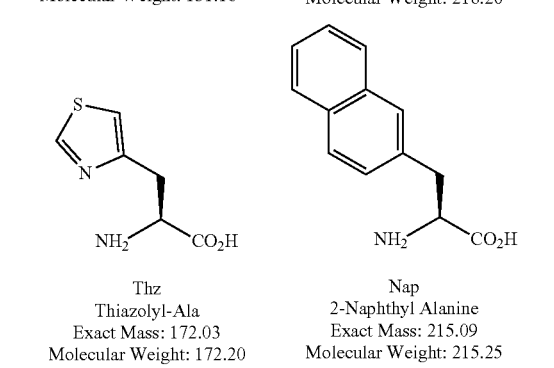

Thz
Thiazolyl-Ala
Exact Mass: 172.03
Molecular Weight: 172.20

Nap
2-Naphthyl Alanine
Exact Mass: 215.09
Molecular Weight: 215.25

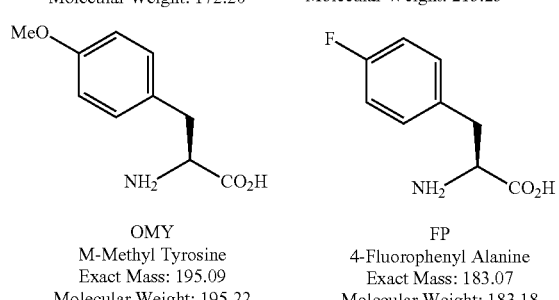

OMY
M-Methyl Tyrosine
Exact Mass: 195.09
Molecular Weight: 195.22

FP
4-Fluorophenyl Alanine
Exact Mass: 183.07
Molecular Weight: 183.18

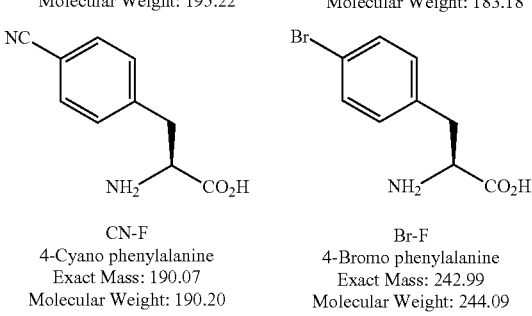

CN-F
4-Cyano phenylalanine
Exact Mass: 190.07
Molecular Weight: 190.20

Br-F
4-Bromo phenylalanine
Exact Mass: 242.99
Molecular Weight: 244.09

Me-F
4-Methyl phenylalanine
Exact Mass: 179.09
Molecular Weight: 179.22

OPhY
O-PhenylTyrosine
Exact Mass: 257.11
Molecular Weight: 257.29

BPhA
β-Phenylalanine
[220498-02-2]
Chem-Impex: 12848
Exact Mass: 165.08
Molecular Weight: 165.19

MeOPyr
2-Methoxy Pyridylalanine
[877119-70-5]
Exact Mass: 196.08
Molecular Weight: 195.21

PyrA
Pyridyl Alanine
Exact Mass: 166.07
Molecular Weight: 166.18

PhF
4-Phenyl phenylalanine
[199110-64-0]
Chem.-Impex; 04084
Exact Mass: 241.11
Molecular Weight: 241.29

Piperazinecarboxylic acid
[201047-84-9]
Molecular Weight: 130.15

AMA
alpha-Methylalanine
Exact Mass: 103.06
Molecular Weight: 103.12

Allylglycine
[16338-48-0]
Exact Mass: 115.06
Molecular Weight: 115.13

DMK
Dimethyl-Lys
Exact Mass: 174.14
Molecular Weight: 174.24

N-Me-a
N-Methyl d-alanine
Exact Mass: 103.06
Molecular Weight: 103.12

BAla
β-Alanine
Exact Mass: 89.05
Molecular Weight: 89.09

Ttz
Tetrazolyl Alanine
Exact Mass: 157.06
Molecular Weight: 157.13

N-Me-V
N-Methyl d-Valine
Exact Mass: 131.09
Molecular Weight: 131.18

Azetidine Carboxylic acid
[136552-06-2]
Molecular Weight: 101.11

Morpholinecarboxylic acid
[281655-37-6]
Molecular Weight: 131.13

ACBC
Aminocyclobutyl
carboxylic acid
Exact Mass: 115.06
Molecular Weight: 115.13

ACHC
Aminocyclohexyl
carboxylic acid
Exact Mass: 143.09
Molecular Weight: 143.19

In some forms, non-canonical amino acids that can be included in the disclosed amino acid sets can be selected from any one or combinations of Cyclopropyl Alanine (CyA), Methyl Leucine (MeL), Methyl Valine (MeV), Methyl Tryptophan (MT), Thiazolyl Alanine (Thz), 2-Naphthyl Alanine (Nap), O-Methyl Tyrosine (OMY), 4-Fluorophenyl Alanine (FP), 4-Cyano Phenylalanine (CN—F), 4-Phenyl Phenylalanine (PhF), 4-Bromo Phenylalanine (Br—F), 4-Pyridyl Alanine (PyrA), 4-Methyl Phenylalanine (Me-F), O-Phenyl Tyrosine (OPhY), β-Phenylalanine (BPhA), Dimethyl Lysine (DMK), N-Methyl d-valine (N-Me-v), N-Methyl d-alanine (N-Me-a), Aminocyclobutyl carboxylic acid (ACBC), Aminocyclohexyl carboxylic (ACHC), α-Methyl Alanine (AMA), Tetrazoyl Alanine (Ttz), and β-Alanine (BAla).

-continued

CyA
Cyclopropyl Alanine
Exact Mass: 129.08
Molecular Weight: 129.16

MeL
Methyl Leucine
Exact Mass: 145.11
Molecular Weight: 145.20

Me-F
4-Methyl phenylalanine
Exact Mass: 179.09
Molecular Weight: 179.22

OPhY
O-PhenylTyrosine
Exact Mass: 257.11
Molecular Weight: 257.29

MeV
Methyl valine
Exact Mass: 131.09
Molecular Weight: 131.18

MT
Methyl Tryptophan
Exact Mass: 218.11
Molecular Weight: 218.26

PyrA
Pyridyl Alanine
Exact Mass: 166.07
Molecular Weight: 166.18

PhF
4-Phenyl phenylalanine
[199110-64-0]
Chem.-Impex; 04084
Exact Mass: 241.11
Molecular Weight: 241.29

Thz
Thiazolyl-Ala
Exact Mass: 172.03
Molecular Weight: 172.20

Nap
2-Naphthyl Alanine
Exact Mass: 215.09
Molecular Weight: 215.25

DMK
Dimethyl-Lys
Exact Mass: 174.14
Molecular Weight: 174.24

Trz
Tetrazolyl Alanine
Exact Mass: 157.06
Molecular Weight: 157.13

OMY
M-Methyl Tyrosine
Exact Mass: 195.09
Molecular Weight: 195.22

FP
4-Fluorophenyl Alanine
Exact Mass: 183.07
Molecular Weight: 183.18

N-Me-v
N-Methyl d-Valine
Exact Mass: 131.09
Molecular Weight: 131.18

ACBC
Aminocyclobutyl
carboxylic acid
Exact Mass: 115.06
Molecular Weight: 115.13

CN-F
4-Cyano phenylalanine
Exact Mass: 190.07
Molecular Weight: 190.20

Br-F
4-Bromo phenylalanine
Exact Mass: 242.99
Molecular Weight: 244.09

ACHC
Aminocyclohexyl
carboxylic acid
Exact Mass: 143.09
Molecular Weight: 143.19

BPhA
β-Phenylalanine
[220498-02-2]
Chem-Impex; 12848
Exact Mass: 165.08
Molecular Weight: 165.19

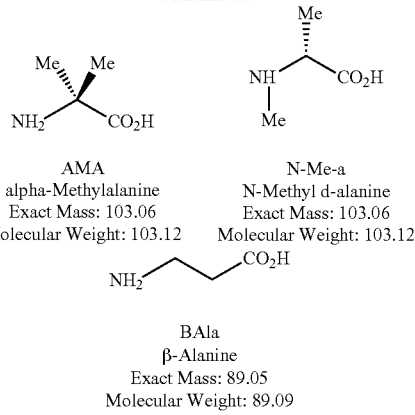

AMA
alpha-Methylalanine
Exact Mass: 103.06
Molecular Weight: 103.12

N-Me-a
N-Methyl d-alanine
Exact Mass: 103.06
Molecular Weight: 103.12

BAla
β-Alanine
Exact Mass: 89.05
Molecular Weight: 89.09

The non-canonical amino acids generally fall in the following categories:
Hydrophobic side chain—aliphatic: CyA, MeL, MeV, and allylglycine;
Hydrophobic side chain—aromatic: FP, MT, MeOPyr, PhF, Nap, OMY, CN—F, Br—F, PyrA, Me-F, OPhY; and
Conformational perturbation: BPhA, N-Me-a, and N-Me-v.

In some forms, the amino acid set can include two or more amino acids from each of the categories (a) hydrophobic side chain—aliphatic, (b) hydrophobic side chain—aromatic, (c) polar side chain—neutral, (d) polar side chain—charged, and (e) conformational perturbation.

In some forms, the amino acid set can include two or more amino acids from each of the categories (a) hydrophobic side chain—aliphatic, (b) hydrophobic side chain—aromatic, (c) polar side chain—neutral, and (d) polar side chain—charged, and can include one or more amino acids from the conformational perturbation category.

In some forms, the amino acid set can comprise 10, 11, 12, 13, 14, 15, 16, 17, 18, 19, 20, 21, 22, 23, 24, 25, or 26 different amino acids. In some forms, the amino acid set can consist of 10, 11, 12, 13, 14, 15, 16, 17, 18, 19, 20, 21, 22, 23, 24, 25, or 26 different amino acids.

In some forms, the amino acid set can comprise 1, 2, 3, 4, 5, 6, 7, 8, 9, 10, 11, 12, 13, 14, 15, 16, 17, 18, 19, 20, 21, 22, 23, 24, 25, or 26 different non-canonical amino acids.

In some forms, the amino acid set can comprise 1, 2, 3, 4, 5, 6, 7, 8, 9, 10, 11, 12, 13, 14, 15, 16, 17, 18, 19, or 20 different canonical amino acids.

In some forms, the amino acid set can comprise any combination of canonical amino acids and non-canonical amino acids, wherein at least 1, 2, 3, 4, 5, 6, 7, 8, 9, 10, 11, 12, 13, 14, 15, 16, 17, 18, 19, or 20 of the amino acids in the amino acid set is a non-canonical amino acid and at least 1, 2, 3, 4, 5, 6, 7, 8, 9, 10, 11, 12, 13, 14, 15, 16, 17, 18, 19, or 20 of the amino acids in the amino acid set is a canonical amino acid, and wherein the set of amino acids totals 10, 11, 12, 13, 14, 15, 16, 17, 18, 19, 20, 21, 22, 23, 24, 25, or 26 different amino acids.

In some forms, the amino acid set can consist of any combination of canonical amino acids and non-canonical amino acids, wherein at least 1, 2, 3, 4, 5, 6, 7, 8, 9, 10, 11, 12, 13, 14, 15, 16, 17, 18, 19, or 20 of the amino acids in the amino acid set is a non-canonical amino acid and at least 1, 2, 3, 4, 5, 6, 7, 8, 9, 10, 11, 12, 13, 14, 15, 16, 17, 18, 19, or 20 of the amino acids in the amino acid set is a canonical amino acid, and wherein the set of amino acids totals 10, 11, 12, 13, 14, 15, 16, 17, 18, 19, 20, 21, 22, 23, 24, 25, or 26 different amino acids.

Preferred libraries can use 16-20 amino acids with a 5-mer variable region. This generally optimizes the mix of cost, unique mass, and OBOC synthesis (Table 3).

TABLE 3

| Library Size | Mass (g) Synthesized | Total Number of Beads Synthesized | Number of Beads per Copy | Library Over-sampling | Mass (g) per Copy |
|---|---|---|---|---|---|
| $16^5$ | 5 | 14300000 | 1048576 | 13.64 | 0.37 |
| $17^5$ | 5.3125 | 15193750 | 1419857 | 10.70 | 0.50 |
| $18^5$ | 5.625 | 16087500 | 1889568 | 8.51 | 0.66 |
| $19^5$ | 5.9375 | 16981250 | 2476099 | 6.86 | 0.87 |
| $20^5$ | 6.25 | 17875000 | 3200000 | 5.59 | 1.12 |

The libraries can be synthesized in, for example, 16-20 reaction vessels (1 reaction vessel per amino acid), with 5 split-mix cycles performed to generate 5-mer peptides. Preferred reactions can use a maximum of 0.3125 g of beads per reaction vessel. As an example, Rapp Polymere's beads have $2.86 \times 10^6$ TentaGel S $NH_2$ beads per gram. Current preferred libraries use D-amino acid library of $16^5$ diversity with each screen containing 0.5 g library (>1 copy).

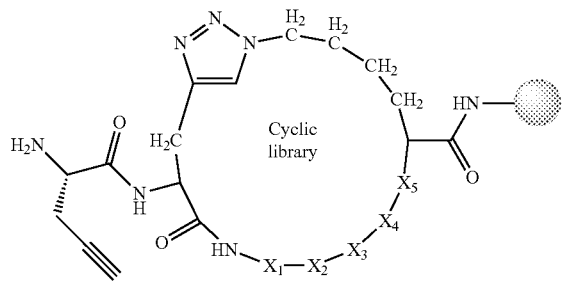

Also disclosed are improved methods for analyzing and assessing epitopes as potential targets for ligands and protein targeting agents. In order to increase our understanding of what makes a candidate sequence a good epitope for PCC targeting, we have implemented in silico methods to increase the likelihood of generating quality hits against the target protein. Examples of the attributes that may lead to a quality hit include the flexibility or rigidity of the epitope (within the context of the entire protein), solvent exposed surface area, overall charge, post-translational modification, and volume of the surrounding surface.

We have used molecular dynamics software to identify areas of any given protein that appear to be more flexible. For this type of stimulation, the crystal structure of the protein interest is solvated in water and the energy of the system is minimized. Due to the low temperature required to crystalize biomolecules, the temperature of the system during the simulation is slowly increase to physiological conditions. This increases the vibrations of both the surrounding water in the simulation and the protein itself. Portions of the protein that are highly structured will not undergo translational, rotational, or vibrational movement to the same extent as regions that are flexible.

Other software including Pymol is utilized to identify long contiguous sequences that are predicted to be solvent exposed. This increases the likelihood that the epitopes that we target with our PCCs will translate to hits against the full-length protein.

The following is an example of the method of assessing epitopes.

Prepare Structure

Crystal Structure Preparation: The native PDB file is downloaded from the RCSB PDB homepage. Any non-proteinaceous material (ligand, stabilizers, crystallographic water, etc.) is extracted and removed from the PDB file using Pymol.

Protein Structure File: NAMD is used to generate a PSF file, which contains the bonding interactions necessary to run the simulation. Partial charges and bond lengths are examples of parameters that are required. Force field topology files are used to interpret the PDB file and to generate the PSF file.

Water Box Preparation: The PDB and PSF files are used to solvate the protein in a water box with at least 5 Å (typically 10 Å for production runs) separating the protein and cell boundary.

Minimization

Minimization Methods: The protein was minimized and equilibrated using periodic boundary conditions employing Particle Mesh Ewald electrostatics. This means that the system (water box) is surrounded by additional water boxes during equilibration. This minimizes the tendencies of surface tension effects from throwing off the calculations if the system was equilibrated in a vacuum.

Production Run: The system was warmed to 310° K, minimized for 1000 steps (sometimes as much as 10,000 steps), and equilibrated for at least 100 ps (typically 1000 or 5000 ps).

The particular features, structures, or characteristics may be combined in any suitable manner in one or more embodiments.

"Amino" refers to the —NH$_2$ radical.

"Cyano" refers to the —CN radical.

"Hydroxy" or "hydroxyl" refers to the —OH radical.

"Imino" refers to the =NH substituent.

"Nitro" refers to the —NO2 radical.

"Oxo" refers to the =O substituent.

"Thioxo" refers to the =S substituent.

"Alkyl" refers to a straight or branched hydrocarbon chain radical consisting solely of carbon and hydrogen atoms, which is saturated or unsaturated (i.e., contains one or more double and/or triple bonds), having from one to twelve carbon atoms ($C_1$-$C_{12}$ alkyl), preferably one to eight carbon atoms ($C_1$-$C_8$ alkyl) or one to six carbon atoms ($C_1$-$C_6$ alkyl), and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, ethenyl, prop-1-enyl, but-1-enyl, pent-1-enyl, penta-1,4-dienyl, ethynyl, propynyl, butynyl, pentynyl, hexynyl, and the like. Unless stated otherwise specifically in the specification, an alkyl group may be optionally substituted.

"Alkylene" or "alkylene chain" refers to a straight or branched divalent hydrocarbon chain linking the rest of the molecule to a radical group, consisting solely of carbon and hydrogen, which is saturated or unsaturated (i.e., contains one or more double and/or triple bonds), and having from one to twelve carbon atoms, e.g., methylene, ethylene, propylene, n-butylene, ethenylene, propenylene, n-butenylene, propynylene, n-butynylene, and the like. The alkylene chain is attached to the rest of the molecule through a single or double bond and to the radical group through a single or double bond. The points of attachment of the alkylene chain to the rest of the molecule and to the radical group can be through one carbon or any two carbons within the chain. Unless stated otherwise specifically in the specification, an alkylene chain may be optionally substituted.

"Alkoxy" refers to a radical of the formula —OR$_a$ where R$_a$ is an alkyl radical as defined above containing one to twelve carbon atoms. Unless stated otherwise specifically in the specification, an alkoxy group may be optionally substituted.

"Aminocarbonyl" refers to a radical of the formula —C(=O)NR$_a$R$_a$, where each R$_a$ is independently H, alkyl or a linker moiety.

"α-amino carbonyl" refers to a radical of the formula —C(=O)CR$_b$(NR$_a$R$_a$)—, where each R$_a$ is independently H, alkyl or a linker moiety and R$_b$ is H or alkyl. In some embodiments, an alpha amino carbonyl is part of a cyclic moiety (e.g., peptide) where the carbonyl is within the ring and the amino (NR$^a$R$^a$) is exocyclic. For example, in certain embodiments and alpha aminocarbonyl is useful for Edman degradation of cyclic peptides.

"α-amido carbonyl" refers to a radical of the formula —C(=O)CR$_b$(N(C=O)R$_a$R$_a$)—, where each R$_a$ is independently H, alkyl or a linker moiety and R$_b$ is H or alkyl. In some embodiments, an alpha amido carbonyl is part of a cyclic moiety (e.g., peptide) where the carbonyl is within the ring and the amido (N(C=O)R$^a$R$^a$) is exocyclic.

"Alkylamino" refers to a radical of the formula —NHR$_a$ or —NR$_a$R$_a$ where each R$_a$ is, independently, an alkyl radical as defined above containing one to twelve carbon atoms. Unless stated otherwise specifically in the specification, an alkylamino group may be optionally substituted.

"Thioalkyl" refers to a radical of the formula —SR$_a$ where R$_a$ is an alkyl radical as defined above containing one to twelve carbon atoms. Unless stated otherwise specifically in the specification, a thioalkyl group may be optionally substituted.

"Aryl" refers to a hydrocarbon ring system radical comprising hydrogen, 6 to 18 carbon atoms and at least one aromatic ring. For purposes of this invention, the aryl radical may be a monocyclic, bicyclic, tricyclic or tetracyclic ring system, which may include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" or the prefix "ar-" (such as in "aralkyl") is meant to include aryl radicals that are optionally substituted.

"Aralkyl" refers to a radical of the formula —R$_b$—R$_c$ where R$_b$ is an alkylene chain as defined above and R$_c$ is one or more aryl radicals as defined above, for example, benzyl, diphenylmethyl and the like. Unless stated otherwise specifically in the specification, an aralkyl group may be optionally substituted.

"Cycloalkyl" or "carbocyclic ring" refers to a stable non-aromatic monocyclic or polycyclic hydrocarbon radical consisting solely of carbon and hydrogen atoms, which may include fused or bridged ring systems, having from three to fifteen carbon atoms, preferably having from three to ten carbon atoms, and which is saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantyl, norbornyl, decalinyl, 7,7-dimethyl-bicyclo[2.2.1]

heptanyl, and the like. Unless otherwise stated specifically in the specification, a cycloalkyl group may be optionally substituted.

"Cycloalkylalkyl" refers to a radical of the formula —$R_bR_d$ where $R_b$ is an alkylene chain as defined above and $R_d$ is a cycloalkyl radical as defined above. Unless stated otherwise specifically in the specification, a cycloalkylalkyl group may be optionally substituted.

"Fused" refers to any ring structure described herein which is fused to an existing ring structure in the compounds of the invention. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Halo" or "halogen" refers to bromo, chloro, fluoro or iodo. "Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group may be optionally substituted.

"Heterocyclyl" or "heterocyclic ring" refers to a stable 3- to 18-membered non-aromatic ring radical which consists of two to twelve carbon atoms and from one to six heteroatoms selected from the group consisting of nitrogen, oxygen and sulfur. Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxothiomorpholinyl. Unless stated otherwise specifically in the specification, Unless stated otherwise specifically in the specification, a heterocyclyl group may be optionally substituted.

"N-heterocyclyl" refers to a heterocyclyl radical as defined above containing at least one nitrogen and where the point of attachment of the heterocyclyl radical to the rest of the molecule is through a nitrogen atom in the heterocyclyl radical. Unless stated otherwise specifically in the specification, a N-heterocyclyl group may be optionally substituted.

"Heterocyclylalkyl" refers to a radical of the formula —$R_bR_e$ where $R_b$ is an alkylene chain as defined above and $R_e$ is a heterocyclyl radical as defined above, and if the heterocyclyl is a nitrogen-containing heterocyclyl, the heterocyclyl may be attached to the alkyl radical at the nitrogen atom. Unless stated otherwise specifically in the specification, a heterocyclylalkyl group may be optionally substituted.

"Heteroaryl" refers to a 5- to 14-membered ring system radical comprising hydrogen atoms, one to thirteen carbon atoms, one to six heteroatoms selected from the group consisting of nitrogen, oxygen and sulfur, and at least one aromatic ring. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl). Unless stated otherwise specifically in the specification, a heteroaryl group may be optionally substituted.

"N-heteroaryl" refers to a heteroaryl radical as defined above containing at least one nitrogen and where the point of attachment of the heteroaryl radical to the rest of the molecule is through a nitrogen atom in the heteroaryl radical. Unless stated otherwise specifically in the specification, an N-heteroaryl group may be optionally substituted.

"Heteroarylalkyl" refers to a radical of the formula —$R_bR_f$ where $R_b$ is an alkylene chain as defined above and $R_f$ is a heteroaryl radical as defined above. Unless stated otherwise specifically in the specification, a heteroarylalkyl group may be optionally substituted.

The term "substituted" used herein means any of the above groups (e.g., alkyl, alkylene, alkoxy, alkylamino, aminocarbonyl, α-aminocarbonyl, α-amidocarbonyl, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl) wherein at least one hydrogen atom is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —$NR_gR_h$, —$NR_gC(=O)R_h$, —$NR_gC(=O)NR_gR_h$, —$NR_gC(=O)OR_h$, —$NR_gSO_2R_h$, —$OC(=O)NR_gR_h$, —$OR_g$, —$SR_g$, —$SOR_g$, —$SO_2R_g$, —$OSO_2R_g$, —$SO_2OR_g$, =$NSO_2R_g$, and —$SO_2NR_gR_h$. "Substituted also means any of the above groups in which one or more hydrogen atoms are replaced with —C(=O)R$_g$, —C(=O)OR$_g$, —C(=O)NR$_g$R$_h$, —CH$_2$SO$_2$R$_g$, —CH$_2$SO$_2$NR$_g$R$_h$. In the foregoing, R$_g$ and R$_h$ are the same or different and independently hydrogen, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl group. In addition, each of the foregoing substituents may also be optionally substituted with one or more of the above substituents.

"Prodrug" is meant to indicate a compound that may be converted under physiological conditions or by solvolysis to a biologically active compound of the invention. Thus, the term "prodrug" refers to a metabolic precursor of a compound of the invention that is pharmaceutically acceptable. A prodrug may be inactive when administered to a subject in need thereof, but is converted in vivo to an active compound of the invention. Prodrugs are typically rapidly transformed in vivo to yield the parent compound of the invention, for example, by hydrolysis in blood. The prodrug compound often offers advantages of solubility, tissue compatibility or delayed release in a mammalian organism (see, Bundgard, H., Design of Prodrugs (1985), pp. 7-9, 21-24 (Elsevier, Amsterdam)). A discussion of prodrugs is provided in Higuchi, T., et al., A. C. S. Symposium Series, Vol. 14, and in Bioreversible Carriers in Drug Design, Ed. Edward B. Roche, American Pharmaceutical Association and Pergamon Press, 1987.

The term "prodrug" is also meant to include any covalently bonded carriers, which release the active compound of the invention in vivo when such prodrug is administered to a mammalian subject. Prodrugs of a compound of the invention may be prepared by modifying functional groups present in the compound of the invention in such a way that the modifications are cleaved, either in routine manipulation or in vivo, to the parent compound of the invention. Prodrugs include compounds of the invention wherein a hydroxy, amino or mercapto group is bonded to any group that, when the prodrug of the compound of the invention is administered to a mammalian subject, cleaves to form a free hydroxy, free amino or free mercapto group, respectively. Examples of prodrugs include, but are not limited to, acetate, formate and benzoate derivatives of alcohol or amide derivatives of amine functional groups in the compounds of the invention and the like.

The invention disclosed herein is also meant to encompass all pharmaceutically acceptable peptides of structure (I) or (I') being isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{36}$Cl, $^{123}$I, and $^{125}$I, respectively. These radiolabelled compounds could be useful to help determine or measure the effectiveness of the compounds, by characterizing, for example, the site or mode of action, or binding affinity to pharmacologically important site of action. Certain isotopically-labelled peptides of the invention, for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^3$N, can be useful in Positron Emission Topography (PET) studies for examining substrate receptor occupancy. Isotopically-labeled peptides can generally be prepared by conventional techniques known to those skilled in the art or by processes analogous to those described in the Preparations and Examples as set out below using an appropriate isotopically-labeled reagent in place of the non-labeled reagent previously employed.

The invention disclosed herein is also meant to encompass the in vivo metabolic products of the disclosed peptides. Such products may result from, for example, the oxidation, reduction, hydrolysis, amidation, esterification, and the like of the administered compound, primarily due to enzymatic processes. Accordingly, the invention includes compounds produced by a process comprising administering a compound of this invention to a mammal for a period of time sufficient to yield a metabolic product thereof. Such products are typically identified by administering a radiolabelled compound of the invention in a detectable dose to an animal, such as rat, mouse, guinea pig, monkey, or to human, allowing sufficient time for metabolism to occur, and isolating its conversion products from the urine, blood or other biological samples.

"Mammal" includes humans and both domestic animals such as laboratory animals and household pets (e.g., cats, dogs, swine, cattle, sheep, goats, horses, rabbits), and non-domestic animals such as wildlife and the like.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Often crystallizations produce a solvate of the compound of the invention. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compound of the invention may be true solvates, while in other cases, the compound of the invention may merely retain adventitious water or be a mixture of water plus some adventitious solvent.

A "pharmaceutical composition" refers to a formulation of a compound of the invention and a medium generally accepted in the art for the delivery of the biologically active compound to mammals, e.g., humans. Such a medium includes all pharmaceutically acceptable carriers, diluents or excipients therefor. "Effective amount" or "therapeutically effective amount" refers to that amount of a peptide of the invention which, when administered to a mammal, preferably a human, is sufficient to effect treatment of a disease or condition in the mammal, preferably a human. The amount of a compound of the invention which constitutes a "therapeutically effective amount" will vary depending on the compound, the condition and its severity, the manner of administration, and the age of the mammal to be treated, but can be determined routinely by one of ordinary skill in the art having regard to his own knowledge and to this disclosure.

"Treating" or "treatment" as used herein covers the treatment of the disease or condition of interest in a mammal, preferably a human, having the disease or condition of interest, and includes:

(i) preventing the disease or condition from occurring in a mammal, in particular, when such mammal is predisposed to the condition but has not yet been diagnosed as having it;

(ii) inhibiting the disease or condition, i.e., arresting its development;

(iii) relieving the disease or condition, i.e., causing regression of the disease or condition; or (iv) relieving the symptoms resulting from the disease or condition, i.e., relieving pain without addressing the underlying disease or condition. As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The compounds (peptides) of the invention, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another.

A "tautomer" refers to a proton shift from one atom of a molecule to another atom of the same molecule. The present invention includes tautomers of any said compounds.

The term "capture agent" as used herein refers to a protein-catalyzed capture (PCC) agent that comprises one or more target-binding moieties and which specifically binds to a target protein via those target-binding moieties. Each target-binding moiety exhibits binding affinity for the target protein, either individually or in combination with other target-binding moieties. In certain embodiments, each target-binding moiety binds to the target protein via one or more non-covalent interactions, including for example hydrogen bonds, hydrophobic interactions, and van der Waals interactions. A capture agent may comprise one or more organic molecules, including for example polypeptides, peptides, polynucleotides, and other non-polymeric molecules.

The terms "polypeptide," "peptide," and "protein" are used interchangeably herein to refer to an amino acid sequence comprising a polymer of amino acid residues. The terms apply to amino acid polymers in which one or more amino acid residues is an artificial chemical mimetic of a corresponding naturally occurring amino acid, as well as to naturally occurring amino acid polymers and non-naturally occurring amino acid polymers.

The term "amino acid" refers to naturally occurring and synthetic amino acids, as well as amino acid analogs and amino acid mimetics that function in a manner similar to the naturally occurring amino acids, and isomers thereof. Naturally occurring amino acids are those encoded by the genetic code, as well as those amino acids that are later modified, e.g., hydroxyproline, carboxyglutamate, O-phosphoserine, and isomers thereof. The term "amino acid analogs" refers to compounds that have the same basic chemical structure as a naturally occurring amino acid, i.e., a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. The term "amino acid mimetics" refers to chemical compounds that have a structure that is different from the general chemical structure of an amino acid, but that functions in a manner similar to a naturally occurring amino acid. Amino acids may be referred to herein by either their commonly known three letter symbols or by the one-letter symbols recommended by the IUPAC-IUB Biochemical Nomenclature Commission.

The term "non-natural amino acid" as used herein refers to an amino acid that is different from the twenty naturally occurring amino acids (alanine, arginine, glycine, asparagine, aspartic acid, cysteine, glutamine, glutamic acid, serine, threonine, histidine, lysine, methionine, proline, valine, isoleucine, leucine, tyrosine, tryptophan, phenylalanine) in its side chain functionality. The non-natural amino acid can be a close analog of one of the twenty natural amino acids, or it can introduce a completely new functionality and chemistry, as long as the hydrophobicity of the non-natural amino acid is either equivalent to or greater than that of the natural amino acid. The non-natural amino acid can either replace an existing amino acid in a protein (substitution), or be an addition to the wild type sequence (insertion). The incorporation of non-natural amino acids can be accomplished by known chemical methods including solid-phase peptide synthesis or native chemical ligation, or by biological methods.

The terms "specific binding," "selective binding," "selectively binds," or "specifically binds" as used herein refer to non-random binding of a binding agent (target binding compound) such as a capture agent to an epitope on a predetermined antigen. Binding agents (e.g., peptides) which specifically bind to a target are also referred to as having affinity for the target, or a binding site thereon. Typically, the binding agent binds with an affinity (KD) of approximately less than $10^{-7}$ M, such as approximately less than $10^{-8}$ M, $10^{-9}$ M or $10^{-10}$ M or even lower.

The term "KD" as used herein refers to the dissociation equilibrium constant of a particular interaction between a binding agent such as a capture agent and its antigen. Typically, the binding agents of the invention bind to a target (e.g., AKT) with a dissociation equilibrium constant (KD) of less than approximately $10^{-7}$ M, such as less than approximately $10^{-8}$ M, $10^{-9}$ M or $10^{-10}$ M or even lower, for example, as determined using surface plasmon resonance (SPR) technology in a Biacore instrument using the antigen as the ligand and the capture agent as the analyte, and binds to the predetermined antigen with an affinity corresponding to a KD that is at least ten-fold lower, such as at least 100 fold lower, for instance at least 1,000 fold lower, such as at least 10,000 fold lower, for instance at least 100,000 fold lower than its affinity for binding to a non-specific antigen (e.g., BSA, casein) other than the predetermined antigen or a closely-related antigen. The amount with which the affinity is lower is dependent on the KD of the capture agent, so that when the KD of the capture agent very low (that is, the capture agent is highly specific), then the amount with which the affinity for the antigen is lower than the affinity for a non-specific antigen may be at least 10,000 fold.

The term "kd" (sec') as used herein refers to the dissociation rate constant of a particular binding agent-antigen interaction. Said value is also referred to as the koff value.

The term "ka" (M-'xsec') as used herein refers to the association rate constant of a particular binding agent-antigen interaction.

The term "KD" (M) as used herein refers to the dissociation equilibrium constant of a particular binding agent-antigen interaction.

The term "KA" (M-') as used herein refers to the association equilibrium constant of a particular binding agent-antigen interaction and is obtained by dividing the ka by the kd.

The term "condition" as used herein refers generally to a disease, event, or a change in health status. A change in health status may be associated with a particular disease or event, in which case the change may occur simultaneously with or in advance of the disease or event. In those cases where the change in health status occurs in advance of a disease or event, the change in health status may serve as a predictor of the disease or event. For example, a change in health status may be an alteration in the expression level of a particular gene associated with a disease or event. Alternatively, a change in health status may not be associated with a particular disease or event.

The term "antibody" as used herein refers to a protein of the kind that is produced by activated B cells after stimulation by an antigen and can bind specifically to the antigen promoting an immune response in biological systems. Full antibodies typically consist of four subunits including two heavy chains and two light chains. The term antibody includes natural and synthetic antibodies, including but not limited to monoclonal antibodies, polyclonal antibodies or fragments thereof. Exemplary antibodies include IgA, IgD, IgG1, IgG2, IgG3, IgM and the like. Exemplary fragments include Fab, Fv, Fab', F(ab')2 and the like. A monoclonal antibody is an antibody that specifically binds to and is thereby defined as complementary to a single particular spatial and polar organization of another biomolecule which is termed an "epitope." In some forms, monoclonal antibodies can also have the same structure. A polyclonal antibody refers to a mixture of different monoclonal antibodies. In some forms, polyclonal antibodies can be a mixture of monoclonal antibodies where at least two of the monoclonal antibodies binding to a different antigenic epitope. The different antigenic epitopes can be on the same target, different targets, or a combination. Antibodies can be prepared by techniques that are well known in the art, such as immunization of a host and collection of sera (polyclonal) or by preparing continuous hybridoma cell lines and collecting the secreted protein (monoclonal).

The term "stable" as used herein with regard to the disclosed peptides or pharmaceutical formulation thereof means that the agent or formulation maintains structural and functional integrity for a sufficient period of time to be useful in the methods described herein.

The term "synthetic" as used herein with regard to the disclosed peptides means that the capture agent has been generated by chemical rather than biological means.

Unless otherwise stated, sequence identity/similarity values provided herein refer to the value obtained using the BLAST 2.0 suite of programs using default parameters (Altschul, et al., (1997) Nucleic Acids Res. 25:3389-402).

As those of ordinary skill in the art will understand, BLAST searches assume that proteins can be modeled as random sequences. However, many real proteins comprise regions of nonrandom sequences, which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, (1993) Comput. Chem. 17:149-63) and XNU (Claverie and States, (1993) Comput. Chem. 17:191-201) low-complexity filters can be employed alone or in combination.

As used herein, "sequence identity" or "identity" in the context of two nucleic acid or polypeptide sequences includes reference to the residues in the two sequences, which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Sequences, which differ by such conservative substitutions, are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, (1988) Computer Applic. Biol. Sci. 4:11-17, e.g., as implemented in the program PC/GENE (Intelligenetics, Mountain View, Calif., USA).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" or "substantially identical" of polynucleotide sequences means that a polynucleotide comprises a sequence that has between 50-100% sequence identity, preferably at least 50% sequence identity, preferably at least 60% sequence identity, preferably at least 70%, more preferably at least 80%, more preferably at least 90% and most preferably at least 95%, compared to a reference sequence using one of the alignment programs described using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of between 55-100%, preferably at least 55%, preferably at least 60%, more preferably at least 70%, 80%, 90% and most preferably at least 95%.

It is to be understood that the disclosed method and compositions are not limited to specific synthetic methods, specific analytical techniques, or to particular reagents unless otherwise specified, and, as such, can vary. It is also to be understood that the terminology used herein is for the purpose of describing particular embodiments only and is not intended to be limiting.

In situ click chemistry (J. Am. Chem. Soc. 126:12809 (2004); Angew. CHem. Int. Ed. Engl. 44:116 (2004); Angew. Chem. Int. Ed. Engl. 45:1435 (2006)) is a technique in which a small molecule enzymatic inhibitor is separated into two moieties, each of which is then expanded into a small library—one containing acetylene functionalities, and the other containing azide groups. The enzyme itself then assembles the 'best fit' inhibitor from these library components by selectively promoting 1,3-dipolar cycloaddition between the acetylene and azide groups to form a triazole linkage (the 'click' reaction). The enzyme promotes the click reaction only between those library components that bind to the protein in the right orientation. The resultant inhibitor can exhibit far superior affinity characteristics relative to the initial inhibitor that formed the basis of the two libraries (Proc. Natl. Acad. Sci. USA 97:9367 (1981); J. Comput. Aided. Mol. Des. 16:741 (2002)).

Sequential in situ click chemistry extends the in situ click chemistry concept to enable the discovery of multiligand capture agents. This process was used previously to produce a triligand capture agent against the model protein carbonic anhydrase II (CAII) (Angew. Chem. Int. Ed. Engl. 48:4944 (2009)). Sequential in situ click chemistry has several advantages. First, structural information about the protein target is replaced by the ability to sample a very large chemical space to identify the ligand components of the capture agent. For example, an initial ligand may be identified by screening the protein against a large ($>10^6$ element) one-bead-one-compound (OBOC) (Nature 354:83 (1991)) peptide library, where the peptides themselves may be comprised of natural, non-natural, and/or artificial amino acids. The resultant anchor ligand is then utilized in an in situ click screen, again using a large OBOC library, to identify a biligand binder. A second advantage is that the process can be repeated, so that the biligand is used as an anchor to identify a triligand, and so forth. The final capture agent can then be scaled up using relatively simple and largely automated chemistries, and it can be developed with a label, such as a biotin group, as an intrinsic part of its structure. This approach permits the exploration of branched, cyclic, and linear capture agent architectures. While many strategies for protein-directed multiligand assembly have been described (Science 274:1531 (1996); Proc. Natl. Acad. Sci. USA 97:9367 (2000)), most require detailed structural information on the target to guide the screening strategy, and most (such as the original in situ click approach), are optimized for low-diversity small molecule libraries.

In some forms, the peptide is a cyclic peptide having the following structure (I):

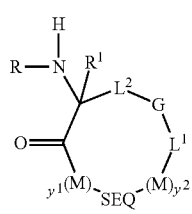
(I)

or a salt, tautomer, prodrug or stereoisomer thereof, wherein:
$L^1$ and $L^2$ are each individually optionally substituted linker moieties, each linker moiety optionally comprising a linkage to a solid support, a linkage to a reporter moiety, a linkage to a peptide ligand, a linkage to an alkyne or azide moiety or combinations thereof;
G is a triazole, a carbon-carbon double bond or an amide;
M is methionine;
R is H, $-L^3$-A or $-C(=O)-L^3$-A, where $L^3$ is a linker moiety and A is an alkyne, azide or a bond to a peptide ligand;
$R^1$ is H or $C_1$-$C_6$alkyl;
$Y^1$ and $Y^2$ are each individually 0 or 1; and
SEQ is an amino acid sequence comprising from 2 to 20 amino acids selected from natural and non-natural amino acids.

A preferred set of amino acids from which the amino acids of SEQ can be selected (Set 1) contains Cyclopropyl Alanine (CyA) and Gly (hydrophobic side chain—aliphatic); 4-Fluorophenyl Alanine (FP), Methyl Tryptophan (MT), 2-Methoxy Pyridylalanine (MeOPyr), and 4-Phenyl Phenylalanine (PhF) (hydrophobic side chain—aromatic); Asn, Ser, Thr (polar side chain—neutral); His, Lys, Arg, Glu (polar side chain—charged); and β-Phenylalanine (BPhA), N-Methyl d-alanine (N-Me-a), and Pro (conformational perturbation).

Another preferred set of amino acids from which the amino acids of SEQ can be selected (Set 2) contains Cyclopropyl Alanine (CyA) and Gly (hydrophobic side chain—aliphatic); 4-Fluorophenyl Alanine (FP), Methyl Tryptophan (MT), Thiazolyl Alanine (Thz), 4-Phenyl Phenylalanine (PhF), and Phe (hydrophobic side chain—aromatic); Asn, Ser, Thr (polar side chain—neutral); His, Lys, Arg, Glu (polar side chain—charged); and N-Methyl d-alanine (N-Me-a), and Pro (conformational perturbation).

Another preferred set of amino acids from which the amino acids of SEQ can be selected (Set 3) contains Cyclopropyl Alanine (CyA) and Gly (hydrophobic side chain—aliphatic); 4-Fluorophenyl Alanine (FP), Methyl Tryptophan (MT), 2-Methoxy Pyridylalanine (MeOPyr), Thiazolyl Alanine (Thz), 4-Phenyl Phenylalanine (PhF), and Phe (hydrophobic side chain—aromatic); Asn, Ser, Thr (polar side chain—neutral); His, Lys, Arg, Glu (polar side chain—charged); and β-Phenylalanine (BPhA), N-Methyl d-alanine (N-Me-a), and Pro (conformational perturbation).

In some embodiments, G is a triazole. Such triazoles may be derived by reaction of an alkyne and azide on a precursor acyclic peptide.

In other embodiments, G is a carbon-carbon double bond. In some embodiments, these peptides are obtained by reactions of two carbon-carbon double bonds (alkenes) present in an acyclic precursor. Such reactions can be carried out using Grubbs metathesis chemistry, which is well-known to those of skill in the art.

In various other embodiments, $L^1$, $L^2$, or both, comprise one or more substituents selected from alkyl, alkyne, azide and aminocarbonyl. In some other embodiments of any of the foregoing, $L^1$, $L^2$, or both, comprise a linkage selected from a linkage to a solid support, a linkage to a reporter moiety and a linkage to a peptide ligand. In some specific embodiments of the foregoing, $L^1$ and $L^2$ are alkylene.

In some other embodiments of the foregoing, the cyclic peptide has one of the following structures (Ia) or (Ib):

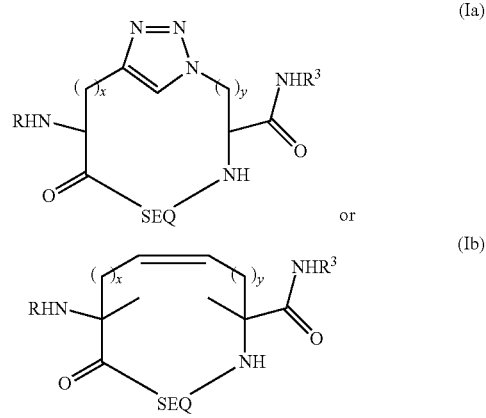

wherein:
$R^3$ is H, a linkage to a solid support, a linkage to a reporter moiety, a linkage to a peptide ligand, a linkage to an alkyne or azide moiety or combinations thereof; and
x and y are each independently an integer from 1 to 8.

In some embodiments of the compounds of structure (Ia) and (Ib), x is 1. In other embodiments, x is 2. In more embodiments, x is 3. In still other embodiments, x is 4. In other embodiments, x is 5. In some other embodiments, x is 6. In yet more embodiments, x is 7. In other embodiments, x is 8.

In some embodiments of the compounds of structure (Ia) and (Ib), y is 1. In other embodiments, y is 2. In more embodiments, y is 3. In still other embodiments, y is 4. In other embodiments, y is 5. In some other embodiments, y is 6. In yet more embodiments, y is 7. In other embodiments, y is 8.

In other embodiments, R is H or $-C(=O)-L^3$-A, where $L^3$ is a linker moiety and A is a bond to a peptide ligand or an alkyne. In some of these embodiments, A is an alkyne. In other embodiments the cyclic peptide is biligand binding agent, and A is a bond to a peptide ligand, for example a linear peptide ligand or a cyclic peptide ligand. In further embodiments, the peptide ligand further comprises a second peptide ligand, and the cyclic peptide is this a tri-ligand binding agent.

The structure of the "linker moieties" (e.g., linker moieties to reporter moieties or further peptides, etc.) are not particularly limited. For example, in certain embodiments, linkers comprising ethylene glycol of various lengths (e.g., 1-10 glycol repeating units, e.g., about 5-7). Ethylene diamine linkers may also be employed alone or in combination with other moieties (e.g., ethylene glycol). Linker moieties comprising triazole (e.g., resulting from reaction of an alkyne and azide) are also useful in various embodiments.

In some of the foregoing embodiments, $y^1$ and $y^2$ are each 0.

In even more embodiments, the cyclic peptide has one of the following structures:

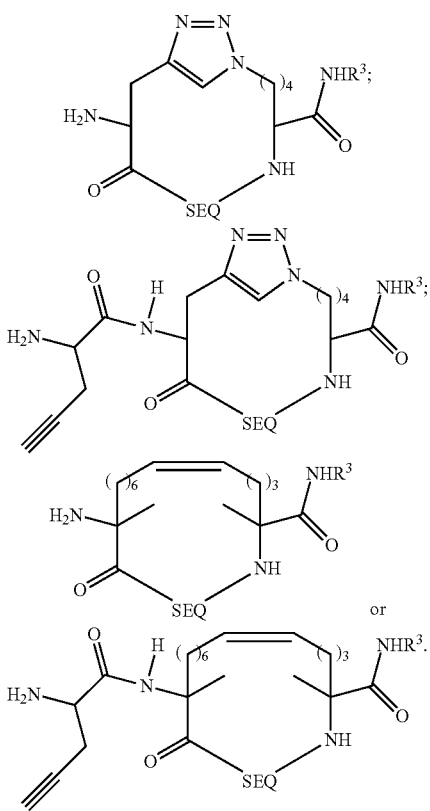

For example, in some of any of the foregoing embodiments SEQ comprises from 2 to 9 amino acids. In other embodiments, SEQ comprises from 5 to 7 amino acids.

In certain embodiments, SEQ comprise natural amino acids. In other embodiments, SEQ comprises non-natural amino acids. In still more embodiments, SEQ comprises natural and non-natural amino acids.

In some more specific embodiments any of the foregoing embodiments, the amino acids are selected from D and L stereoisomers of Ala, Gly, Leu, Ile, Val, Phe, Trp, Arg, His, Lys, Asp, Glu, Asn, Gln, Ser, Thr, Tyr and Pro. In some more specific embodiments any of the foregoing embodiments, the amino acids are selected from D and L stereoisomers of Ala, Gly, Leu, Val, Phe, Trp, Arg, His, Lys, Asp, Glu, Asn, Ser, Thr, Tyr and Pro. In some more specific embodiments any of the foregoing embodiments, the amino acids are selected from CyA, Gly, FP, MT, MeOPyr, PhF, Asn, Ser, Thr, His, Lys, Arg, Glu, BPhA, N-Me-a, and Pro (Set 1). In some more specific embodiments any of the foregoing embodiments, the amino acids are selected from CyA, Gly, FP, MT, Thz, PhF, Phe, Asn, Ser, Thr, His, Lys, Arg, Glu, N-Me-a, and Pro (Set 2). In some more specific embodiments any of the foregoing embodiments, the amino acids are selected from CyA, Gly, FP, MT, MeOPyr, Thz, PhF, Phe, Asn, Ser, Thr, His, Lys, Arg, Glu, BPhA, N-Me-a, and Pro (Set 3).

The amino acids in SEQ are selected to have affinity for the desired target, including allosteric binding sites such as protein epitopes.

Compositions comprising any of the foregoing cyclic peptides and a pharmaceutically acceptable carrier are also provided in various embodiments. In other embodiments, a library comprising a plurality of the forgoing cyclic peptides is provided.

In certain embodiments, the cyclic peptides (also referred to herein as capture agents or binding agents) provided herein have a shelf-life of greater than six months, meaning that they are stable in storage for greater than six months. In certain of these embodiments, the capture agents have a shelf-life of one year or greater, two years or greater, or more than three years. In certain of these embodiments, the capture agents are stored as a lyophilized powder. In certain embodiments, the capture agents provided herein have a longer shelf-life than a biologic binding to the same target protein.

In certain embodiments, the capture agents provided herein are stable at temperatures ranging from about −80° C. to about 120° C. In certain of these embodiments, the capture agents are stable within a temperature range of −80° C. to −40° C.; −40° C. to −20° C.; −20° C. to 0° C.; 0° C. to 20° C.; 20° C. to 40° C.; 40° C. to 60° C.; 60° C. to 80° C.; and/or 80° C. to 120° C. In certain embodiments, the capture agents provided herein are stable across a wider range of temperatures than a biologic binding to the same target protein, and/or remain stable at a specific temperature for a longer time period than a biologic binding to the same target protein.

In certain embodiments, the pH of a capture agent provided herein is in the range of about 3.0 to about 12.0. In certain of these embodiments, the pH of the capture agent is in the range of about 5.0 to about 9.0. The pH of a capture agent may be adjusted to a physiologically compatible range using methods known in the art. For example, in certain embodiments the pH of the capture agent may be adjusted to the range of about 6.5 to about 8.5.

In certain embodiments, the capture agents provided herein are stable in blood serum for more than 12 hours. In certain of these embodiments, the capture agents are stable in blood serum for more than 18 hours, more than 24 hours, more than 36 hours, more than 48 hours, or more than 96 hours. In certain embodiments, the capture agents provided herein are stable for a longer period of time in blood serum than a biologic binding to the same target protein.

In certain embodiments, the capture agents provided herein may comprise one or more detection labels (reporter group), including for example biotin, copper-1,4,7,10-tetraazacyclododecane-1,4,7,10-tetraaceticacid (copper-DOTA), desferrioxamine B (DFO), a ligand for radiolabeling with $^{68}$Ga, or other radiolabeled products that may include gamma emitters, proton emitters, positron emitters, tritium, or covered tags detectable by other methods (i.e., gadolinium) among others.

In certain embodiments, the capture agents provided herein comprise one or more detectable labels. In certain of these embodiments, the label is copper-DOTA. In other embodiments, the detectable label is selected from $^{64}$Cu DOTA, $^{68}$Ga DOTA, $^{18}$F, $^{64}$Cu, $^{68}$Ga, $^{89}$Zr, $^{124}$I, $^{86}$Y, $^{94m}$Tc, $^{110m}$In, $^{11}$C and $^{76}$Br. In other embodiments, the detectable label is selected from $^{123}$I, $^{131}$I, $^{67}$Ga, $^{111}$In and $^{99m}$Tc. In other embodiments, the label is a fluorescent label.

In some other embodiments, the cyclic peptide comprises a linkage to a reporter moiety, the reporter moiety selected from polyethylene glycol (PEG), biotin, thiol and fluorophores. For example, in some embodiments the fluorophores are selected from FAM, FITC, Cy5, TRITC, TAMRA.

Table 1 provides reporter moieties useful in various different applications of the cyclic peptides. Other useful reporter moieties can be derived by one of skill in the art.

TABLE 1

Reporter Moieties

| Application | Reporter |
|---|---|
| ELISA: microtiter plate | Biotin |
| ELISA: lateral flow test | Biotin |
| Immunoprecipitation (and other bead-based assays) | Biotin, thiol |
| Dot blot | Biotin |
| Cell-based assay | Biotin, fluorophore |
| IHC | Biotin, fluorophore |
| In vivo imaging: PET | Radioisotopes including $^{18}$F, $^{68}$Ga, $^{64}$Cu, $^{89}$Zr, $^{124}$I |
| In vivo imaging: SPECT | Radioisotopes including $^{111}$In, $^{90}$Y, $^{99m}$Tc |
| In vivo imaging: MR | $Gd^{3+}$ |

In certain embodiments, the capture agents provided herein may be modified to obtain a desired chemical or biological activity. Examples of desired chemical or biological activities include, without limitation, improved solubility, stability, bioavailability, detectability, or reactivity. Examples of specific modifications that may be introduced to a capture agent include, but are not limited to, cyclizing the capture agent through formation of a disulfide bond; modifying the capture agent with other functional groups or molecules. Similarly, a capture agent may be synthesized to bind to non-canonical or non-biological epitopes on proteins, thereby increasing their versatility. In certain embodiments, the capture agent may be modified by modifying the synthesis blocks of the target-binding moieties before the coupling reaction.

Provided herein in certain embodiments are pharmaceutical formulations comprising one or more of the capture agents provided herein. In certain embodiments, these pharmaceutical formulations comprise one or more pharmaceutically acceptable carriers, excipients, or diluents. These carriers, excipients, or diluents may be selected based on the intended use and/or route of administration of the formulation.

Provided herein in certain embodiments are kits comprising one or more of the capture agents disclosed herein. In certain embodiments, the kits provided herein may further comprise instructions for suitable operational parameters in the form of a label or a separate insert. For example, the kit may have standard instructions informing a consumer/kit user how to wash the probe after a sample of plasma or other tissue sample is contacted on the probe.

It is understood that any embodiment of the peptides, as set forth above, and any specific substituent set forth herein for a R, R$^1$, L$^1$, L$^2$, G, M, Y$^1$ Y$^2$ or SEQ group in the peptides, as set forth above, may be independently combined with other embodiments and/or substituents of the peptides to form embodiments of the inventions not specifically set forth above. In addition, in the event that a list of substituents is listed for any particular variable in a particular embodiment and/or claim, it is understood that each individual substituent may be deleted from the particular embodiment and/or claim and that the remaining list of substituents will be considered to be within the scope of the invention.

For the purposes of administration, the peptides of the present invention may be administered as a raw chemical or may be formulated as pharmaceutical compositions. Pharmaceutical compositions of the present invention comprise a peptide of structure (I) and a pharmaceutically acceptable carrier, diluent or excipient. The peptide of structure (I) is present in the composition in an amount which is effective to treat a particular disease or condition of interest—that is, and preferably with acceptable toxicity to the patient. Activity of compounds of the peptides can be determined by one skilled in the art, for example, as described in the Examples. Appropriate concentrations and dosages can be readily determined by one skilled in the art.

Administration of the compounds of the invention, or their pharmaceutically acceptable salts, in pure form or in an appropriate pharmaceutical composition, can be carried out via any of the accepted modes of administration of agents for serving similar utilities. The pharmaceutical compositions of the invention can be prepared by combining a compound of the invention with an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. Typical routes of administering such pharmaceutical compositions include, without limitation, oral, topical, transdermal, inhalation, parenteral, sublingual, buccal, rectal, vaginal, and intranasal. The term parenteral as used herein includes subcutaneous injections, intravenous, intramuscular, intrasternal injection or infusion techniques. Pharmaceutical compositions of the invention are formulated so as to allow the active ingredients contained therein to be bioavailable upon administration of the composition to a patient. Compositions that will be administered to a subject or patient take the form of one or more dosage units, where for example, a tablet may be a single dosage unit, and a container of a compound of the invention in aerosol form may hold a plurality of dosage units. Actual methods of preparing such dosage forms are known, or will be apparent, to those skilled in this art; for example, see Remington: The Science and Practice of Pharmacy, 20th Edition (Philadelphia College of Pharmacy and Science, 2000). The composition to be administered will, in any event, contain a therapeutically effective amount of a compound of the invention, or a pharmaceutically acceptable salt thereof, for treatment of a disease or condition of interest in accordance with the teachings of this invention.

A pharmaceutical composition of the invention may be in the form of a solid or liquid. In one aspect, the carrier(s) are particulate, so that the compositions are, for example, in tablet or powder form. The carrier(s) may be liquid, with the compositions being, for example, an oral syrup, injectable liquid or an aerosol, which is useful in, for example, inhalatory administration.

When intended for oral administration, the pharmaceutical composition is preferably in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like form. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When the pharmaceutical composition is in the form of a capsule, for example, a gelatin capsule, it may contain, in addition to materials of the above type, a liquid carrier such as polyethylene glycol or oil.

The pharmaceutical composition may be in the form of a liquid, for example, an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions of the invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition of the invention intended for either parenteral or oral administration should contain an amount of a compound of the invention such that a suitable dosage will be obtained.

The pharmaceutical composition of the invention may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device.

The pharmaceutical composition of the invention may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter and polyethylene glycol.

The pharmaceutical composition of the invention may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

The pharmaceutical composition of the invention in solid or liquid form may include an agent that binds to the compound of the invention and thereby assists in the delivery of the compound. Suitable agents that may act in this capacity include a monoclonal or polyclonal antibody, a protein or a liposome.

The pharmaceutical composition of the invention may consist of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds of the invention may be delivered in single phase, bi-phasic, or tri-phasic systems in order to deliver the active ingredient(s). Delivery of the aerosol includes the necessary container, activators, valves, subcontainers, and the like, which together may form a kit. One skilled in the art, without undue experimentation may determine preferred aerosols.

The pharmaceutical compositions of the invention may be prepared by methodology well known in the pharmaceutical art. For example, a pharmaceutical composition intended to be administered by injection can be prepared by combining a compound of the invention with sterile, distilled water so as to form a solution. A surfactant may be added to facilitate the formation of a homogeneous solution or suspension. Surfactants are compounds that non-covalently interact with the compound of the invention so as to facilitate dissolution or homogeneous suspension of the compound in the aqueous delivery system.

The compounds of the invention, or their pharmaceutically acceptable salts, are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy.

Compounds of the invention, or pharmaceutically acceptable derivatives thereof, may also be administered simultaneously with, prior to, or after administration of one or more other therapeutic agents. Such combination therapy includes administration of a single pharmaceutical dosage formulation which contains a compound of the invention and one or more additional active agents, as well as administration of the compound of the invention and each active agent in its own separate pharmaceutical dosage formulation. For example, a compound of the invention and the other active agent can be administered to the patient together in a single oral dosage composition such as a tablet or capsule, or each agent administered in separate oral dosage formulations. Where separate dosage formulations are used, the compounds of the invention and one or more additional active agents can be administered at essentially the same time, i.e., concurrently, or at separately staggered times, i.e., sequentially; combination therapy is understood to include all these regimens.

It is understood that in the present description, combinations of substituents and/or variables of the depicted formulae are permissible only if such contributions result in stable compounds.

It will also be appreciated by those skilled in the art that in the process described herein the functional groups of intermediate compounds may need to be protected by suitable protecting groups. Such functional groups include hydroxy, amino, mercapto and carboxylic acid. Suitable protecting groups for hydroxy include trialkylsilyl or diaryalkylsilyl (for example, t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R" (where R" is alkyl, aryl or arylalkyl), p-methoxybenzyl, trityl and the like. Suitable protecting groups for carboxylic acid include alkyl, aryl or arylalkyl esters. Protecting groups may be added or removed in accordance with standard techniques, which are known to one skilled in the art and as described herein. The use of protecting groups is described in detail in Green, T. W. and P. G. M. Wutz, *Protective Groups in Organic Synthesis* (1999), 3rd Ed., Wiley. As one of skill in the art would appreciate, the protecting group may also be a polymer resin such as a Wang resin, Rink resin or a 2-chlorotrityl-chloride resin.

It will also be appreciated by those skilled in the art, although such protected derivatives of compounds of this invention may not possess pharmacological activity as such, they may be administered to a mammal and thereafter metabolized in the body to form compounds of the invention which are pharmacologically active. Such derivatives may therefore be described as "prodrugs". All prodrugs of compounds of this invention are included within the scope of the invention.

Furthermore, all compounds of the invention which exist in free base or acid form can be converted to their pharmaceutically acceptable salts by treatment with the appropriate inorganic or organic base or acid by methods known to one skilled in the art. Salts of the compounds of the invention can be converted to their free base or acid form by standard techniques.

The peptides of the invention can be prepared by procedures known to those of skill in the art. For example, the peptides can be prepared using standard solid-phase peptide synthesis techniques, and modifications thereof. Modified amino acids may be employed to incorporate amino acids comprising alkyne and/or azide moieties and/or alkene moieties useful for cyclization. Methods for cyclizing the peptides using azide/alkyne chemistry and Grubbs metathesis chemistry are well-known in the art. Such methods are described in more detail in the examples.

It is understood that one skilled in the art may be able to make these compounds by similar methods or by combining other methods known to one skilled in the art. It is also understood that one skilled in the art would be able to make, in a similar manner as described below, other peptides not specifically illustrated in the examples below by using the appropriate starting components and modifying the parameters of the synthesis as needed. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, for example, Advanced Organic Chemistry: Reactions, Mechanisms, and Structure, 5th edition (Wiley, December 2000)) or prepared as described in this invention.

Methods for Use of the Peptides

In various embodiments, the present invention provides methods for identification of cyclic peptides which are useful as binding agents for various targets. In general, the methods employ cyclic peptides, such as any of the cyclic peptides described herein above, in methods for identification of mono-, bi- and/or tri-ligand binding agents. Higher order binding agents (tetra, penta, and the like) are also within the scope of the present invention.

In general, the present invention includes any methods employing the cyclic peptides described herein. Accordingly, in one embodiment a method for identifying a target binding compound (e.g., a protein capture agent) is provided, the method comprising A). providing a peptide library comprising a plurality of cyclic peptides comprising:
  i. a sequence region comprising amino and carboxy termini and a variable peptide sequence of two to twenty amino acids selected from natural and non-natural amino acids; and
  ii. a linker region comprising a α-amino carbonyl, α-amido carbonyl, a methionine amino acid, or combinations thereof, and optionally comprising an alkyne, an azide, a linkage to a solid support or a linkage to a reporter moiety or a combination thereof, the linker region covalently linking the amino and carboxy termini of the sequence region.

B) contacting the peptide library with a target or a truncated analogue thereof, the target or truncated analogue thereof comprising a binding site and optionally an alkyne, azide or reporter moiety or combinations thereof;

C) identifying a peptide library member with affinity for the binding site

In further embodiments, a method for identifying a target binding compound (e.g., a protein capture agent) is provided, the method comprising:

A) providing a first peptide library comprising a plurality of first peptide library members, the first peptide library members optionally comprising an alkyne, azide or reporter moiety or combinations thereof;

B) contacting the first peptide library with a target or a truncated analogue thereof, the target or truncated analogue thereof comprising a first binding site and optionally an alkyne, azide or reporter moiety or combinations thereof;

C) identifying a first peptide library member with affinity for the first binding site and optionally modifying the first peptide library member to include an alkyne or azide moiety;

and optionally:

D) providing a second peptide library comprising a plurality of second peptide library members, the second peptide library members comprising an azide or alkyne or both;

E) contacting the second peptide library with a composition comprising the target or truncated analogue thereof and the first peptide library member of step C;

F) forming a triazole-linked conjugate between the first peptide library member of step C and a second peptide library member, the second peptide library member having affinity for a second binding site on the target or truncated analogue thereof, wherein the first peptide library, the second peptide library, or both, comprise cyclic peptides comprising:
i. a sequence region comprising amino and carboxy termini and a variable peptide sequence of two to twenty amino acids selected from natural and non-natural amino acids; and
ii. a linker region comprising a α-amino carbonyl, α-amido carbonyl, a methionine amino acid, or combinations thereof, and optionally comprising an alkyne, an azide, a linkage to a solid support or a linkage to a reporter moiety or a combination thereof, the linker region covalently linking the amino and carboxy termini of the sequence region.

A preferred set of amino acids from which the amino acids of SEQ can be selected contains Cyclopropyl Alanine (CyA) and Gly (hydrophobic side chain—aliphatic); 4-Fluorophenyl Alanine (FP), Methyl Tryptophan (MT), 2-Methoxy Pyridylalanine (MeOPyr), and 4-Phenyl Phenylalanine (PhF) (hydrophobic side chain—aromatic); Asn, Ser, Thr (polar side chain—neutral); His, Lys, Arg, Glu (polar side chain—charged); and β-Phenylalanine (BPhA), N-Methyl d-alanine (N-Me-a), and Pro (conformational perturbation).

Another preferred set of amino acids from which the amino acids of SEQ can be selected (Set 2) contains Cyclopropyl Alanine (CyA) and Gly (hydrophobic side chain—aliphatic); 4-Fluorophenyl Alanine (FP), Methyl Tryptophan (MT), Thiazolyl Alanine (Thz), 4-Phenyl Phenylalanine (PhF), and Phe (hydrophobic side chain—aromatic); Asn, Ser, Thr (polar side chain—neutral); His, Lys, Arg, Glu (polar side chain—charged); and N-Methyl d-alanine (N-Me-a), and Pro (conformational perturbation).

Another preferred set of amino acids from which the amino acids of SEQ can be selected (Set 3) contains Cyclopropyl Alanine (CyA) and Gly (hydrophobic side chain—aliphatic); 4-Fluorophenyl Alanine (FP), Methyl Tryptophan (MT), 2-Methoxy Pyridylalanine (MeOPyr), Thiazolyl Alanine (Thz), 4-Phenyl Phenylalanine (PhF), and Phe (hydrophobic side chain—aromatic); Asn, Ser, Thr (polar side chain—neutral); His, Lys, Arg, Glu (polar side chain—charged); and β-Phenylalanine (BPhA), N-Methyl d-alanine (N-Me-a), and Pro (conformational perturbation).

In some forms, SEQ can comprise t(Thz)pk(FP), t(PhF)Gk(FP), t(Thz)hkn (SEQ ID NO:2), t(Thz)(FP)kG, tG(PhF)k(N-Me-a), t(CyA)(PhF)kh, t(CyA)(FP)kn, t(N-Me-a)(N-Me-a)kn, t(N-Me-a)pke (SEQ ID NO:3), tphkn (SEQ ID NO:4), t(CyA)rks (SEQ ID NO:5), tpkk(N-Me-a) (SEQ ID NO:6), t(CyA)ek(N-Me-a), t(CyA)ekh (SEQ ID NO:7), t(CyA)tk(CyA), tesk(CyA) (SEQ ID NO:8), tetk(N-Me-a) (SEQ ID NO:9), tenk(FP) (SEQ ID NO:10), tekkp (SEQ ID NO:11), tskk(N-Me-a) (SEQ ID NO:12), ttrk (SEQ ID NO:13), tnkk(CyA) (SEQ ID NO:14), ts(Thz)k(CyA), tk(FP)kk (SEQ ID NO:15), trrk(CyA) (SEQ ID NO:16), trrks (SEQ ID NO:17), tkrkr (SEQ ID NO:18), trkkh (SEQ ID NO:19), trnkr (SEQ ID NO:20), ttkkr (SEQ ID NO:21), tshkr (SEQ ID NO:22), t(Thz)rkk (SEQ ID NO:23), tr(Thz)kr (SEQ ID NO:24), tr(FP)kr (SEQ ID NO:25), tk(FP)kr (SEQ ID NO:26), trGkr (SEQ ID NO:27), tG(CyA)kr (SEQ ID NO:28), tp(CyA)k(FP), te(MT)kp (SEQ ID NO:29), tnpks (SEQ ID NO:31), tp(CyA)k(FP), t(CyA/e/Thz)(k/FP)k(N-Me-a/n/FP), or trrkr (SEQ ID NO:30).

For purposes of clarity, it should be noted that steps D-F are optional and the above described method is not limited to methods which require conjugation of a second peptide. It is understood that when steps D-F are not performed, the first library comprises the cyclic peptide; however when steps D-F are performed the cyclic peptides may be a part of either the first, second or both libraries. It should also be emphasized that the methods are not limited to identification of mono or bi-ligand binding agents, and the methods described herein can be extrapolated to identification of tertiary, ternary and higher binding agents (e.g., by performing steps analogous to steps D-F). In general, any of the cyclic peptides described herein above may be employed in the above methods. Specific embodiments of the peptides useful in the some embodiments of the methods are illustrated herein.

In certain embodiments of the method, the linker region comprises a α-amino carbonyl group bound to the amino terminus of the peptide sequence. In some of these embodiments, the method further comprises determining the peptide sequence of one or more of the cyclic peptides by Edman degradation.

In other embodiments, the linker region comprises a methionine amino acid bound to the amino terminus of the variable peptide sequence. In some of these embodiments, the method further comprises treating one or more of the cyclic peptides with CNBr and determining the sequence thereof by mass spectrometry.

In other embodiments of the foregoing methods, the linker region comprises an alkyne or azide, the target or a truncated analogue thereof comprises an alkyne or azide and identifying the first peptide library member with affinity for the first binding site comprises identifying first peptide library members which form a triazole linkage with the target or a truncated analogue thereof.

In some embodiments, the first peptide library is contacted with a truncated analogue of the target.

In other aspects, the method further comprises modifying the triazole linked conjugate to contain a triazole or alkyne and contacting the modified conjugate with the target or truncated analogue thereof and a third peptide library, the third peptide library comprising a plurality of third peptide library members, each third peptide library member comprising an azide or alkyne.

In still other embodiments, the method further comprises forming a triazole linkage between the modified conjugate and a member of the third peptide library, the third peptide library member having affinity for a third binding site on the target or truncated analogue thereof.

In some embodiments, the first binding site is an epitope. In other embodiments, the second binding site is an epitope. In some more embodiments, the third binding site is an epitope.

In various different embodiments, the linker region comprises a carbon-carbon double bond or a triazole.

In some embodiments the cyclic peptides have the following structure (I'):

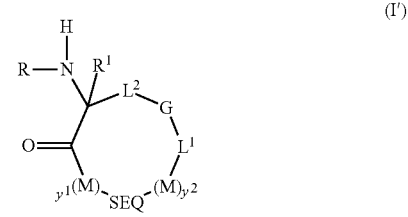

or a salt, tautomer or stereoisomer thereof, wherein:
$L^1$ and $L^2$ are each individually optionally substituted linker moieties, each linker moiety optionally comprising a linkage to a solid support, a linkage to a reporter moiety, a linkage to an alkyne or azide moiety or a linkage to a peptide ligand;

G is a triazole a carbon-carbon double bond or an amide;

M is methionine;

R is H, -L³-A or —C(=O)-L³-A, where L³ is a linker moiety and A is an alkyne or azide;

R¹ is H or $C_1$-$C_6$alkyl;

Y¹ and Y² are each individually 0 or 1; and

SEQ is the variable peptide sequence.

In some embodiments, Y¹ and Y² are each 0.

For example, in some of any of the foregoing embodiments SEQ comprises from 2 to 9 amino acids. In other embodiments, SEQ comprises from 5 to 7 amino acids.

In certain embodiments, SEQ comprise natural amino acids. In other embodiments, SEQ comprises non-natural amino acids. In still more embodiments, SEQ comprises natural and non-natural amino acids.

In some more specific embodiments any of the foregoing embodiments, the amino acids are selected from D and L stereoisomers of Ala, Gly, Leu, Ile, Val, Phe, Trp, Arg, His, Lys, Asp, Glu, Asn, Gln, Ser, Thr, Tyr and Pro. In some more specific embodiments any of the foregoing embodiments, the amino acids are selected from D and L stereoisomers of Ala, Gly, Leu, Val, Phe, Trp, Arg, His, Lys, Asp, Glu, Asn, Ser, Thr, Tyr and Pro. In some more specific embodiments any of the foregoing embodiments, the amino acids are selected from CyA, Gly, FP, MT, MeOPyr, PhF, Asn, Ser, Thr, His, Lys, Arg, Glu, BPhA, N-Me-a, and Pro.

The amino acids in SEQ are selected to have affinity for the desired target, including allosteric binding sites such as protein epitopes.

In other embodiments, the cyclic peptides have the following structure (I'a):

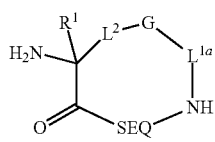

wherein:

$L^{1a}$ is a linker moiety optionally substituted with one or more substituent selected from a linkage to an alkyne or azide moiety, a linkage to a solid support and a linkage to a reporter moiety.

In some embodiments, $L^{1a}$ and $L^2$ are each independently optionally substituted alkylene.

In other embodiments, the cyclic peptides have the following structure (I'b):

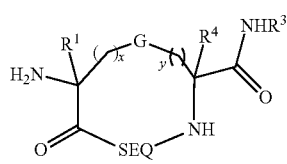

wherein:

R³ is H, a linkage to a solid support, a linkage to an alkyne or azide moiety or a linkage to a reporter moiety;

R⁴ is H or $C_1$-$C_6$ alkyl; and x and y are each independently integers from 1 to 8.

In certain of the forgoing embodiments, G is a triazole. In other embodiments, G is a carbon-carbon double bond.

In some more specific embodiments, the cyclic peptides have one of the following structures:

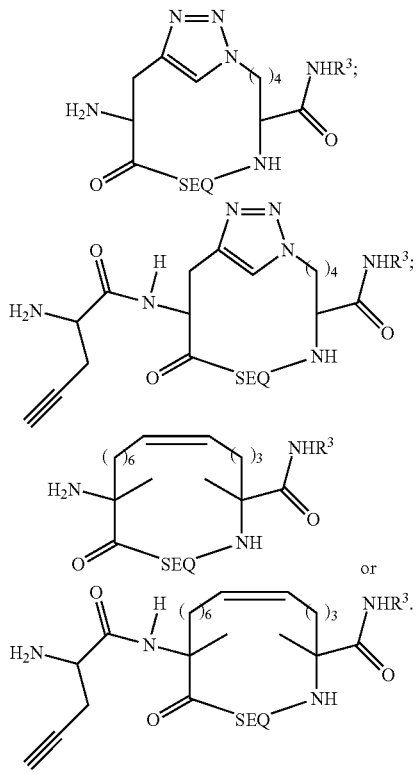

In still other embodiments, the first peptide library comprises the cyclic peptides, and the second peptide library comprises linear peptide members.

In different embodiments, the second peptide library comprises the cyclic peptides, and the first peptide library comprises linear peptide members. In more embodiments, the first and second peptide library comprises the cyclic peptides.

In some embodiments, the target is a protein, for example a protein epitope. In some embodiments, the protein is an enzyme or cell surface protein.

Provided herein in certain embodiments are methods of using the capture agents disclosed herein to identify, detect, quantify, and/or separate target proteins in a biological sample. The capture agents disclosed herein can serve as a drop-in replacement for monoclonal antibodies in biochemical assays. Therefore, in certain embodiments the methods provided herein utilize an immunoassay, with the capture agent replacing an antibody or its equivalent. In certain embodiments, the immunoassay may be a Western blot, pull-down assay, dot blot, or ELISA.

A biological sample for use in the methods provided herein may be selected from the group consisting of organs, tissue, bodily fluids, and cells. Where the biological sample is a bodily fluid, the fluid may be selected from the group consisting of blood, blood serum, plasma, urine, sputum, saliva, stool, spinal fluid, cerebral spinal fluid, lymph fluid, skin secretions, respiratory secretions, intestinal secretions, genitourinary tract secretions, tears, and milk.

Provided herein in certain embodiments are methods of identifying, detecting, quantifying, and/or localizing a target protein in vivo. In certain of these embodiments, the capture agents may be used as an imaging agent. In these embodiments, the capture agents may comprise one or more detection labels as discussed above.

Provided herein in certain embodiments are methods of using the capture agents disclosed herein to inhibit a target protein activity. In certain of these embodiments, the capture agents inhibit target protein activity by blocking binding of the target protein to its native substrate.

Provided herein in certain embodiments are methods of using the capture agents disclosed herein to diagnose and/or classify (e.g., stage) a condition associated with increased target protein expression and/or activity. In certain embodiments, these methods comprise (a) obtaining a biological sample from a subject; (b) measuring the presence or absence of target protein in the sample with the capture agent; (c) comparing the levels of target protein to a predetermined control range for target protein; and (d) diagnosing a condition associated with increased target protein expression based on the difference between target protein levels in the biological sample and the predetermined control.

In certain embodiments of the diagnosis and/or classification methods provided herein, the capture agents may be used to diagnose a change in health status in a subject, wherein the change in health status is a predictor of a disease or event. In certain of these embodiments, the methods may be utilized to predict the development of a disease or event in a subject who does not yet exhibit any symptoms of the disease or event. In certain embodiments, the change in health status may be an increase in target protein levels.

Provided herein in certain embodiments are methods of treating a condition associated with increased target protein expression and/or activity in a subject in need thereof by administering a therapeutically effective amount of one or more of the capture agents or pharmaceutical formulations disclosed herein. In certain of these embodiments, the capture agent(s) may be linked to one or more additional therapeutic agents, including for example a chemotherapeutic agent. In preferred embodiments, the capture agent is administered as a pharmaceutical composition.

A capture agent or pharmaceutical formulation may be administered to a patient in need of treatment via any suitable route. Routes of administration may include, for example, parenteral administration (including subcutaneous, intramuscular, intravenous, by means of, for example a drip patch). Further suitable routes of administration include (but are not limited to) oral, rectal, nasal, topical (including buccal and sublingual), infusion, vaginal, intradermal, intraperitoneally, intracranially, intrathecal and epidural administration or administration via oral or nasal inhalation, by means of, for example a nebulizer or inhaler, or by an implant.

A capture agent or pharmaceutical formulation may also be administered via microspheres, liposomes, other microparticulate delivery systems or sustained release formulations placed in certain tissues including blood. Suitable examples of sustained release carriers include semi-permeable polymer matrices in the form of shared articles, e.g., suppositories or microcapsules. Examples of the techniques and protocols mentioned above and other techniques and protocols which may be used in accordance with the invention can be found in Remington's Pharmaceutical Sciences, 18th edition, Gennaro, A. R., Lippincott Williams & Wilkins; 20th edition (Dec. 15, 2000) ISBN 0-912734-04-3 and Pharmaceutical Dosage Forms and Drug Delivery Systems; Ansel, N. C. et al. 7th Edition ISBN 0-683305-72-7, the entire disclosures of which are herein incorporated by reference.

Provided herein in certain embodiments is the use of the capture agents disclosed herein in the preparation of a medicament for treating a condition associated with increased target protein expression and/or activity.

In other more specific embodiments, the invention is directed to a method of detecting a target protein in a sample, the method comprising replacing an antibody or its equivalent in a cell-based or an immunoassay with any of the foregoing cyclic peptides. In some embodiments, the immunoassay is a Western blot, a pull-down assay, a dot blot or an ELISA.

In other embodiments, a method for inhibiting activity of a protein in a subject is provided, the method comprising administering an effective amount of any of the foregoing cyclic peptides to a subject in need thereof.

Other embodiments are directed to a method of purifying a target, the method comprising immobilizing any of the foregoing cyclic peptides in a column based format, contacting the column with a matrix containing the target, washing the column, and eluting the target.

Methods for imaging are also provided. For example, in one embodiment the invention provides a method of imaging in vivo target expression, the method comprising:
  a) providing any of the foregoing cyclic peptides, wherein SEQ is a peptide sequence having affinity for a location on or near a target expressing site in a subject, and modifying the cyclic peptide to include a small-molecule positron-emission-tomography ligand (PET ligand);
  b) administering the cyclic peptide of step a) to the subject;
  c) measuring the positron emission from the PET ligand at a first time;
  d) measuring the positron emission from the PET ligand at a second time; and
  e) comparing the positron emission from the PET ligand at the first and second times.

In certain embodiments of the foregoing, the PET ligand comprises a moiety selected from $^{64}$Cu DOTA, $^{68}$Ga DOTA, $^{68}$Ga NOTA, $^{18}$F, $^{64}$Cu, $^{68}$Ga, $^{89}$Zr $^{124}$I, $^{86}$Y, $^{94m}$Tc, $^{110m}$In, $^{11}$C and $^{76}$Br.

In other embodiments, the imaging method is a method of imaging in vivo target expression, the method comprising:
  a) providing any of the foregoing cyclic peptides, wherein SEQ is a peptide sequence having affinity for a location on or near a target expressing site in a subject, and modifying the cyclic peptide to include a small-molecule single-photon-emission-computed-tomography ligand (SPECT ligand);
  b) administering the cyclic peptide of step a) to the subject;
  c) measuring the photon emission from the SPECT ligand at a first time;
  d) measuring the photon emission from the SPECT ligand at a second time; and
  e) comparing the photon emission from the SPECT ligand at the first and second times.

In some embodiments of the foregoing, the SPECT ligand comprises a moiety selected from $^{111}$In DOTA, $^{90}$Y DOTA, $^{111}$In, $^{90}$Y and $^{99m}$Tc.

In other embodiments, a method of imaging in vivo target expression is provided, the method comprising:
  a) providing any of the foregoing cyclic peptides, wherein SEQ is a peptide sequence having affinity for a location on or near a target expressing site in a subject, and modifying the cyclic peptide to include a magnetic resonance ligand (MR ligand);

b) administering the cyclic peptide of step a) to the subject;

c) measuring the magnetic resonance from the MR ligand at a first time;

d) measuring the magnetic resonance from the MR ligand at a second time; and e) comparing the magnetic resonance from the MR ligand at the first and second times.

In some embodiments, the MR ligand comprises $Gd^{3+}$.

In other embodiments of the foregoing methods, the cyclic peptide comprises a linkage to a reporter moiety, the reporter moiety selected from polyethylene glycol (PEG), biotin, thiol and fluorophores. For example, in some embodiments the fluorophores are selected from FAM, FITC, Cy5, TRITC, TAMRA.

Disclosed herein are particular peptides that bind to CD8 (both CD8 protein and CD8 on CD8+ cells). Such peptides can be used in or as a capture agent and used as a capture agent or as a binding peptide in any of various methods for use of capture agents and binding peptides. These disclosed peptides include: t(Thz)pk(FP), t(PhF)Gk(FP), t(Thz)hkn (SEQ ID NO:2), t(Thz)(FP)kG, tG(PhF)k(N-Me-a), t(CyA)(PhF)kh, t(CyA)(FP)kn, t(N-Me-a)(N-Me-a)kn, t(N-Me-a)pke (SEQ ID NO:3), tphkn (SEQ ID NO:4), t(CyA)rks (SEQ ID NO:5), tpkk(N-Me-a) (SEQ ID NO:6), t(CyA)ek(N-Me-a), t(CyA)ekh (SEQ ID NO:7), t(CyA)tk(CyA), tesk(CyA) (SEQ ID NO:8), tetk(N-Me-a) (SEQ ID NO:9), tenk(FP) (SEQ ID NO:10), tekkp (SEQ ID NO:11), tskk(N-Me-a) (SEQ ID NO:12), ttrk (SEQ ID NO:13), tnkk(CyA) (SEQ ID NO:14), ts(Thz)k(CyA), tk(FP)kk (SEQ ID NO:15), trrk(CyA) (SEQ ID NO:16), trrks (SEQ ID NO:17), tkrkr (SEQ ID NO:18), trkkh (SEQ ID NO:19), trnkr (SEQ ID NO:20), ttkkr (SEQ ID NO:21), tshkr (SEQ ID NO:22), t(Thz)rkk (SEQ ID NO:23), tr(Thz)kr (SEQ ID NO:24), tr(FP)kr (SEQ ID NO:25), tk(FP)kr (SEQ ID NO:26), trGkr (SEQ ID NO:27), tG(CyA)kr (SEQ ID NO:28), tp(CyA)k(FP), te(MT)kp (SEQ ID NO:29), tnpks (SEQ ID NO:31), tp(CyA)k(FP), t(CyA/e/Thz)(k/FP)k(N-Me-a/n/FP), and trrkr (SEQ ID NO:30).

In some forms, the peptide can be t(Thz)pk(FP), t(PhF)Gk(FP), t(Thz)hkn (SEQ ID NO:2), t(Thz)(FP)kG, tG(PhF)k(N-Me-a), t(CyA)(PhF)kh, t(CyA)(FP)kn, t(N-Me-a)(N-Me-a)kn, t(N-Me-a)pke (SEQ ID NO:3), tphkn (SEQ ID NO:4), t(CyA)rks (SEQ ID NO:5), tpkk(N-Me-a) (SEQ ID NO:6), t(CyA)ek(N-Me-a), t(CyA)ekh (SEQ ID NO:7), t(CyA)tk(CyA), tesk(CyA) (SEQ ID NO:8), tetk(N-Me-a) (SEQ ID NO:9), tenk(FP) (SEQ ID NO:10), tekkp (SEQ ID NO:11), tskk(N-Me-a) (SEQ ID NO:12), ttrk (SEQ ID NO:13), tnkk(CyA) (SEQ ID NO:14), ts(Thz)k(CyA), tk(FP)kk (SEQ ID NO:15), trrk(CyA) (SEQ ID NO:16), trrks (SEQ ID NO:17), tkrkr (SEQ ID NO:18), trkkh (SEQ ID NO:19), trnkr (SEQ ID NO:20), ttkkr (SEQ ID NO:21), tshkr (SEQ ID NO:22), t(Thz)rkk (SEQ ID NO:23), tr(Thz)kr (SEQ ID NO:24), tr(FP)kr (SEQ ID NO:25), tk(FP)kr (SEQ ID NO:26), trGkr (SEQ ID NO:27), tG(CyA)kr (SEQ ID NO:28), tp(CyA)k(FP), te(MT)kp (SEQ ID NO:29), tnpks (SEQ ID NO:31), tp(CyA)k(FP), t(CyA/e/Thz)(k/FP)k(N-Me-a/n/FP), or trrkr (SEQ ID NO:30).

In some forms, the peptide can be t(Thz)pk(FP), t(PhF)Gk(FP), t(Thz)hkn (SEQ ID NO:2), t(Thz)(FP)kG, tG(PhF)k(N-Me-a), t(CyA)(PhF)kh, t(CyA)(FP)kn, t(N-Me-a)(N-Me-a)kn, t(N-Me-a)pke (SEQ ID NO:3), tphkn (SEQ ID NO:4), t(CyA)rks (SEQ ID NO:5), tpkk(N-Me-a) (SEQ ID NO:6), t(CyA)ek(N-Me-a), t(CyA)ekh (SEQ ID NO:7), t(CyA)tk(CyA), tesk(CyA) (SEQ ID NO:8), tetk(N-Me-a) (SEQ ID NO:9), tenk(FP) (SEQ ID NO:10), tekkp (SEQ ID NO:11), tskk(N-Me-a) (SEQ ID NO:12), ttrk (SEQ ID NO:13), tnkk(CyA) (SEQ ID NO:14), ts(Thz)k(CyA), or tk(FP)kk (SEQ ID NO:15).

In some forms, the peptide can be trrk(CyA) (SEQ ID NO:16), trrks (SEQ ID NO:17), tkrkr (SEQ ID NO:18), trkkh (SEQ ID NO:19), trnkr (SEQ ID NO:20), ttkkr (SEQ ID NO:21), tshkr (SEQ ID NO:22), t(Thz)rkk (SEQ ID NO:23), tr(Thz)kr (SEQ ID NO:24), tr(FP)kr (SEQ ID NO:25), tk(FP)kr (SEQ ID NO:26), trGkr (SEQ ID NO:27), tG(CyA)kr (SEQ ID NO:28), tp(CyA)k(FP), or te(MT)kp (SEQ ID NO:29).

In some forms, the peptide can be tnpks (SEQ ID NO:31) or tp(CyA)k(FP). In some forms, the peptide can be t(CyA/e/Thz)(k/FP)k(N-Me-a/n/FP), trrkr (SEQ ID NO:30), tnpks (SEQ ID NO:31), or tp(CyA)k(FP). In some forms, the peptide can be t(CyA/e/Thz)(k/FP)k(N-Me-a/n/FP), tnpks (SEQ ID NO:31), or tp(CyA)k(FP).

The disclosed compositions and methods can be further understood through the following numbered paragraphs.

1. A cyclic peptide having the following structure (I):

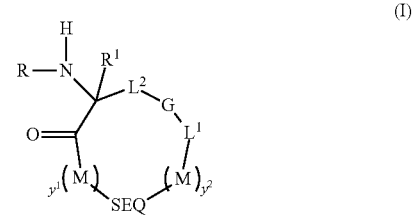

or a salt, tautomer, prodrug or stereoisomer thereof, wherein:

$L^1$ and $L^2$ are each individually optionally substituted linker moieties, each linker moiety optionally comprising a linkage to a solid support, a linkage to a reporter moiety, a linkage to a peptide ligand, a linkage to an azide or alkyne moiety or combinations thereof;

G is a triazole, a carbon-carbon double bond or an amide;

M is methionine;

R is H, -$L^3$-A or —C(=O)-$L^3$-A, where $L^3$ is a linker moiety and A is an alkyne, azide or a bond to a peptide ligand;

$R^1$ is H or $C_1$-$C_6$alkyl;

$Y^1$ and $Y^2$ are each individually 0 or 1; and

SEQ is an amino acid sequence comprising from 2 to 20 amino acids selected from a set of amino acids, wherein the set of amino acids comprises a combination of canonical amino acids and non-canonical amino acids, wherein two or more of the amino acids in the set are non-canonical amino acids and four or more of the amino acids in the set are canonical amino acids.

2. The cyclic peptide of paragraph 1, wherein G is a triazole.

3. The cyclic peptide of paragraph 1, wherein G is a carbon-carbon double bond.

4. The cyclic peptide of any one of paragraphs 1-3, wherein $L^1$, $L^2$, or both, comprise one or more substituents selected from alkyl, alkyne, azide and aminocarbonyl.

5. The cyclic peptide of any one of paragraphs 1-4, wherein $L^1$, $L^2$, or both, comprise a linkage selected from a linkage to a solid support, a linkage to a reporter moiety and a linkage to a peptide ligand.

6. The cyclic peptide of any one of paragraphs 1-5, wherein $L^1$ and $L^2$ are alkylene.

7. The cyclic peptide of any one of paragraphs 1-6, wherein the cyclic peptide has one of the following structures (Ia) or (Ib):

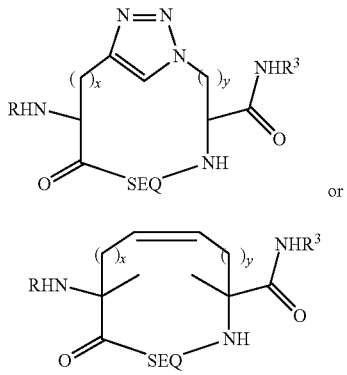

(Ia)

or (Ib)

wherein:
R³ is H, a linkage to a solid support, a linkage to a reporter moiety, a linkage to a peptide ligand, a linkage to an azide or alkyne moiety or combinations thereof; and
x and y are each independently an integer from 1 to 8.

8. The cyclic peptide of any one of paragraphs 1-7, wherein SEQ comprises from 2 to 9 amino acids.

9. The cyclic peptide of paragraph 8, wherein SEQ comprises from 5 to 7 amino acids.

10. The cyclic peptide of any one of paragraphs 1-9, wherein the amino acids are selected from Cyclopropyl Alanine (CyA), Gly, 4-Fluorophenyl Alanine (FP), Methyl Tryptophan (MT), 2-Methoxy Pyridylalanine (MeOPyr), 4-Phenyl Phenylalanine (PhF), Asn, Ser, Thr, His, Lys, Arg, Glu, (3-Phenylalanine (BPhA), N-Methyl d-alanine (N-Me-a), and Pro.

11. The cyclic peptide of any one of paragraphs 1-9, wherein the amino acids are selected from Cyclopropyl Alanine (CyA) and Gly; 4-Fluorophenyl Alanine (FP), Methyl Tryptophan (MT), Thiazolyl Alanine (Thz), 4-Phenyl Phenylalanine (PhF), and Phe; Asn, Ser, Thr; His, Lys, Arg, Glu; and N-Methyl d-alanine (N-Me-a), and Pro.

12. The cyclic peptide of any one of paragraphs 1-9, wherein the amino acids are selected from Cyclopropyl Alanine (CyA) and Gly; 4-Fluorophenyl Alanine (FP), Methyl Tryptophan (MT), 2-Methoxy Pyridylalanine (MeOPyr), Thiazolyl Alanine (Thz), 4-Phenyl Phenylalanine (PhF), and Phe; Asn, Ser, Thr; His, Lys, Arg, Glu; and β-Phenylalanine (BPhA), N-Methyl d-alanine (N-Me-a), and Pro.

13. The cyclic peptide of any one of paragraphs 1-9, wherein SEQ comprises t(Thz)pk(FP), t(PhF)Gk(FP), t(Thz)hkn (SEQ ID NO:2), t(Thz)(FP)kG, tG(PhF)k(N-Me-a), t(CyA)(PhF)kh, t(CyA)(FP)kn, t(N-Me-a)(N-Me-a)kn, t(N-Me-a)pke (SEQ ID NO:3), tphkn (SEQ ID NO:4), t(CyA)rks (SEQ ID NO:5), tpkk(N-Me-a) (SEQ ID NO:6), t(CyA)ek(N-Me-a), t(CyA)ekh (SEQ ID NO:7), t(CyA)tk(CyA), tesk(CyA) (SEQ ID NO:8), tetk(N-Me-a) (SEQ ID NO:9), tenk(FP) (SEQ ID NO:10), tekkp (SEQ ID NO:11), tskk(N-Me-a) (SEQ ID NO:12), ttrk (SEQ ID NO:13), tnkk(CyA) (SEQ ID NO:14), ts(Thz)k(CyA), tk(FP)kk (SEQ ID NO:15), trrk(CyA) (SEQ ID NO:16), trrks (SEQ ID NO:17), tkrkr (SEQ ID NO:18), trkkh (SEQ ID NO:19), trnkr (SEQ ID NO:20), ttkkr (SEQ ID NO:21), tshkr (SEQ ID NO:22), t(Thz)rkk (SEQ ID NO:23), tr(Thz)kr (SEQ ID NO:24), tr(FP)kr (SEQ ID NO:25), tk(FP)kr (SEQ ID NO:26), trGkr (SEQ ID NO:27), tG(CyA)kr (SEQ ID NO:28), tp(CyA)k(FP), te(MT)kp (SEQ ID NO:29), tnpks (SEQ ID NO:31), tp(CyA)k(FP), t(CyA/e/Thz)(k/FP)k(N-Me-a/n/FP), or trrkr (SEQ ID NO:30).

14. The cyclic peptide of any one of paragraphs 1-13, wherein R is H or —C(=O)-L³-A, where L³ is a linker moiety and A is a bond to a peptide ligand or an alkyne.

15. The cyclic peptide of paragraph 14, wherein A is an alkyne.

16. The cyclic peptide of paragraph 14, wherein A is a bond to a peptide ligand.

17. The cyclic peptide of paragraph 16, wherein the peptide ligand is a linear peptide.

18. The cyclic peptide of paragraph 16, wherein the peptide ligand is a cyclic peptide.

19. The cyclic peptide of paragraph 17 or 18, wherein the peptide ligand further comprises a second peptide ligand covalently bound thereto.

20. The cyclic peptide of any one of paragraphs 1-19, wherein y¹ and y² are each 0.

21. A composition comprising the cyclic peptide of any one of paragraphs 1-20 and a pharmaceutically acceptable carrier.

22. A library comprising a plurality of cyclic peptides according to any one of paragraphs 1-20.

23. A method for identifying a target binding compound, the method comprising:
(A) providing a first peptide library comprising a plurality of first peptide library members, the first peptide library members optionally comprising an alkyne, azide or reporter moiety or combinations thereof;
(B) contacting the first peptide library with a target or a truncated analogue thereof, the target or truncated analogue thereof comprising a first binding site and optionally an alkyne, azide or reporter moiety or combinations thereof;
(C) identifying a first peptide library member with affinity for the first binding site and optionally modifying the first peptide library member to include an alkyne or azide moiety;
and optionally:
(D) providing a second peptide library comprising a plurality of second peptide library members, the second peptide library members comprising an azide or alkyne or both;
(E) contacting the second peptide library with a composition comprising the target or truncated analogue thereof and the first peptide library member of step C;
(F) forming a triazole-linked conjugate between the first peptide library member of step C and a second peptide library member, the second peptide library member having affinity for a second binding site on the target or truncated analogue thereof,
wherein the first peptide library, the second peptide library, or both, comprise cyclic peptides comprising:
(i) a sequence region comprising amino and carboxy termini and a variable peptide sequence of two to twenty amino acids selected from a set of amino acids, wherein the set of amino acids comprises a combination of canonical amino acids and non-canonical amino acids, wherein two or more of the amino acids in the set are non-canonical amino acid and four or more of the amino acids in the set are canonical amino acids; and
(ii) a linker region comprising a α-amino carbonyl, α-amido carbonyl, a methionine amino acid, or combinations thereof, and optionally comprising an alkyne, an azide, a linkage to a solid support or a linkage to a reporter moiety or a combination thereof, the linker region covalently linking the amino and carboxy termini of the sequence region.

24. The method of paragraph 23, wherein the linker region comprises a α-amino carbonyl group bound to the amino terminus of the peptide sequence.

25. The method of paragraph 24, further comprising determining the peptide sequence of one or more of the cyclic peptides by Edman degradation.

26. The method of paragraph 25, wherein the linker region comprises a methionine amino acid bound to the amino terminus of the variable peptide sequence.

27. The method of paragraph 26 further comprising treating one or more of the cyclic peptides with CNBr and determining the sequence thereof by mass spectrometry.

28. The method of paragraph 23, wherein the linker region comprises an alkyne or azide, the target or a truncated analogue thereof comprises an alkyne or azide and identifying the first peptide library member with affinity for the first binding site comprises identifying first peptide library members which form a triazole linkage with the target or a truncated analogue thereof.

29. The method of any one of paragraphs 23-28, wherein the first peptide library is contacted with a truncated analogue of the target.

30. The method of any one of paragraphs 23-29, further comprising modifying the triazole linked conjugate to contain a triazole or alkyne and contacting the modified conjugate with the target or truncated analogue thereof and a third peptide library, the third peptide library comprising a plurality of third peptide library members, each third peptide library member comprising an azide or alkyne.

31. The method of paragraph 30, further comprising forming a triazole linkage between the modified conjugate and a member of the third peptide library, the third peptide library member having affinity for a third binding site on the target or truncated analogue thereof.

32. The method of any one of paragraphs 23-31, wherein the first binding site is an epitope.

33. The method of any one of paragraphs 23-32, wherein the second binding site is an epitope.

34. The method of any one of paragraphs 23-33, wherein the third binding site is an epitope.

35. The method of any one of paragraphs 23-34, wherein the linker region comprises a carbon-carbon double bond or a triazole.

36. The method of any one of paragraphs 23-35, wherein the cyclic peptides have the following structure (I'):

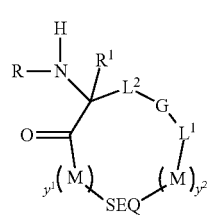

or a salt, tautomer or stereoisomer thereof, wherein:
$L^1$ and $L^2$ are each individually optionally substituted linker moieties, each linker moiety optionally comprising a linkage to a solid support, a linkage to a reporter moiety, a linkage to an azide or alkyne moiety or combinations thereof;
G is a triazole a carbon-carbon double bond or an amide;
M is methionine;
R is H, $-L^3$-A or $—C(=O)-L^3$-A, where $L^3$ is a linker moiety and A is an alkyne or azide;
$R^1$ is H or $C_1$-$C_6$alkyl; $Y^1$ and $Y^2$ are each individually 0 or 1; and
SEQ is the variable peptide sequence.

37. The method of paragraph 36, wherein SEQ comprises from 2 to 9 amino acids.

38. The method of paragraph 37, wherein SEQ comprises from 5 to 7 amino acids.

39. The method of any one of paragraphs 26-38, wherein the amino acids are selected from Cyclopropyl Alanine (CyA), Gly, 4-Fluorophenyl Alanine (FP), Methyl Tryptophan (MT), 2-Methoxy Pyridylalanine (MeOPyr), 4-Phenyl Phenylalanine (PhF), Asn, Ser, Thr, His, Lys, Arg, Glu, (3-Phenylalanine (BPhA), N-Methyl d-alanine (N-Me-a), and Pro.

40. The method of any one of paragraphs 26-38, wherein the amino acids are selected from Cyclopropyl Alanine (CyA) and Gly; 4-Fluorophenyl Alanine (FP), Methyl Tryptophan (MT), Thiazolyl Alanine (Thz), 4-Phenyl Phenylalanine (PhF), and Phe; Asn, Ser, Thr; His, Lys, Arg, Glu; and N-Methyl d-alanine (N-Me-a), and Pro.

41. The method of any one of paragraphs 26-38, wherein the amino acids are selected from Cyclopropyl Alanine (CyA) and Gly; 4-Fluorophenyl Alanine (FP), Methyl Tryptophan (MT), 2-Methoxy Pyridylalanine (MeOPyr), Thiazolyl Alanine (Thz), 4-Phenyl Phenylalanine (PhF), and Phe; Asn, Ser, Thr; His, Lys, Arg, Glu; and β-Phenylalanine (BPhA), N-Methyl d-alanine (N-Me-a), and Pro.

42. The method of any one of paragraphs 26-38, wherein SEQ comprises t(Thz)pk(FP), t(PhF)Gk(FP), t(Thz)hkn (SEQ ID NO:2), t(Thz)(FP)kG, tG(PhF)k(N-Me-a), t(CyA)(PhF)kh, t(CyA)(FP)kn, t(N-Me-a)(N-Me-a)kn, t(N-Me-a)pke (SEQ ID NO:3), tphkn (SEQ ID NO:4), t(CyA)rks (SEQ ID NO:5), tpkk(N-Me-a) (SEQ ID NO:6), t(CyA)ek(N-Me-a), t(CyA)ekh (SEQ ID NO:7), t(CyA)tk(CyA), tesk(CyA) (SEQ ID NO:8), tetk(N-Me-a) (SEQ ID NO:9), tenk(FP) (SEQ ID NO:10), tekkp (SEQ ID NO:11), tskk(N-Me-a) (SEQ ID NO:12), ttrk (SEQ ID NO:13), tnkk(CyA) (SEQ ID NO:14), ts(Thz)k(CyA), tk(FP)kk (SEQ ID NO:15), trrk (CyA) (SEQ ID NO:16), trrks (SEQ ID NO:17), tkrkr (SEQ ID NO:18), trkkh (SEQ ID NO:19), trnkr (SEQ ID NO:20), ttkkr (SEQ ID NO:21), tshkr (SEQ ID NO:22), t(Thz)rkk (SEQ ID NO:23), tr(Thz)kr (SEQ ID NO:24), tr(FP)kr (SEQ ID NO:25), tk(FP)kr (SEQ ID NO:26), trGkr (SEQ ID NO:27), tG(CyA)kr (SEQ ID NO:28), tp(CyA)k(FP), te(MT)kp (SEQ ID NO:29), tnpks (SEQ ID NO:31), tp(CyA)k(FP), t(CyA/e/Thz)(k/FP)k(N-Me-a/n/FP), or trrkr (SEQ ID NO:30).

43. The method of any one of paragraphs 23-42, wherein the cyclic peptides have the following structure (I'a):

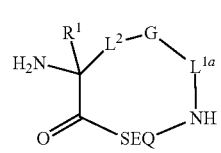

wherein:
L¹ᵃ is a linker moiety optionally substituted with one or more substituents selected from a linkage to an alkyne or azide moiety, a linkage to a solid support and a linkage to a reporter moiety.

44. The method of paragraph 43, wherein L¹ᵃ and L² are each independently optionally substituted alkylene.

45. The method of any one of paragraphs 23-44, wherein the cyclic peptides have the following structure (I'b):

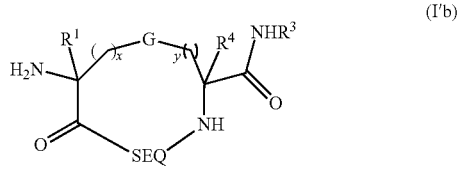

wherein:
R³ is H, a linkage to a solid support, a linkage to an alkyne or azide moiety or a linkage to a reporter moiety;
R⁴ is H or $C_1$-$C_6$alkyl; and
x and y are each independently integers from 1 to 8.

46. The method of any one of paragraphs 36-45, wherein G is a triazole.

47. The method of any one of paragraphs 36-45, wherein G is a carbon-carbon double bond.

48. The method of paragraph 36, wherein the cyclic peptides have one of the following structures:

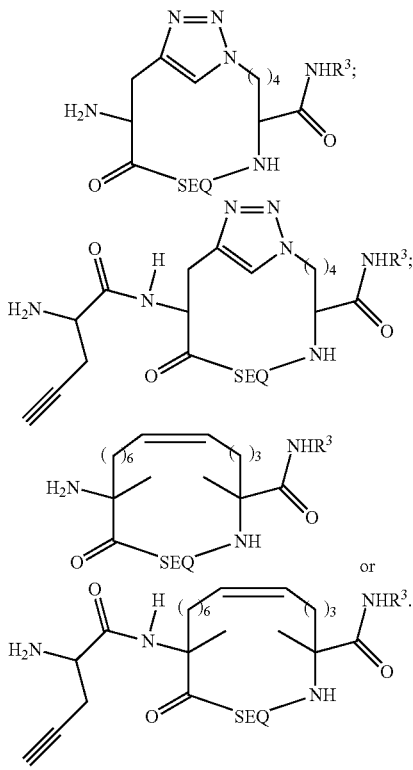

49. The method of any one of paragraphs 23-48, wherein the first peptide library comprises the cyclic peptides, and the second peptide library comprises linear peptide members.

50. The method of any one of paragraphs 23-48, wherein the second peptide library comprises the cyclic peptides, and the first peptide library comprises linear peptide members.

51. The method of any one of paragraphs 23-48, wherein the first and second peptide library comprises the cyclic peptides.

52. The method of any one of paragraphs 23-48, wherein the target is a protein.

53. The method of paragraph 52, wherein the protein is an enzyme or cell surface protein.

54. A method of detecting a target protein in a sample, the method comprising replacing an antibody or its equivalent in a cell-based or an immunoassay with the cyclic peptide of any one of paragraphs 1-20.

55. The method of paragraph 54, wherein the immunoassay is a Western blot, a pull-down assay, a dot blot or an ELISA.

56. A method for inhibiting activity of a protein in a subject, the method comprising administering an effective amount of the cyclic peptide of any one of paragraphs 1-20 to a subject in need thereof.

57. A method of purifying a target, the method comprising immobilizing the cyclic peptide of any one of paragraphs 1-20 in a column based format, contacting the column with a matrix containing the target, washing the column, and eluting the target.

58. A method of imaging in vivo target expression, the method comprising:
(a) providing a cyclic peptide of any one of paragraphs 1-20, wherein SEQ is a peptide sequence having affinity for a location on or near a target expressing site in a subject, and modifying the cyclic peptide to include a small-molecule positron-emission-tomography ligand (PET ligand);
(b) administering the cyclic peptide of step (a) to the subject;
(c) measuring the positron emission from the PET ligand at a first time;
(d) measuring the positron emission from the PET ligand at a second time; and
(e) comparing the positron emission from the PET ligand at the first and second times.

59. The method of paragraph 58, wherein the PET ligand comprises a moiety selected from $^{64}$Cu DOTA, $^{68}$Ga DOTA, $^{68}$Ga NOTA, $^{18}$F, $^{64}$Cu, $^{68}$Ga, $^{89}$Zr, $^{124}$I, $^{86}$Y, $^{94m}$Tc, $^{110m}$In, $^{11}$C and $^{76}$Br.

60. A method of imaging in vivo target expression, the method comprising:
(a) providing a cyclic peptide of any one of paragraphs 1-20, wherein SEQ is a peptide sequence having affinity for a location on or near a target expressing site in a subject, and modifying the cyclic peptide to include a small-molecule single-photon-emission-computed-tomography ligand (SPECT ligand);
(b) administering the cyclic peptide of step (a) to the subject; (c) measuring the photon emission from the SPECT ligand at a first time;
(d) measuring the photon emission from the SPECT ligand at a second time; and
(e) comparing the photon emission from the SPECT ligand at the first and second times.

61. The method of paragraph 60, wherein the SPECT ligand comprises a moiety selected from $^{111}$In DOTA, $^{90}$Y DOTA, $^{111}$In, $^{90}$Y and $^{99m}$Tc.

62. A method of imaging in vivo target expression, the method comprising:

(a) providing a cyclic peptide of any one of paragraphs 1-20, wherein SEQ is a peptide sequence having affinity for a location on or near a target expressing site in a subject, and modifying the cyclic peptide to include a magnetic resonance ligand (MR ligand);
(b) administering the cyclic peptide of step (a) to the subject; (c) measuring the magnetic resonance from the MR ligand at a first time;
(d) measuring the magnetic resonance from the MR ligand at a second time; and
(e) comparing the magnetic resonance from the MR ligand at the first and second times.

63. The method of paragraph 62, wherein the MR ligand comprises $Gd^{3+}$.

64. The cyclic peptide of any one of paragraphs 1-20 or the method of any one of paragraphs 26-63, wherein the cyclic peptide comprises a linkage to a reporter moiety, the reporter moiety selected from polyethylene glycol (PEG), biotin, thiol and fluorophores.

65. The cyclic peptide or method of paragraph 64, wherein the fluorophores are selected from carboxyfluorescein (FAM), fluorescein isothiocyanate (FITC), Cyanine-5 (Cy5), tetramethylrhodamine (TRITC) and Carboxytetramethylrhodamine (TAMRA).

EXAMPLES

Example 1: Synthesis of Ring Closing Metathesis (RCM) Catalyzed OBOC Peptide Libraries

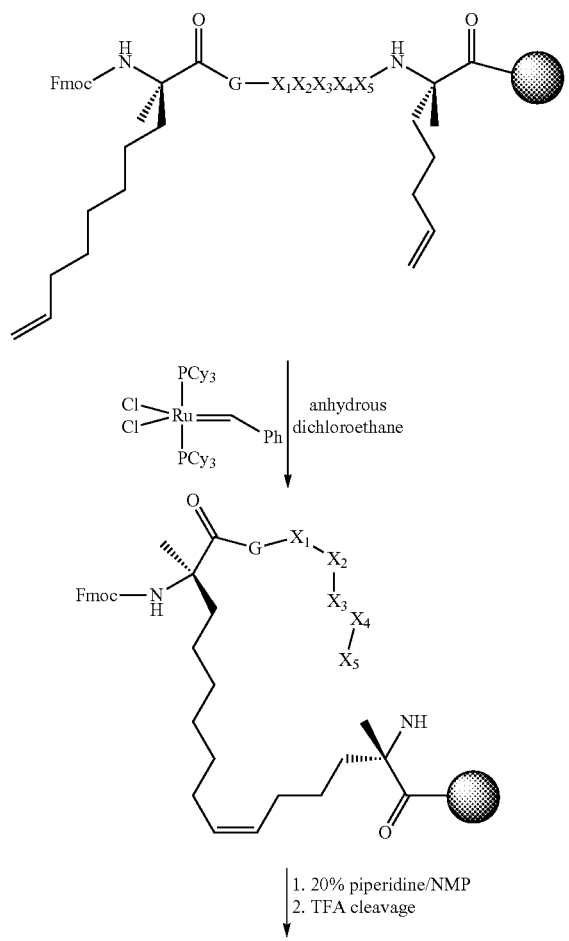

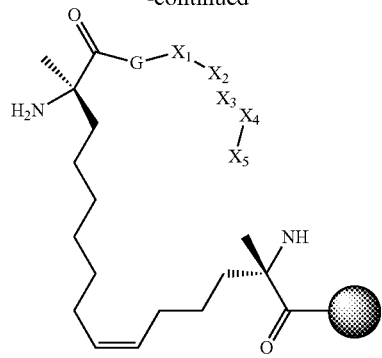

A linear library of the form Fmoc-R-$I_8$-G-$X_1X_2X_3X_4X_5$-S-$I_5$-TG, (R-$I_8$=R-2-amino-2methyldec-9-enoic acid), TG=Tentagel-S-$NH_2$ resin, S—$I_5$=S-2-amino-2methyldec-9-enoic acid, and Xi=D-Ala, D-Arg, D-Asn, D-Asp, D-Glu, D-Gln, Gly, D-His, D-Ile, D-Leu, D-Lys, D-Phe, D-Pro, D-D-Thr, D-Trp, D-Tyr, D-Val) was synthesized using standard solid phase techniques. The amino acid after S-$I_5$ was double coupled using standard SPPS protocols, to maintain the efficiency of the coupling step. The amino acid pair R-$I_8$ and S-$I_5$ were chosen for the RCM reaction, since R-$I_8$ and S-$I_5$, separated by 6 amino acids in a helical peptide, provides very effective crosslinking (98% yield). While a majority of the randomized OBOC peptides will not be of a helical form, the long alkyl cross linker (total 13 atoms) should enable the peptides to cyclize on bead via RCM. The on bead peptides were cyclized using Grubb's catalyst, bis(tricyclohexylphosphine)benzylidine ruthenium(IV) dichloride according to literature methods. Briefly, in an argon atmosphere, the peptide library R-$I_8$-G-$X_1X_2X_3X_4X_5$-S-$I_5$-TG was swelled for 30 minutes in anhydrous dichloroethane solution. 1 ml of 10 mM solution of the Grubb's catalyst in dichloroethane was added to the swelled resin and the reaction was allowed to proceed for 6 hours. The solution was drained and the reaction with the catalyst was repeated again for 6 hours. The library was washed with anhydrous dichloroethane and the excess catalyst was removed using oxine in DMF. The Fmoc group was removed by treatment with 20% piperidine/NMP. The library was washed and dried and the side chains were deprotected by treatment with 95:2.5:2.5 TFA/TES/$H_2O$. The final cyclized library was stored in TBS buffer.

Example 2: Synthesis of Triazole Cyclized OBOC Libraries

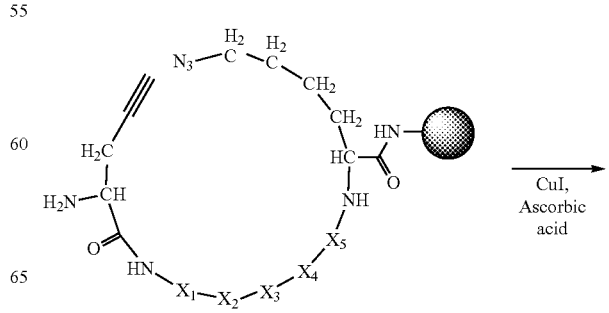

-continued

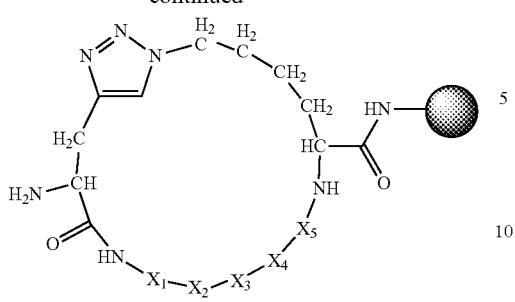

The linear peptide libraries A, B, C were synthesized on Tentagel-S-NH$_2$ resin using standard SPPS library synthesis methods. Libraries B and C were synthesized at a 10-fold excess to ensure adequate representation of each library element. After the synthesis of each library, all the beads in the linear library were subjected to an on bead CuAAC reaction, for 6 hours at room temperature with 1.5 equivalents of CuI, 2.5 equivalents of ascorbic acid in 20% piperidine in DMF. After washes with 10% sodium diethyldithiocarbamate in DMF to remove the adsorbed Cu, the library was washed with DMF, methanol and DCM and dried. Random beads were picked from the library to be sequenced. The rest of the library was stored in NMP until used.

Example 3: Synthesis of Triazole Cyclized OBOC Libraries

A panel of D and L non-canonical amino acids were obtained to enable standard solid phase peptide synthesis of OBOC libraries with diversified side chains (Table 2). These new amino acids incorporate additional steric compression (methylated amino acids), electronically modulated phenyl substituents, and various heterocycles. Homologated amino acids including beta amino acids were included to add additional flexibility to the peptide macrocycle. Finally, natural amino acids with metabolic liabilities (i.e. tyrosine and tryptophan) were replaced with robust derivatives. Test sequences were prepared to ensure that the unnatural amino acid could be incorporated using standard peptide coupling conditions during the split/mix library synthesis. These test sequences were also sequenced by MALDI-TOF/TOF mass spectrometry to ensure the amino acids were sequenceable.

TABLE 2

Panel of Non-Canonical Amino Acids

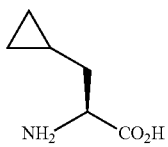

CyA
Cyclopropyl Alanine
Exact Mass: 129.08
Molecular Weight: 129.16

TABLE 2-continued

Panel of Non-Canonical Amino Acids

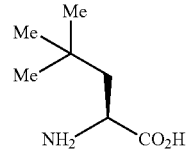

MeL
Methyl Leucine
Exact Mass: 145.11
Molecular Weight: 145.20

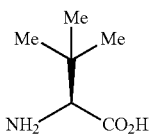

MeV
Methyl valine
Exact Mass: 131.09
Molecular Weight: 131.18

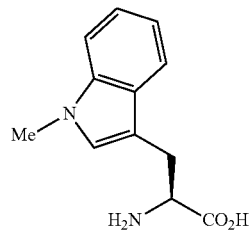

MT
Methyl Tryptophan
Exact Mass: 218.11
Molecular Weight: 218.26

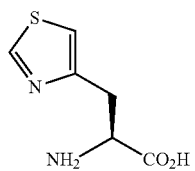

Thz
Thiazolyl-Ala
Exact Mass: 172.03
Molecular Weight: 172.20

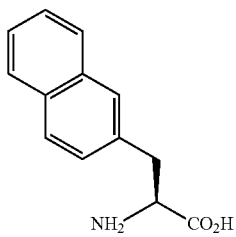

Nap
2-Naphthyl Alanine
Exact Mass: 215.09
Molecular Weight: 215.25

TABLE 2-continued

Panel of Non-Canonical Amino Acids

OMY
O-Methyl Tyrosine
Exact Mass: 195.09
Molecular Weight: 195.22

FP
4-Fluorophenyl Alanine
Exact Mass: 183.07
Molecular Weight: 183.18

CN-F
4-Cyano phenylalanine
Exact Mass: 190.07
Molecular Weight: 190.20

Br—F
4-Bromo phenylalanine
Exact Mass: 242.99
Molecular Weight: 244.09

Me—F
4-Methyl phenylalanine
Exact Mass: 179.09
Molecular Weight: 179.22

OPhY
O-PhenylTyrosine
Exact Mass: 257.11
Molecular Weight: 257.29

PyrA
4-Pyridyl Alanine
Exact Mass: 166.07
Molecular Weight: 166.18

PhF
4-Phenyl phenylalanine
[199110-64-0]
Chem-Impex; 04084
Exact Mass: 241.11
Molecular Weight: 241.29

DMK
Dimethyl-Lys
Exact Mass: 174.14
Molecular Weight: 174.24

Ttz
Tetrazolyl Alanine
Exact Mass: 157.06
Molecular Weight: 157.13

TABLE 2-continued

Panel of Non-Canonical Amino Acids

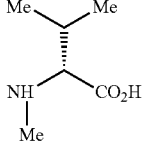

N—Me-v
N-Methyl d-Valine
Exact Mass: 131.09
Molecular Weight: 131.18

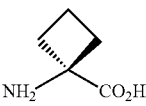

ACBC
Aminocyclobutyl
carboxylic acid
Exact Mass: 115.06
Molecular Weight: 115.13

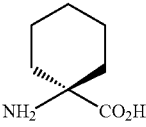

ACHC
Aminocyclohexyl
carboxylic acid
Exact Mass: 143.09
Molecular Weight: 143.19

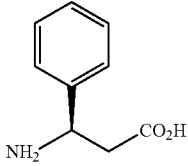

BPhA
β-Phenylalanine
[220498-02-2]
Chem-Impex: 12848
Exact Mass: 165.08
Molecular Weight: 165.19

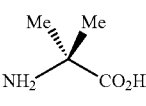

AMA
alpha-Methylalanine
Exact Mass: 103.06
Molecular Weight: 103.12

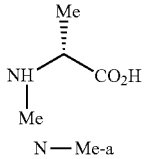

N—Me-a
N-Methyl d-alanine
Exact Mass: 103.06
Molecular Weight: 103.12

TABLE 2-continued

Panel of Non-Canonical Amino Acids

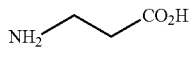

BAla
β-Alanine
Exact Mass: 89.05
Molecular Weight: 89.09

Several of these non-canonical amino acids were included in a focused library (Table 4; Set 2) to improve a previous hit, tfpkk (SEQ ID NO:1). The threonine in the first position and lysine in the fourth position were found to be critical for target binding (CD8). The three other positions sampled the 16 amino acids listed in Table 4, randomly including one of the 16 amino acids at each of the second, third, and fifth positions. Tyrosine was removed from the library and replaced with additional aromatic non-canonical amino acids including 4-fluorophenyl alanine and 4-phenyl phenylalanine. Tryptophan's metabolic liability was addressed by methylation of the indole N—H. The thiazolyl derivative is a histidine derivative, replacing the hydrogen bond donation of histidine with a polarizable thio-heterocycle. Cyclopropyl alanine, a cyclic derivative of valine was included to sample this compressed derivative. An N-methylated amino acid, N-methylalanine was included to provide hits with enhanced flexibility. Together, the inclusion of non-canonical amino acids greatly increased the chemical diversity and bioactivity of the resulting peptides. This library has $16^3=4096$ unique species (1 g=700 copies).

TABLE 4

Focused Library including Non-Canonical Amino Acids

Hydrophobic Side Chain - Aliphatic

CyA
Cyclopropyl Alanine
Exact Mass: 129.08
Molecular Weight: 129.16

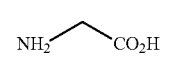

Gly
Glycine
Exact Mass: 75.03
Molecular Weight: 75.07

Hydrophobic Side Chain - Aromatic

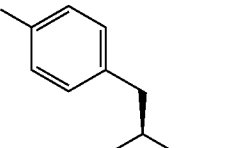

FP
4-Fluorophenyl Alanine
Exact Mass: 183.07
Molecular Weight: 183.18

TABLE 4-continued

Focused Library including Non-Canonical Amino Acids

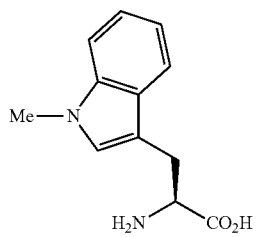

MT
Methyl Tryptophan
Exact Mass: 218.11
Molecular Weight: 218.26

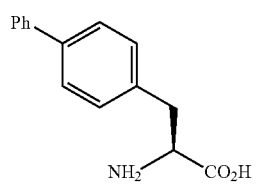

PhF
4-Phenyl phenylalanine
[199110-64-0]
Chem-Impex; 04084
Exact Mass: 241.11
Molecular Weight: 241.29

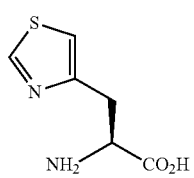

Thz
Thiazolyl-Ala
Exact Mass: 172.03
Molecular Weight: 172.20

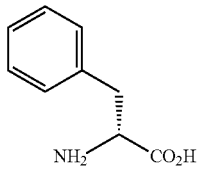

Phe
Phenyl alanine
Exact Mass: 165.08
Molecular Weight: 165.19

Polar Side Chain - Neutral

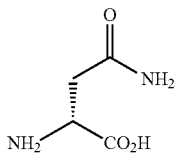

Asn
Asparagine
Exact Mass: 132.05
Molecular Weight: 132.12

TABLE 4-continued

Focused Library including Non-Canonical Amino Acids

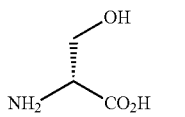

Ser
Serine
Exact Mass: 105.04
Molecular Weight: 105.09

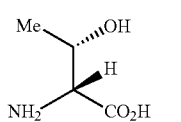

Thr
Threonine
Exact Mass: 119.06
Molecular Weight: 119.12

Polar Side Chain - Charged

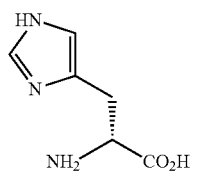

His
Histidine
Exact Mass: 155.07
Molecular Weight: 155.16

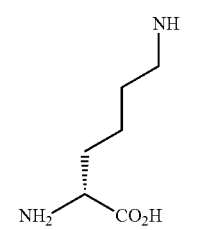

Lys
Lysine
Exact Mass: 146.11
Molecular Weight: 146.19

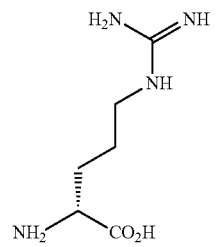

Arg
Arginine
Exact Mass: 174.11
Molecular Weight: 174.20

TABLE 4-continued

Focused Library including Non-Canonical Amino Acids

Glu
Glutamic Acid
Exact Mass: 147.05
Molecular Weight: 147.13

Conformational Perturbation

N—Me-a
N-Methyl d-alanine
Exact Mass: 103.06
Molecular Weight: 103.12

Pro
Proline
Exact Mass: 115.06
Molecular Weight: 115.13

This focused library entered into a screen to identify enhanced CD8 binders. Non-specific PCCs were identified and removed from the library by performing an anti-screen against the glycosylated cell-surface protein PSMA. The enriched library was then screened against CD8a, yielding 23 hits (Table 5). These hits display good homology, suggesting tractable structure-activity-relationship among the hits. Each non-canonical amino acid was represented at least once among the hits, with the exception of 1-methyltryptophan. The consensus sequence from the hits in Table 5 is t(CyA/e/Thz)(k/FP)k(N-Me-a/n/FP).

TABLE 5

Hit Sequences Following CD8 Protein Screen

| x1 | x2 | x3 | x4 | x5 | SEQ ID NO |
|----|----|----|----|----|-----------|
| t  | Thz | p | k | FP | |
|    | PhF | G |   | FP | |
|    | Thz | h |   | n  | 2 |
|    | Thz | FP |  | G  |   |
|    | G   | PhF | | N-Me-a | |
|    | CyA | PhF | | h   |   |
|    | CyA | FP  | | n   |   |
|    | N-Me-a | N-Me-a | | n | |
|    | N-Me-a | p  | | e   | 3 |
|    | p   | h   | | n   | 4 |
|    | CyA | r   | | s   | 5 |
|    | p   | k   | | N-Me-a | 6 |
|    | CyA | e   | | N-Me-a |   |
|    | CyA | e   | | h   | 7 |
|    | CyA | t   | | CyA |   |
|    | e   | s   | | CyA | 8 |
|    | e   | t   | | N-Me-a | 9 |
|    | e   | n   | | FP  | 10 |
|    | e   | k   | | p   | 11 |
|    | s   | k   | | N-Me-1 | 12 |
|    | t   | r   | | —   | 13 |
|    | n   | k   | | CyA | 14 |
|    | s   | Thz | | CyA |   |
|    | k   | FP  | | k   | 15 |

In addition to screening the focused library against recombinant human CD8 protein, the library was screened against cells. Non-specific PCCs were identified and removed by an anti-screen against CD8− Jurkat cells. The pre-cleared library entered into a screen against CD8+ SupT1 cells in 2% FBS for 1 h at 4° C. The resulting hits (Table 6) showed a high level of sequence homology, with electrostatic side chains dominating the hit profile. Non-canonical amino acids including cyclopropyl alanine, thiazolyl alanine, 4-fluorophenylalanine, and 1-methyltryptophan were identified among the hits. The consensus sequence from the hits in Table 6 is trrkr (SEQ ID NO:30).

Because of the large number of electrostatic hits in the screen with 2% FBS, additional screens were performed varying the blocking conditions to decrease the quantity of electrostatic hits. In particular, screens using 10% FBS gave no hits with any electrostatic amino acids. These conditions ultimately identified tnpks (SEQ ID NO:31) and tp(CyA)k (Fp).

TABLE 6

Hit Sequences Following CD8+ Cell Screen

| x1 | x2 | x3 | x4 | x5 | SEQ ID NO |
|----|----|----|----|----|-----------|
| t | r | r | k | CyA | 16 |
| t | r | r | k | s | 17 |
| t | k | r | k | r | 18 |
| t | r | k | k | h | 19 |
| t | r | n | k | r | 20 |
| t | t | k | k | r | 21 |
| t | s | h | k | r | 22 |
| t | Thz | r | k | k | 23 |
| t | r | Thz | k | r | 24 |
| t | r | FP | k | r | 25 |
| t | k | FP | k | r | 26 |
| t | r | G | k | r | 27 |
| t | G | CyA | k | r | 28 |
| t | p | CyA | k | FP | |
| t | e | MT | k | P | 29 |

The hits identified in the non-canonical screen were further evaluated in CD8+ SupT1 and CD8− Jurkat cells by flow cytometry. Each hit displayed preferential binding to the CD8+ cell line. Additionally, tp(CyA)k(FP) demonstrated improved binding to CD8 over the parent compound tfpkk (SEQ ID NO:1) (FIG. 1).

Any of these identified peptides can be used in or as a capture agent and used as a capture agent or as a binding peptide in any of various methods for use of capture agents and binding peptides.

It is understood that the disclosed method and compositions are not limited to the particular methodology, protocols, and reagents described as these can vary. It is also to be understood that the terminology used herein is for the purpose of describing particular embodiments only, and is not intended to limit the scope of the present invention which will be limited only by the appended claims.

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a peptide is disclosed and discussed and a number of modifications that can be made to a number of molecules including the peptide are discussed, each and every combination and permutation of peptide and the modifications that are possible are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, is this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. Further, each of the materials, compositions, components, etc. contemplated and disclosed as above can also be specifically and independently included or excluded from any group, subgroup, list, set, etc. of such materials. These concepts apply to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

It must be noted that as used herein and in the appended claims, the singular forms "a", "an", and "the" include plural reference unless the context clearly dictates otherwise. Thus, for example, reference to "a peptide" includes a plurality of such peptides, reference to "the peptide" is a reference to one or more peptides and equivalents thereof known to those skilled in the art, and so forth.

"Optional" or "optionally" means that the subsequently described event, circumstance, or material may or may not occur or be present, and that the description includes instances where the event, circumstance, or material occurs or is present and instances where it does not occur or is not present.

Unless the context clearly indicates otherwise, use of the word "can" indicates an option or capability of the object or condition referred to. Generally, use of "can" in this way is meant to positively state the option or capability while also leaving open that the option or capability could be absent in other forms or embodiments of the object or condition referred to. Unless the context clearly indicates otherwise, use of the word "may" indicates an option or capability of the object or condition referred to. Generally, use of "may" in this way is meant to positively state the option or capability while also leaving open that the option or capability could be absent in other forms or embodiments of the object or condition referred to. Unless the context clearly indicates otherwise, use of "may" herein does not refer to an unknown or doubtful feature of an object or condition.

Ranges can be expressed herein as from "about" one particular value, and/or to "about" another particular value. When such a range is expressed, also specifically contemplated and considered disclosed is the range from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. It should be understood that all of the individual values and sub-ranges of values contained within an explicitly disclosed range are also specifically contemplated and should be considered disclosed unless the context specifically indicates otherwise. Finally, it should be understood that all ranges refer both to the recited range as a range and as a collection of individual numbers from and including the first endpoint to and including the second endpoint. In the latter case, it should be understood that any of the individual numbers can be selected as one form of the quantity, value, or feature to which the range refers. In this way, a range describes a set of numbers or values from and including the first endpoint to and including the second endpoint from which a single member of the set (i.e. a single number) can be selected as the quantity, value, or feature to which the range refers. The foregoing applies regardless of whether in particular cases some or all of these embodiments are explicitly disclosed.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents. It will be clearly understood that, although a number of publications are referred to herein, such reference does not constitute an admission that any of these documents forms part of the common general knowledge in the art.

Although the description of materials, compositions, components, steps, techniques, etc. can include numerous options and alternatives, this should not be construed as, and is not an admission that, such options and alternatives are equivalent to each other or, in particular, are obvious alternatives. Thus, for example, a list of different amino acids does not indicate that the listed amino acids are obvious one to the other, nor is it an admission of equivalence or obviousness.

Every peptide disclosed herein is intended to be and should be considered to be specifically disclosed herein. Further, every subgroup that can be identified within this disclosure is intended to be and should be considered to be specifically disclosed herein. As a result, it is specifically contemplated that any peptide, or subgroup of peptides can be either specifically included for or excluded from use or included in or excluded from a list of peptides.

Those skilled in the art will recognize many equivalents to the specific embodiments of the method and compositions described herein. Such equivalents are intended to be encompassed by the following claims.

I claim:

1. A cyclic peptide having the following structure (I):

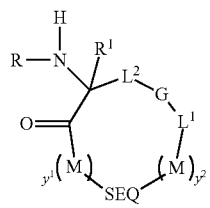

(I)

or a salt, tautomer, prodrug or stereoisomer thereof, wherein:
- $L^1$ and $L^2$ are each individually optionally substituted linker moieties, each linker moiety optionally comprising a linkage to a solid support, a linkage to a reporter moiety, a linkage to a peptide ligand, a linkage to an azide or alkyne moiety, or combinations thereof;
- G is a triazole;
- M is absent or methionine;
- R is H, -$L^3$-A or —C(=O)-$L^3$-A, where $L^3$ is a linker moiety and A is an alkyne, azide, or a bond to a peptide ligand;
- $R^1$ is H or $C_1$-$C_6$ alkyl;
- $y^1$ and $y^2$ are each individually 0 or 1; and
- SEQ is an amino acid sequence comprising from 2 to 20 amino acids selected from the group consisting of: L-alanine, L-glycine, L-leucine, L-isoleucine, L-valine, L-phenylalanine, L-tryptophan, L-arginine, L-histidine, L-lysine, L-aspartic acid, L-glutamic acid, L-asparagine, L-glutamine, L-serine, L-threonine, L-tyrosine, L-proline, D-alanine, D-glycine, D-leucine, D-isoleucine, D-valine, D-phenylalanine, D-tryptophan, D-arginine, D-histidine, D-lysine, D-aspartic acid, D-glutamic acid, D-asparagine, D-glutamine, D-serine, D-threonine, D-tyrosine, D-proline, Cyclopropyl Alanine (CyA), Methyl Leucine (MeL), Methyl Valine (MeV), Allylglycine, Methyl Tryptophan (MT), Thiazolyl Alanine (Thz), 2-Naphthyl Alanine (Nap), O-Methyl Tyrosine (OMY), 4-Fluorophenyl Alanine (FP), 4-Cyano Phenylalanine (CN—F), 4-Phenyl Phenylalanine (PhF), 4-Bromo Phenylalanine (Br—F), 4-Pyridyl Alanine (PyrA), 4-Methyl Phenylalanine (Me-F), O-Phenyl Tyrosine (OPhY), β-Phenylalanine (BPhA), Dimethyl Lysine (DMK), 2-Methoxy Pyridylalanine (MeOPyr), Piperazinecarboxylic acid, N-Methyl d-valine (N-Me-v), N-Methyl d-alanine (N-Me-a), Aminocyclobutyl carboxylic acid (ACBC), Aminocyclohexyl carboxylic (ACHC), α-Methyl Alanine (AMA), Morpholinecarboxylic acid, Tetrazoyl Alanine (Ttz), β-Alanine (BAla), and Azetidine carboxylic acid, and
- wherein at least one amino acid in SEQ is CyA, MeL, MeV, Allylglycine, MT, Thz, Nap, OMY, FP, CN—F, PhF, Br—F, PyrA, Me-F, OPhY, BPhA, DMK, MeOPyr, Piperazinecarboxylic acid, N-Me-v, N-Me-a, ACBC, ACHC, AMA, Morpholinecarboxylic acid, Ttz, BAla, or Azetidine carboxylic acid.

2. The cyclic peptide of claim 1, wherein $L^1$, $L^2$, or both, comprise one or more substituents selected from alkyl, alkyne, azide, and aminocarbonyl.

3. The cyclic peptide of claim 1, wherein $L^1$, $L^2$, or both, comprise a linkage selected from a linkage to a solid support, a linkage to a reporter moiety, and a linkage to a peptide ligand.

4. The cyclic peptide of claim 1, wherein $L^1$ and $L^2$ are alkylene.

5. The cyclic peptide of claim 1, wherein the cyclic peptide has the following structure (Ia):

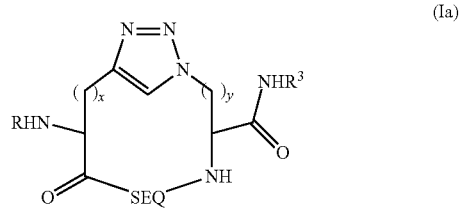

(Ia)

wherein:
- $R^3$ is H, a linkage to a solid support, a linkage to a reporter moiety, a linkage to a peptide ligand, a linkage to an azide or alkyne moiety, or combinations thereof; and
- x and y are each independently an integer from 1 to 8.

6. The cyclic peptide of claim 1, wherein SEQ comprises from 2 to 9 amino acids.

7. The cyclic peptide of claim 6, wherein SEQ comprises from 5 to 7 amino acids.

8. The cyclic peptide of claim 1, wherein the amino acids are selected from Cyclopropyl Alanine (CyA), Gly, 4-Fluorophenyl Alanine (FP), Methyl Tryptophan (MT), 2-Methoxy Pyridylalanine (MeOPyr), 4-Phenyl Phenylalanine (PhF), Asn, Ser, Thr, His, Lys, Arg, Glu, β-Phenylalanine (BPhA), N-Methyl d-alanine (N-Me-a), and Pro.

9. The cyclic peptide of claim 1, wherein the amino acids are selected from Cyclopropyl Alanine (CyA), Gly, 4-Fluorophenyl Alanine (FP), Methyl Tryptophan (MT), Thiazolyl Alanine (Thz), 4-Phenyl Phenylalanine (PhF), Phe, Asn, Ser, Thr, His, Lys, Arg, Glu, N-Methyl d-alanine (N-Me-a), and Pro.

10. The cyclic peptide of claim 1, wherein the amino acids are selected from Cyclopropyl Alanine (CyA), Gly, 4-Fluorophenyl Alanine (FP), Methyl Tryptophan (MT), 2-Methoxy Pyridylalanine (MeOPyr), Thiazolyl Alanine (Thz), 4-Phenyl Phenylalanine (PhF), Phe, Asn, Ser, Thr, His, Lys, Arg, Glu, β-Phenylalanine (BPhA), N-Methyl d-alanine (N-Me-a), and Pro.

11. The cyclic peptide of claim 1, wherein SEQ comprises t(Thz)pk(FP), t(PhF)Gk(FP), t(Thz)hkn (SEQ ID NO:2), t(Thz)(FP)kG, tG(PhF)k(N-Me-a), t(CyA)(PhF)kh, t(CyA)(FP)kn, t(N-Me-a)(N-Me-a)kn, t(N-Me-a)pke (SEQ ID NO:3), tphkn (SEQ ID NO:4), t(CyA)rks (SEQ ID NO:5), tpkk(N-Me-a) (SEQ ID NO:6), t(CyA)ek(N-Me-a), t(CyA)ekh (SEQ ID NO:7), t(CyA)tk(CyA), tesk(CyA) (SEQ ID NO:8), tetk(N-Me-a) (SEQ ID NO:9), tenk(FP) (SEQ ID NO:10), tekkp (SEQ ID NO:11), tskk(N-Me-a) (SEQ ID NO:12), ttrk (SEQ ID NO:13), tnkk(CyA) (SEQ ID NO:14), ts(Thz)k(CyA), tk(FP)kk (SEQ ID NO:15), trrk(CyA) (SEQ ID NO:16), trrks (SEQ ID NO:17), tkrkr (SEQ ID NO:18), trkkh (SEQ ID NO:19), trnkr (SEQ ID NO:20), ttkkr (SEQ ID NO:21), tshkr (SEQ ID NO:22), t(Thz)rkk (SEQ ID NO:23), tr(Thz)kr (SEQ ID NO:24), tr(FP)kr (SEQ ID NO:25), tk(FP)kr (SEQ ID NO:26), trGkr (SEQ ID NO:27), tG(CyA)kr (SEQ ID NO:28), tp(CyA)k(FP), te(MT)kp (SEQ ID NO:29), tnpks (SEQ ID NO:31), tp(Cy)k(FP), t(CyA/e/Thz)(k/FP)k(N-Me-a/n/FP), or trrkr (SEQ ID NO:30).

12. The cyclic peptide of claim 1, wherein R is H or —C(=O)-L$^3$-A, where L$^3$ is a linker moiety and A is a bond to a peptide ligand or an alkyne.

13. The cyclic peptide of claim 12, wherein A is an alkyne.

14. The cyclic peptide of claim 12, wherein A is a bond to a peptide ligand.

15. The cyclic peptide of claim 14, wherein the peptide ligand is a linear peptide.

16. The cyclic peptide of claim 14, wherein the peptide ligand is a cyclic peptide.

17. The cyclic peptide of claim 15, wherein the peptide ligand further comprises a second peptide ligand covalently bound thereto.

18. The cyclic peptide of claim 1, wherein y$^1$ and y$^2$ are each 0.

19. A composition comprising the cyclic peptide of claim 1 and a pharmaceutically acceptable carrier.

20. A library comprising a plurality of cyclic peptides according to claim 1.

21. A method of detecting a target protein in a sample, the method comprising (a) bringing into contact the cyclic peptide of claim 1 and the target protein and (b) detecting the binding of the cyclic peptide to the target protein, wherein SEQ is a peptide sequence having affinity for the target protein.

22. The method of claim 21, wherein the method is in the form of a Western blot, a pull-down assay, a dot blot, or an ELISA in which the antibody normally used in the Western blot, pull-down assay, dot blot, or ELISA is replaced by cyclic peptide.

23. A method of purifying a target, the method comprising immobilizing the A cyclic peptide of claim 1 in a column, contacting the column with a matrix containing the target, washing the column, and eluting the target.

24. A method of imaging in vivo expression of a target, the method comprising:
   (a) providing a cyclic peptide of claim 1, wherein SEQ is a peptide sequence having affinity for the target, and modifying the cyclic peptide to include a small-molecule positron-emission-tomography ligand (PET ligand);
   (b) administering the cyclic peptide of step (a) to the subject;
   (c) measuring the positron emission from the PET ligand at a first time;
   (d) measuring the positron emission from the PET ligand at a second time; and
   (e) comparing the positron emission from the PET ligand at the first and second times wherein the PET ligand comprises a moiety selected from $^{64}$Cu DOTA, $^{68}$Ga DOTA, $^{68}$Ga NOTA, $^{18}$F, $^{64}$Cu, $^{68}$Ga, $^{89}$Zr, $^{124}$I, $^{86}$Y, $^{94m}$Tc, $^{110m}$In, $^{11}$C, and $^{76}$Br.

25. A method of imaging in vivo expression of a target, the method comprising:
   (a) providing a cyclic peptide of claim 1, wherein SEQ is a peptide sequence having affinity for the target, and modifying the cyclic peptide to include a small-molecule single-photon-emission-computed-tomography ligand (SPECT ligand);
   (b) administering the cyclic peptide of step (a) to the subject;
   (c) measuring the photon emission from the SPECT ligand at a first time;
   (d) measuring the photon emission from the SPECT ligand at a second time; and
   (e) comparing the photon emission from the SPECT ligand at the first and second times wherein the SPECT ligand comprises a moiety selected from $^{111}$In DOTA, $^{90}$Y DOTA, $^{111}$In, $^{90}$Y, and $^{99m}$Tc.

26. A method of imaging in vivo expression of a target, the method comprising:
   (a) providing a cyclic peptide of claim 1, wherein SEQ is a peptide sequence having affinity for the target, and modifying the cyclic peptide to include a magnetic resonance ligand (MR ligand);
   (b) administering the cyclic peptide of step (a) to the subject;
   (c) measuring the magnetic resonance from the MR ligand at a first time;
   (d) measuring the magnetic resonance from the MR ligand at a second time; and
   (e) comparing the magnetic resonance from the MR ligand at the first and second times wherein the MR ligand comprises Gd$^{3+}$.

27. The cyclic peptide of claim 1, wherein the cyclic peptide comprises a linkage to a reporter moiety, the reporter moiety selected from polyethylene glycol (PEG), biotin, thiol and fluorophores.

28. The cyclic peptide of claim 27, wherein the fluorophores are selected from carboxyfluorescein (FAM), fluorescein isothiocyanate (FITC), Cyanine-5 (Cy5), tetramethylrhodamine (TRITC) and Carboxytetramethylrhodamine (TAMRA).

* * * * *

SEQUENCE LISTING

```
<160> NUMBER OF SEQ ID NOS: 31

<210> SEQ ID NO 1
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(5)
<223> OTHER INFORMATION: D amino acids

<400> SEQUENCE: 1

Thr Phe Pro Lys Lys
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: D amino acid
<220> FEATURE:
<221> NAME/KEY: MISC_FEATURE
<222> LOCATION: (2)..(2)
<223> OTHER INFORMATION: Xaa is Thiazolyl Alanine
<220> FEATURE:
<221> NAME/KEY: MISC_FEATURE
<222> LOCATION: (3)..(5)
<223> OTHER INFORMATION: D amino acids

<400> SEQUENCE: 2

Thr Xaa His Lys Asn
1               5

<210> SEQ ID NO 3
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: D amino acid
<220> FEATURE:
<221> NAME/KEY: MISC_FEATURE
<222> LOCATION: (2)..(2)
<223> OTHER INFORMATION: Xaa is N-Methyl d-alanine
<220> FEATURE:
<221> NAME/KEY: MISC_FEATURE
<222> LOCATION: (3)..(5)
<223> OTHER INFORMATION: D amino acids

<400> SEQUENCE: 3

Thr Xaa Pro Lys Glu
1               5

<210> SEQ ID NO 4
```

-continued

```
<211> LENGTH: 5
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (1)..(5)
<223> OTHER INFORMATION: D amino acids

<400> SEQUENCE: 4

Thr Pro His Lys Asn
1               5

<210> SEQ ID NO 5
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: D amino acid
<220> FEATURE:
<221> NAME/KEY: MISC_FEATURE
<222> LOCATION: (2)..(2)
<223> OTHER INFORMATION: Xaa is Cyclopropyl Alanine
<220> FEATURE:
<221> NAME/KEY: MISC_FEATURE
<222> LOCATION: (3)..(5)
<223> OTHER INFORMATION: D amino acids

<400> SEQUENCE: 5

Thr Xaa Arg Lys Ser
1               5

<210> SEQ ID NO 6
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(4)
<223> OTHER INFORMATION: D amino acids
<220> FEATURE:
<221> NAME/KEY: MISC_FEATURE
<222> LOCATION: (5)..(5)
<223> OTHER INFORMATION: Xaa is N-Methyl d-alanine

<400> SEQUENCE: 6

Thr Pro Lys Lys Xaa
1               5

<210> SEQ ID NO 7
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: D amino acid
<220> FEATURE:
<221> NAME/KEY: MISC_FEATURE
<222> LOCATION: (2)..(2)
<223> OTHER INFORMATION: Xaa is Cyclopropyl Alanine
<220> FEATURE:
<221> NAME/KEY: MISC_FEATURE
<222> LOCATION: (3)..(5)
```

```
<223> OTHER INFORMATION: D amino acids

<400> SEQUENCE: 7

Thr Xaa Glu Lys His
1               5

<210> SEQ ID NO 8
<211> LENGTH: 5
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (1)..(4)
<223> OTHER INFORMATION: D amino acids
<220> FEATURE:
<221> NAME/KEY: MISC_FEATURE
<222> LOCATION: (5)..(5)
<223> OTHER INFORMATION: Xaa is Cyclopropyl Alanine

<400> SEQUENCE: 8

Thr Glu Ser Lys Xaa
1               5

<210> SEQ ID NO 9
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(4)
<223> OTHER INFORMATION: D amino acids
<220> FEATURE:
<221> NAME/KEY: MISC_FEATURE
<222> LOCATION: (5)..(5)
<223> OTHER INFORMATION: Xaa is N-Methyl d-alanine

<400> SEQUENCE: 9

Thr Glu Thr Lys Xaa
1               5

<210> SEQ ID NO 10
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(4)
<223> OTHER INFORMATION: D amino acids
<220> FEATURE:
<221> NAME/KEY: MISC_FEATURE
<222> LOCATION: (5)..(5)
<223> OTHER INFORMATION: Xaa is 4-Fluorophenyl Alanine

<400> SEQUENCE: 10

Thr Glu Asn Lys Xaa
1               5

<210> SEQ ID NO 11
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
```

```
<222> LOCATION: (1)..(5)
<223> OTHER INFORMATION: D amino acids

<400> SEQUENCE: 11

Thr Glu Lys Lys Pro
1               5

<210> SEQ ID NO 12
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(4)
<223> OTHER INFORMATION: D amino acids
<220> FEATURE:
<221> NAME/KEY: MISC_FEATURE
<222> LOCATION: (5)..(5)
<223> OTHER INFORMATION: Xaa is N-Methyl d-alanine

<400> SEQUENCE: 12

Thr Ser Lys Lys Xaa
1               5

<210> SEQ ID NO 13
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(4)
<223> OTHER INFORMATION: D amino acids

<400> SEQUENCE: 13

Thr Thr Arg Lys
1

<210> SEQ ID NO 14
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(4)
<223> OTHER INFORMATION: D amino acids
<220> FEATURE:
<221> NAME/KEY: MISC_FEATURE
<222> LOCATION: (5)..(5)
<223> OTHER INFORMATION: Xaa is Cyclopropyl Alanine

<400> SEQUENCE: 14

Thr Asn Lys Lys Xaa
1               5

<210> SEQ ID NO 15
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(2)
<223> OTHER INFORMATION: D amino acids
<220> FEATURE:
```

```
<221> NAME/KEY: MISC_FEATURE
<222> LOCATION: (3)..(5)
<223> OTHER INFORMATION: D amino acids
<220> FEATURE:
<221> NAME/KEY: MISC_FEATURE
<222> LOCATION: (4)..(4)
<223> OTHER INFORMATION: Xaa is 4-Fluorophenyl Alanine

<400> SEQUENCE: 15

Thr Lys Xaa Lys Lys
1               5

<210> SEQ ID NO 16
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(4)
<223> OTHER INFORMATION: D amino acids
<220> FEATURE:
<221> NAME/KEY: MISC_FEATURE
<222> LOCATION: (5)..(5)
<223> OTHER INFORMATION: Xaa is Cyclopropyl Alanine

<400> SEQUENCE: 16

Thr Arg Arg Lys Xaa
1               5

<210> SEQ ID NO 17
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(5)
<223> OTHER INFORMATION: D amino acids

<400> SEQUENCE: 17

Thr Arg Arg Lys Ser
1               5

<210> SEQ ID NO 18
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(5)
<223> OTHER INFORMATION: D amino acids

<400> SEQUENCE: 18

Thr Lys Arg Lys Arg
1               5

<210> SEQ ID NO 19
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(5)
<223> OTHER INFORMATION: D amino acids
```

<400> SEQUENCE: 19

Thr Arg Lys Lys His
1               5

<210> SEQ ID NO 20
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(5)
<223> OTHER INFORMATION: D amino acids

<400> SEQUENCE: 20

Thr Arg Asn Lys Arg
1               5

<210> SEQ ID NO 21
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(5)
<223> OTHER INFORMATION: D amino acids

<400> SEQUENCE: 21

Thr Thr Lys Lys Arg
1               5

<210> SEQ ID NO 22
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(5)
<223> OTHER INFORMATION: D amino acids

<400> SEQUENCE: 22

Thr Ser His Lys Arg
1               5

<210> SEQ ID NO 23
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: D amino acids
<220> FEATURE:
<221> NAME/KEY: MISC_FEATURE
<222> LOCATION: (2)..(2)
<223> OTHER INFORMATION: Xaa is Thiazolyl Alanine
<220> FEATURE:
<221> NAME/KEY: MISC_FEATURE
<222> LOCATION: (3)..(5)
<223> OTHER INFORMATION: D amino acids

<400> SEQUENCE: 23

```
Thr Xaa Arg Lys Lys
1               5

<210> SEQ ID NO 24
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(2)
<223> OTHER INFORMATION: D amino acids
<220> FEATURE:
<221> NAME/KEY: MISC_FEATURE
<222> LOCATION: (3)..(3)
<223> OTHER INFORMATION: Xaa is Thiazolyl Alanine
<220> FEATURE:
<221> NAME/KEY: MISC_FEATURE
<222> LOCATION: (4)..(5)
<223> OTHER INFORMATION: D amino acids

<400> SEQUENCE: 24

Thr Arg Xaa Lys Arg
1               5

<210> SEQ ID NO 25
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(2)
<223> OTHER INFORMATION: D amino acids
<220> FEATURE:
<221> NAME/KEY: MISC_FEATURE
<222> LOCATION: (3)..(3)
<223> OTHER INFORMATION: Xaa is 4-Fluorophenyl Alanine
<220> FEATURE:
<221> NAME/KEY: MISC_FEATURE
<222> LOCATION: (4)..(5)
<223> OTHER INFORMATION: D amino acids

<400> SEQUENCE: 25

Thr Arg Xaa Lys Arg
1               5

<210> SEQ ID NO 26
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(2)
<223> OTHER INFORMATION: D amino acids
<220> FEATURE:
<221> NAME/KEY: MISC_FEATURE
<222> LOCATION: (3)..(3)
<223> OTHER INFORMATION: Xaa is 4-Fluorophenyl Alanine
<220> FEATURE:
<221> NAME/KEY: MISC_FEATURE
<222> LOCATION: (4)..(5)
<223> OTHER INFORMATION: D amino acids

<400> SEQUENCE: 26

Thr Lys Xaa Lys Arg
1               5
```

```
<210> SEQ ID NO 27
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(2)
<223> OTHER INFORMATION: D amino acids
<220> FEATURE:
<221> NAME/KEY: MISC_FEATURE
<222> LOCATION: (4)..(5)
<223> OTHER INFORMATION: D amino acids

<400> SEQUENCE: 27

Thr Arg Gly Lys Arg
1               5

<210> SEQ ID NO 28
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: D amino acid
<220> FEATURE:
<221> NAME/KEY: MISC_FEATURE
<222> LOCATION: (3)..(3)
<223> OTHER INFORMATION: Xaa is Cyclopropyl Alanine
<220> FEATURE:
<221> NAME/KEY: MISC_FEATURE
<222> LOCATION: (4)..(5)
<223> OTHER INFORMATION: D amino acids

<400> SEQUENCE: 28

Thr Gly Xaa Lys Arg
1               5

<210> SEQ ID NO 29
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(2)
<223> OTHER INFORMATION: D amino acids
<220> FEATURE:
<221> NAME/KEY: MISC_FEATURE
<222> LOCATION: (3)..(3)
<223> OTHER INFORMATION: Xaa is Methyl Tryptophan
<220> FEATURE:
<221> NAME/KEY: MISC_FEATURE
<222> LOCATION: (4)..(5)
<223> OTHER INFORMATION: D amino acids

<400> SEQUENCE: 29

Thr Glu Xaa Lys Pro
1               5

<210> SEQ ID NO 30
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: misc
```

```
<222> LOCATION: (1)..(5)
<223> OTHER INFORMATION: D amino acids

<400> SEQUENCE: 30

Thr Arg Arg Lys Arg
1               5

<210> SEQ ID NO 31
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(5)
<223> OTHER INFORMATION: D amino acids

<400> SEQUENCE: 31

Thr Asn Pro Lys Ser
1               5
```